United States Patent
Bakaletz et al.

(10) Patent No.: US 12,116,614 B2
(45) Date of Patent: Oct. 15, 2024

(54) METHODS FOR DETERMINING ANTIBIOTIC SENSITIVITY

(71) Applicant: RESEARCH INSTITUTE AT NATIONWIDE CHILDREN'S HOSPITAL, Columbus, OH (US)

(72) Inventors: Lauren O. Bakaletz, Columbus, OH (US); Steven D. Goodman, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 0 days.

(21) Appl. No.: 17/364,578

(22) Filed: Jun. 30, 2021

(65) Prior Publication Data
US 2021/0403976 A1    Dec. 30, 2021

Related U.S. Application Data

(60) Provisional application No. 63/046,314, filed on Jun. 30, 2020.

(51) Int. Cl.
*C12Q 1/18* (2006.01)
(52) U.S. Cl.
CPC ..................... *C12Q 1/18* (2013.01)
(58) Field of Classification Search
CPC .................. C12Q 1/18; A61K 39/395
See application file for complete search history.

(56) References Cited

U.S. PATENT DOCUMENTS

| 7,811,591 | B2 | 10/2010 | Bakaletz et al. |
| 8,999,291 | B2 * | 4/2015 | Goodman ............ C07K 14/285 |
| 10,233,234 | B2 * | 3/2019 | Kauvar ............ C07K 16/1271 |
| 10,940,204 | B2 * | 3/2021 | Bakaletz ............ C07K 16/1242 |

(Continued)

FOREIGN PATENT DOCUMENTS

WO    WO-2005/111066 A2    11/2005

OTHER PUBLICATIONS

Mokrzan et al. "Antibodies against the Majority Subunit (PilA) of the Type IV Pilus of Nontypeable Haemophilus influenzae Disperse Moraxella catarrhalis from a Dual-Species Biofilm", Dec. 11, 2018, mBio, vol. 9 No. 6, p. 1-18. Full text. (Year: 2018).*

(Continued)

*Primary Examiner* — Gary B Nickol
*Assistant Examiner* — Amelia Nicole Dickens
(74) *Attorney, Agent, or Firm* — Foley & Lardner LLP

(57) ABSTRACT

Disclosed are approaches to determining a sensitivity of a bacterium to a given antibiotic and generating targeted treatments based on the sensitivity. One or more antibiotics may be selected for a chronic/recurrent infection resulting from a biofilm so as to reduce dose and or length of course of antibiotic treatment. For example, if a bacterial pathogen is determined to be sensitive to an antibiotic in its planktonic form but resistant to that antibiotic in its biofilm form, then the biofilm may be dispersed or disrupted from the biofilm residence in order to clear the infection. In various embodiments, a dispersal or disruption method and/or agent may be determined based at least in part on a rate of bacterial release from a biofilm that sensitizes the pathogen to a chosen antibiotic.

20 Claims, 21 Drawing Sheets

Specification includes a Sequence Listing.

(56) References Cited

U.S. PATENT DOCUMENTS

| | | | |
|---|---|---|---|
| 11,104,723 B2* | 8/2021 | Goodman | C07K 16/12 |
| 2011/0236306 A1* | 9/2011 | Goodman | A61P 31/04 |
| | | | 424/257.1 |
| 2019/0000971 A1 | 1/2019 | Bakaletz et al. | |

OTHER PUBLICATIONS

Brockson et al. "Evaluation of the kinetics and mechanism of action of anti-integration host factor-mediated disruption of bacterial biofilms", Aug. 19, 2014, Molecular Microbiology, vol. 93 No. 6, p. 1246-1258. (Year: 2014).*

Parrish et al. "Subversion of host immune responses by otopathogens during otitis media", 2019, Journal of Leukocyte Biology, vol. 106, p. 943-956. (Year: 2019).*

Marks et al. "Interkingdom Signaling Induces *Streptococcus pneumoniae* Biofilm Dispersion and Transition from Asymptomatic Colonization to Disease", Jul. 23, 2013, mBio, vol. 4 No. 4, p. 1-13. (Year: 2013).*

Supplemental Figure S5 from Mokrzan et al. "Antibodies against the Majority Subunit (PilA) of the Type IV Pilus of Nontypeable Haemophilus influenzae Disperse Moraxella catarrhalis from a Dual-Species Biofilm", Dec. 11, 2018, mBio, vol. 9 No. 6, p. 1-18. (Year: 2018).*

Mokrzan et al. "Nontypeable Haemophilus influenzae newly released (NRel) from biofilms by antibody-mediated dispersal versus antibody-mediated disruption are phenotypically distinct", Biofilm, vol. 2, Article 100039, p. 1-13. (Year: 2020).*

Wiegand et al. "Agar and broth dilution methods to determine the minimal inhibitory concentration (MIC) of antimicrobial substances", Jan. 17, 2008, Nature Protocols, vol. 3 No. 2, p. 163-175. (Year: 2008).*

Mokrzan et al. "Antibodies against the Majority Subunit (PilA) of the Type IV Pilus of Nontypeable Haemophilus influenzae Disperse Moraxella catarrhalis from a Dual-Species Biofilm", Dec. 11, 2018, mBio, vol. 9 No. 6, p. 1-18. (Year: 2018).*

International Search Report and Written Opinion dated Apr. 26, 2022, from application serial No. PCT/US2021/057626, 15 pages.

Mokrzan. "Antibodies against the Majority Subunit (PilA) of the Type IV Pilus of Nontypeable Haemophilus influenzae Disperse Moraxella catarrhalis from a Dual-species Biofilm" 1. American society for microbiology. Web. Dec. 11, 2018; Abstract; DOI: 10.1128/mBio.02423-18.

Novotny et al. "Antibodies against the majority subunit of type IV Pili disperse nontypeable Haemophilus influenzae biofilms in a LuxS-dependent manner and confer therapeutic resolution of experimental otitis media" Mol Microbiol. Apr. 2015;96(2):276-92. doi: 10.1111/mmi.12934. First published: Jan. 19, 2015.

Brockson, ME, et al., "Evaluation of the kinetics and mechanism of action of anti-anti-integration host factor mediated disruption of bacterial biofilms," Mol Microbiol, Sep. 2014, 93(6):1246-1258, 22 pages.

International Preliminary Report on Patentability issued in Application No. PCT/US2021/057626, dated May 11, 2023, 9 pages.

Mokrzan E. et al., "Nontypeable Haemophilus influenczae newly released (NRel) from biofilms by antibody-mediated dispersal versus antibody-mediated disruption are phenotypically distinct," Biofilm 2 (2020) 100039, 13 pages.

Novotny, et al., "Transcutaneous Immunization with a Band-Aid Prevents Experimental Otitis Media in a Polymicrobial Model," Clinical Vaccine Immunology, Jun. 2017, vol. 24, Issue 6, e00563-16, 12 pages.

D'Andrea & Lau, "DNABII targeting antibodies as vaccines against biofilm diseases," eBioMedicine 58:102921, Aug. 1, 2020, 2 pages.

Jurcisek & Bakaletz, "Biofilms Formed by Nontypeable Haemophilus influenzae In Vivo Contain both Double-Stranded DNA and Type IV Pilin Protein," Journal of Bacteriology 189(10), May 15, 2007, pp. 3868-3875.

Jurcisek, et al., "Monoclonal antibodies that target extracellular DNABII proteins or the type IV pilus of nontypeable Haemophilus influenzae (NTHI) worked additively to disrupt 2-genera biofilms," Biofilm 4:100096, Dec. 2022, 14 pages.

Novotny, et al., "Monoclonal antibodies against DNA-binding tips of DNABII proteins disrupt biofilms in vitro and induce bacterial clearance in vivo," eBioMedicine 10, Aug. 1, 2016, pp. 33-44.

Novotny, et al., "Redirecting the immune response towards immunoprotective domains of a DNABII protein resolves experimental otitis media," npj Vaccines 4:43, Oct. 14, 2019, 12 pages.

Novotny, et al., "Targeting a bacterial DNABII protein with a chimeric peptide immunogen or humanised monoclonal antibody to prevent or treat recalcitrant biofilm-mediated infections," eBioMedicine 59:102867, Sep. 1, 2020, 13 pages.

* cited by examiner

- NTHI Biofilms established for 16 h, exposed to MsrsPilAMab or sBHI for different times
- Determine relative antibiotic sensitivity of each NRel compared to time-matched nonassoc NTHI

METHODS FOR DETERMINING ANTIBIOTIC SENSITIVITY

CROSS-REFERENCE TO RELATED APPLICATION

This application claims priority under 35 U.S.C. § 119(e) of U.S. Provisional Application No. 63/046,314, filed Jun. 30, 2020, the contents of which is incorporated by reference in its entirety into the present application.

STATEMENT OF GOVERNMENT RIGHTS

This invention was made with government support under DC003915 and DC011818 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 11, 2022, is name 106887-9010_SL.txt and is 18,000 bytes in size.

BACKGROUND

Bacterial infections are often treated on a trial and error basis, with one antibiotic attempted at first and, if the infection does not respond as expected, other antibiotics attempted. This does not consider whether the particular population of bacteria causing the infection is susceptible to the antibiotic being prescribed when it is being prescribed. Such use of antibiotics could lead to increased antibiotic resistance, unnecessary side effects, longer treatment times, increased morbidity, and/or increased costs.

The Centers for Disease Control and Prevention and the National Institutes of Health estimate that biofilms contribute to the pathogenesis of ~80% of all bacterial infections (Dongari-Bagtzoglou, 2008). Biofilm-associated diseases such as otitis media (OM), cystic fibrosis, chronic obstructive pulmonary disease, chronic rhinosinusitis, chronic wound infections, periodontitis, cystitis and infections of medical implants and indwelling catheters, among many others, are typically chronic and/or recurrent due to the presence of bacteria within biofilms that are highly resistant to killing by host immune effectors and antibiotics (Costerton et al., 1999; Flemming and Wingender, 2010). Nontypeable *Haemophilus influenzae* (NTHI) biofilms have been shown to contribute significantly to diseases of the upper and lower respiratory tracts (Ahearn et al., 2017; Cardines et al., 2012; Pang et al., 2012). An example of one such disease wherein NTHI is the predominant pathogen is OM (Barkai et al., 2009; Cleary et al., 2018; Grevers et al., 2012; Vergison, 2008; Wiertsema et al., 2011), the most common bacterial disease in children (Hassan, 2013; Mittal et al., 2018). The role of biofilms in OM pathogenesis, chronicity and recurrence is widely accepted. Nonetheless, like most NTHI-induced diseases, OM is still commonly treated with broad-spectrum oral antibiotics, which do not reach sufficient levels in the middle ear (or other sites) to eradicate biofilms or even the planktonically growing bacteria within this anatomical niche (Belfield et al., 2015). Although their use is sometimes indicated or necessary, broad-spectrum antibiotics can also cause collateral damage in the form of skin rashes, diarrhea and life-long disruption of the gut microbiome, with accompanied immunological and/or developmental consequences (Gilbert et al., 2018; Kuehn et al., 2015; Lamont et al., 2020). Moreover, the all too common indiscriminate and often ineffective use of antibiotics contributes greatly to the globally burgeoning problem of development of multiple antibiotic-resistant bacteria (Beekmann et al., 2005; Leibovitz et al., 2010; Song et al., 2012). Thus, a need exists in the art for safe and effective therapies that target and treat biofilm-related disease. This disclosure satisfies that need and provides related advantages as well.

BRIEF DESCRIPTION OF THE DRAWINGS

(FIG. 2A) The anti-rsPilA (α-rsPilA, dark grey dots) and anti-IHF (α-IHF, light grey dots) NRels have distinct proteomic expression profiles compared to one another that are also distinct from planktonically grown NTHI (black dots) shown by a principal component analysis (PCA) plot generated from the normalized spectral counts of each protein in samples with 95% confidence ellipses drawn around triplicate samples of each population. (FIG. 2B) The anti-rsPilA (α-rsPilA, dark grey bars) and anti-IHF (α-IHF, light grey bars) NRels have distinct expression patterns of proteins with a significant (P<0.05) 1.5-fold increase or decrease represented by different COG categories when compared to planktonically grown NTHI. (FIG. 2C) Anti-IHF (light grey bars) and anti-rsPilA (dark grey bars) NRel have differences in protein expression profiles of proteins with a significant (P<0.05) 1.5-fold increase or decrease compared to one another as shown by a volcano plot of anti-IHF NRel versus anti-rsPilA NRel. Negative fold decreases represent proteins with greater abundance in the anti-rsPilA NRels (dark greydots), while positive fold increases represent greater protein abundance in the anti-IHF NRels (light grey dots) compared to each other. (FIG. 2D) Venn diagram of the number of proteins with a significant (P<0.05) 1.5-fold increase (above the dashed line) or decrease (below the dashed line) specific to anti-rsPilA (dark grey), anti-IHF (light grey), or shared, compared to planktonic NTHI.

(FIG. 3A) Diagram of the distinct subpopulations of NTHI tested herein. NRels were generated by incubation of NTHI biofilms with rabbit polyclonal IgG from anti-rsPilA (6 hr, dark grey) or anti-IHF (15 min, light grey). (3B and 3C) Anti-rsPilA NRels were significantly more sensitive to killing by trimethoprim/sulfamethoxazole than planktonic NTHI (T/S, 3B), but only equally as sensitive to killing by amoxicillin/clavulanate (A/C, FIG. 3C). Biofilm-resident NTHI displayed minimal sensitivity to either T/S or A/C. (Panels B to E) In contrast, anti-IHF NRels were only equally as sensitive to killing by T/S as planktonic NTHI (3D), but significantly more sensitive to killing by A/C (3E). The unique sensitivity of NTHI NRel to killing by either T/S or A/C was dependent upon the mechanism by which they were released from biofilm residence. * P<0.05,  P<0.01 ** P<0.0001, One-way analysis of variance with the Holm-Sidak correction.

(FIG. 4A & FIG. 4B) Anti-rsPilA NRel were significantly more sensitive to killing by TMP/SMX than planktonic NTHI (TMP-SMX at 0.09 µg and 0.45 µg per ml, but only equally as sensitive to killing by AMC (AMC at 0.3 µg and 0.15 µg per ml). In contrast, anti-IHF NRel were only equally as sensitive to killing by TMP-SMX as planktonic NTHI (0.94 and 4.7 µg/ml respectively), but significantly more sensitive to killing by AMC (2.5 and 1.25 µg/ml respectively). These data showed that time-matched anti-rsPilA or anti-IHF NRel maintained the same distinct antibiotic sensitivity phenotype as shown when 15 min anti-IHF NRel were compared to 6 h anti-rsPilA NRel (see FIG. 3). Individual data points are shown, bars represent mean±SEM. **** P<0.0001, one-way analysis of variance with the Holm-Sidak correction.

(FIG. 5A) Contour plots depicted side scatter and forward scatter profiles for two control samples, NTHI briefly sonicated to produce an individual cell suspension or NTHI colonies collected from an agar plate to represent bacterial aggregates, assessed by flow cytometry. Representative contour plots of (FIG. 5B) anti-rsPilA NRel and (FIG. 5C) anti-IHF NRel demonstrated unique scatter profiles between the two NRel populations. The distribution of anti-IHF NRel (orange histogram) versus anti-rsPilA NRel (dark grey histogram) by (FIG. 5D) forward scatter and (FIG. 5E) side scatter was also distinct. The percent increase in cumulative distribution of anti-IHF NRel compared to anti-rsPilA NRel shown in (FIG. 5D) and (FIG. 5E) was determined by Kolmogorov-Smirnov test (99% CI). These data represented an additional discriminative characteristic of NRel populations generated via exposure to either anti-rsPilA or anti-DNABII antibody-mediated release of NTHI from biofilm residence.

(FIG. 6A) Relative expression of deal), artM, and fis, genes associated with lag phase of growth, was significantly greater in anti-IHF vs. anti-rsPilA NRel. (FIG. 6B) The enzymes targeted by TMP and SMX are encoded by folA and folP respectively, and thereby increased expression confers resistance. Relative expression of folA and folP by anti-rsPilA NRel was significantly less than by anti-IHF NRel. (FIG. 6C) Relative expression of emrA and emrB, which encode subunits of an efflux pump that transports TMP-SMX, was significantly less by anti-rsPilA vs. anti-IHF NRel. Expression of acrR, which represses the efflux pump that transports AMC, was significantly elevated in anti-IHF vs. anti-rsPilA NRel. These patterns of relative gene expression support the enhanced sensitivities of anti-rsPilA or anti-IHF NRel to TMP-SMX or AMC, respectively. * P<0.05, * P<0.001, ** P<0.0001, Student's t-test.

DETAILED DESCRIPTION

Definitions

Figure 1A:
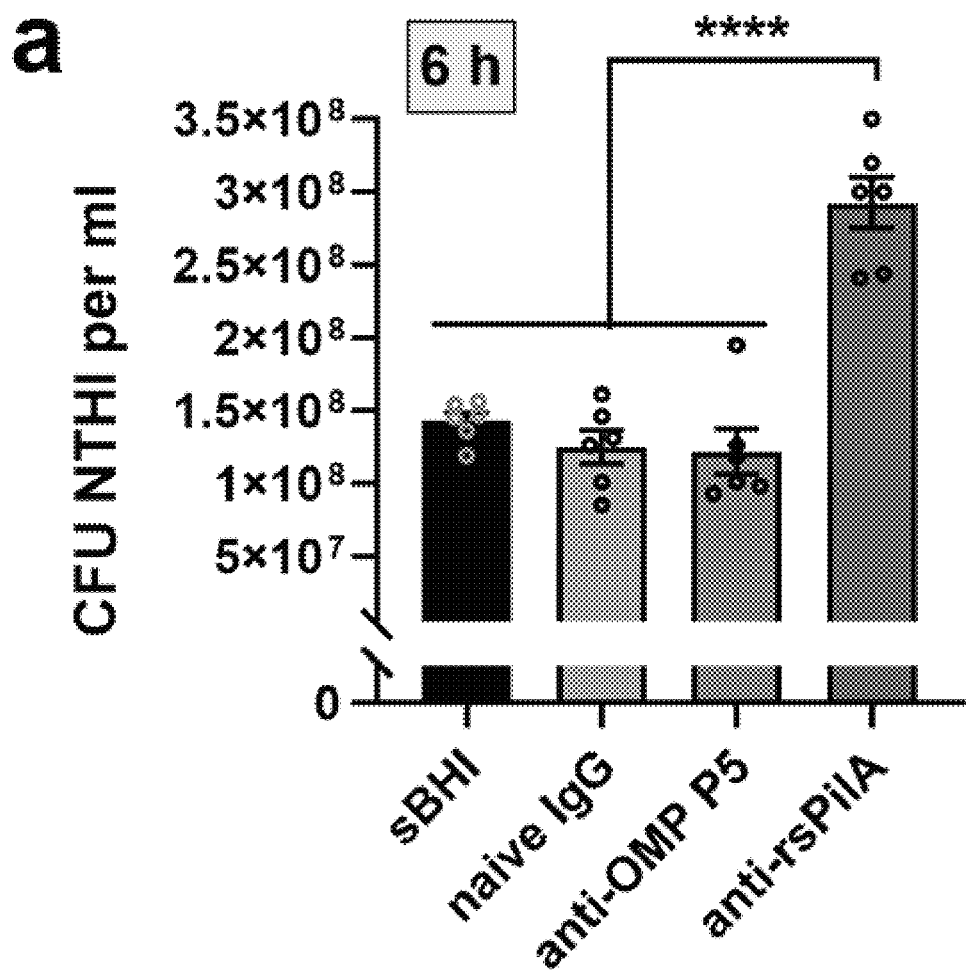
FIGS. 1A and 1B show biofilm-residence release. Quantitation of NTHI released from biofilm-residence by either anti-rsPilA or anti-IHF. NTHI biofilms established for 16 hr were incubated for an additional (FIG. 1A) 6 hr with rabbit anti-rsPilA or (FIG. 1B) 15 min with rabbit anti-IHF or control sera and NRel populations quantitated. Anti-rsPilA or anti-IHF induced significant release of NTHI from biofilms into the NRel state. ****, P<0.0001, One-way analysis of variance with the Holm-Sidak correction.

Unless defined otherwise, all technical and scientific terms used herein have the same meanings as commonly understood by one of ordinary skill in the art to which this disclosure belongs. All nucleotide sequences provided herein are presented in the 5' to 3' direction. Although any methods and materials similar or equivalent to those described herein can be used in the practice or testing of the present disclosure, particular, non-limiting exemplary methods, devices, and materials are now described. All technical and patent publications cited herein are incorporated herein by reference in their entirety. Nothing herein is to be construed as an admission that the disclosure is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds, (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of"

when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions disclosed herein. Embodiments defined by each of these transition terms are within the scope of this disclosure.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the terms "exemplary," "example," "potential," and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the Figures. It should be noted that the orientation of various elements may differ according to other exemplary embodiments, and that such variations are intended to be encompassed by the present disclosure.

Several embodiments may be described herein with reference to drawings. The drawings illustrate certain details of specific embodiments that implement the systems, methods and programs described herein. However, describing the embodiments with drawings should not be construed as imposing on the disclosure any limitations that may be present in the drawings.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

A "biofilm" intends an organized community of microorganisms that at times adhere to the surface of a structure, that may be organic or inorganic, together with the polymers such as DNA that they secrete, release and/or become available in the extracellular milieu due to bacterial lysis. The biofilms are very resistant to microbiotics and antimicrobial agents. They live on gingival tissues, teeth and restorations, causing caries and periodontal disease, also known as periodontal plaque disease. They also cause chronic middle ear infections. Biofilms can also form on the surface of dental implants, stents, catheter lines and contact lenses. They grow on pacemakers, heart valve replacements, artificial joints and other surgical implants. The Centers for Disease Control) estimate that over 65% of nosocomial (hospital-acquired) infections are caused by biofilms. They cause chronic vaginal infections and lead to life-threatening systemic infections in people with hobbled immune systems. Biofilms also are involved in numerous diseases. For instance, cystic fibrosis patients have *Pseudomonas* infections that often result in antibiotic resistant biofilms. In one embodiment, the biofilm comprises a DNABII polypeptide or protein. In a further embodiment, the biofilm comprises an IHF and/or an HU. In yet a further embodiment, the biofilm comprises an IHFA and/or an IHFB.

A "biofilm associated disease" intends a disease or condition in which a biofilm is present at some point in the disease state. Non-limiting examples include: chronic non-healing wounds, *Burkholderia*, venous ulcers, diabetic foot ulcers, ear infections, sinus infections, urinary tract infections, cardiac disease, gastrointestinal tract ailments, pulmonary infections, respiratory tract infections, cystic fibrosis, chronic obstructive pulmonary disease, catheter-associated infections, indwelling devices associated infections, infections associated with implanted prostheses, osteomyelitis, cellulitis, abscesses, and periodontal disease. In one aspect it is cystic fibrosis. In another aspect it is inner ear infections.

"Inhibiting, preventing or disrupting" a biofilm intends the prophylactic or therapeutic reduction in the structure of a biofilm.

The term "disrupt" intends a reduction in the formation of the DNA/protein matrix that is a component of a microbial biofilm. In certain embodiments, disrupting a biofilm refers to dispersing the biofilm, releasing microorganisms from the DNA/protein matrix of the biofilm, and optionally allowing killing the microorganisms by host immune effectors and/or antibiotics.

A "DNABII polypeptide or protein" intends a DNA-binding protein or polypeptide that is composed of DNA-binding domains and thus have a specific or general affinity for microbial DNA. In one aspect, they bind DNA in the minor grove. Non-limiting examples of DNABII proteins are an integration host factor (IHF) protein and a histone-like protein from *E. coli* strain U93 (HU). Other DNA binding proteins that may be associated with the biofilm include DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP_418813).

An "integration host factor" or "IHF" protein is a bacterial protein that is used by bacteriophages to incorporate their DNA into the host bacteria. They also bind extracellular microbial DNA. The genes that encode the IHF protein subunits in *E. coli* are himA (Genbank Accession No.: POA6X7.1) and himD (POA6Y1.1) genes. Homologs for these genes are found in other organisms. In certain embodiments, the term "IHF" refers to one or both of the two IHF subunits: integration host factor subunit alpha (IHFA or IhfA) and integration host factor subunit beta (IHFB or IhfB).

"HU" or "histone-like protein from *E. coli* strain U93" refers to a class of heterodimeric proteins typically associate with *E. coli*. HU proteins are known to bind DNA junctions. Related proteins have been isolated from other microorganisms. The complete amino acid sequence of *E. coli* HU was reported by Laine et al. (1980) Eur. J. Biochem 103(3) 447-481. Antibodies to the HU protein are commercially available from Abcam. Homologs for these genes are found in other organisms, and peptides corresponding to these genes from other organisms can be found in Table 10 of WO 2011/123396.

The term "surface antigens" or "surface proteins" refers to proteins or peptides on the surface of cells such as bacterial cells. Examples of outer membrane proteins such as OMP P5 (Genbank Accession No.: YP_004139079.1), OMP P2 (Genbank Accession No.: ZZX87199.1) and OMP P26 (Genbank Accession No.: YP_665091.1) whereas examples of surface antigens are rsPilA or recombinant soluble PilA (Genbank Accession No.: EFU96734.1) and Type IV Pilin (Genbank Accession No.: Yp_003864351.1).

The term "*Haemophilus influenzae*" refers to pathogenic bacteria that can cause many different infections such as, for example, ear infections, eye infections, and sinusitis. Many different strains of *Haemophilus influenzae* have been isolated and have an IhfA, ihfB and hupA genes or protein. Some non-limiting examples of different strains of *Haemophilus influenzae* include Rd KW20, 86-028NP, R2866, PittGG, PittEE, R2846, and 2019.

"Microbial DNA" intends single or double stranded DNA from a microorganism that is incorporated into a biofilm.

A "bent polynucleotide" intends a double strand polynucleotide that contains a small loop on one strand which does not pair with the other strand. In some embodiments, the loop is from 1 base to about 20 bases long, or alternatively from 2 bases to about 15 bases long, or alternatively from about 3 bases to about 12 bases long, or alternatively from about 4 bases to about 10 bases long, or alternatively has about 4, 5, or 6, or 7, or 8, or 9, or 10 bases.

A "subject" of diagnosis or treatment is a cell or an animal such as a mammal, or a human. Non-human animals subject to diagnosis or treatment and are those subject to infections or animal models, for example, simians, murines, such as, rats, mice, chinchilla, canine, such as dogs, leporids, such as rabbits, livestock, sport animals, and pets. The term "subject," "host," "individual," and "patient" are as used interchangeably herein to refer to animals, typically mammalian animals. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. In some embodiments a subject is a human. In one aspect, the subject is a pediatric patient.

As used herein, the ESKAPE pathogens include *Enterococcus faecium, Staphylococcus aureus, Klebsiella pneumoniae, Acinetobacter baumannii, Pseudomonas aeruginosa*, and *Enterobacter* species. These pathogens are the leading cause of nosocomial infections throughout the world.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, an equivalent of a polypeptide refers to a sequence that is at least about 70%, or alternatively at least about 75%, or at least about 80%, or at least about 85%, or at least about 90%, or at least about 95%, or at least about 98% or at least about 99% identical to the reference polypeptide that in one aspect, retain the mutated amino acid(s). In some aspects, the equivalent of a polypeptide retains the intended function and/or structural characteristics of the reference polypeptide.

An immunodominant antigen intends a region of the protein that is recognized and binds with high affinity to an antibody.

An immunoprotective antigen intends a region of the protein that is recognized and binds with high affinity to an antibody to interfere with protein function; the antibodies generated against an immunoprotective antigen are characterized by enhanced or optimal effect against a target indication as a result to the interference with protein function—in this case, an improve capability to clear biofilms.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment as determined by a method as disclosed herein. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. Examples of biologically equivalent polypeptides are provided in Table 9 of WO 2011/123396 which identifies conservative amino acid substitutions.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases-non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity were determined by incorporating them into clustalW (available at the web address:align.genome.jp, last accessed on Mar. 7, 2011).

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder. As used herein, "treating" or "treatment" of a disease in a subject can also refer to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, treatment excludes prophylaxis.

To prevent intends to prevent a disorder or effect in vitro or in vivo in a system or subject that is predisposed to the disorder or effect. An example of such is preventing the formation of a biofilm in a system that is infected with a microorganism known to produce one.

A "composition" is intended to mean a combination of active agent and another compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

The compositions used in accordance with the disclosure can be packaged in dosage unit form for ease of administration and uniformity of dosage. The term "unit dose" or "dosage" refers to physically discrete units suitable for use in a subject, each unit containing a predetermined quantity of the composition calculated to produce the desired responses in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions are administered in a manner compatible with the dosage formulation and in such amount as is therapeutically or prophylactically effective. The formulations are easily administered in a variety of dosage forms, such as the type of injectable solutions described herein.

As used herein, the term "contacting" means direct or indirect binding or interaction between two or more molecules. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, and topical application.

An agent of the present disclosure can be administered for therapy by any suitable route of administration. It will also be appreciated that the optimal route will vary with the condition and age of the recipient, and the disease being treated.

Dosing of can be accomplished in accordance with the methods disclosed herein using capsules, tablets, oral suspension, suspension for intra-muscular injection, suspension for intravenous infusion, get or cream for topical application, or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In certain embodiments, compositions exhibit high therapeutic indices. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies (in certain embodiments, within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As used herein, the term "contacting" means direct or indirect binding or interaction between two or more molecules. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof. The biological active agents can be conjugated to a pharmaceutically acceptable polymer for administration in accordance with the methods described herein.

As used herein the term "eDNA" refers to extracellular DNA found as a component to pathogenic biofilms.

As used herein, the terms "antibody," "antibodies" and "immunoglobulin" includes whole antibodies and any antigen binding fragment or a single chain thereof. Thus, the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', F(ab)$_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region (which is also referred to herein as a variable domain), a heavy chain or light chain constant region (which is also referred to herein as a constant domain), a framework (FR) region, or any portion thereof, at least one portion of a binding protein, chimeric antibodies, humanized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues. The term "anti-" when used before a protein name, anti-DNABII, anti-IHF, anti-HU, anti-OMP P5, anti-PilA, anti-rsPilA, for example, refers to a monoclonal or polyclonal antibody that binds and/or has an affinity to a particular protein. For example, "anti-IHF" refers to an antibody that binds to the IHF protein. The specific antibody may have affinity or bind to proteins other than the protein it was raised against. For example, anti-IHF, while specifically raised against the IHF protein, may also bind other proteins that are related either through sequence homology or through structure homology.

An anti-PilA antibody refers to an antibody or fragment thereof (e.g., containing the necessary CDRs for antigen binding) that binds the majority subunit of NTHI type IV pilus (T4P) (PilA), and includes a recombinant and soluble form of PilA ('rsPilA'). As disclosed herein, these antibodies are shown to induce dispersal of pre-existing NTHI as well as polymicrobial biofilms in vitro, and also those present within the middle ear in a chinchilla model of NTHI-induced OM wherein biofilm dispersal leads to rapid disease resolution. Examples of such antibodies are disclosed in Mokrzan et al., 2018; Novotny et al., 2009; Novotny et al., 2013b; Novotny et al., 2016; Novotny et al., 2015; Ysebaert et al., 2019) and U.S. Pat. Nos. 8,741,304 and 7,501,131 and US Patent Publication Nos. 2017/0106075, 2014/0199350, 2013/0142803, 20130064828, 2011/0150889, 2011/0150889, 2011/0081357, 2009/0041774, 2008/0311110, and 2005/0158335, all incorporated herein by reference.

An anti-DNABII antibody intends an antibody the binds to a DNABII polypeptide or a fragment thereof, including e.g., IHF, HU or a fragment thereof. The present disclosure utilizes antibodies and fragments thereof that comprise a heavy chain (HC) variable domain sequence and a light chain (LC) variable domain sequence, wherein the heavy chain and light chain immunoglobulin variable domain sequences form an antigen binding site that binds to an epitope of a DNABII protein. In certain embodiments, the antibody or fragment thereof binds to a DNABII peptide (such as the tip region of the DNABII peptide including but not limited to: a tip region of IHF or HU, a tip region of IHFA or IHFB, and/or the tip-chimeric peptide IhfA5-mIhfB4$_{NTHi}$; and/or the tail region of the DNABII peptide, including but not limited to: a tail region of IHF or HU, a tail region of IHFA or IHFB, and/or the tail-chimeric peptide. Non-limiting examples of such antibodies are disclosed in U.S. Pat. Nos. 10,940,204; 10,595,530; 10,570,193; 10,233,234; 8,999,291; and 10,570,193 and published patent application such as US Publ. No. 2021/0139551; 2019/0338018; 2019/0337996; 2019/0000971; 2018/0303900 and PCT Publication No.: PCT/US2020/041082, all incorporated by reference.

A "tip fragment" of a DNABII polypeptide intends a DNABII polypeptide that, using IHFalpha and IHFbeta as examples, forms the two arms of the proteins. See, e.g., FIG. 1 of PCT/US2020/04182. Non-limiting examples of such include IhfA, A tip fragment: NFELRDKSSRPGRNPKTGDVV (SEQ ID NO: 1), and IhfB, B tip fragment: SLHHRQPRLGRNPKTGDSVNL (SEQ ID NO: 2). Another example is a chimeric tip fragment such as IhfA tip and IhfmB4 modified fragment having the peptides of (tip-chimeric peptide IhfA5-mIhfB4$_{NTHI}$) comprising, or consisting essentially of, or yet further consisting of: RPGRNPX$_1$TGDVVPVSARRVV-X-FSLHHRQPRLGRNPX$_1$TGDSV (SEQ ID NO: 3), wherein "X" is an optional amino acid linker sequence, optionally comprising, or consisting essentially of, or yet further consisting of between 1 to 20 amino acids, wherein "X$_1$" is any amino acid or alternatively "X$_1$" is selected from the amino acids Q, R, K, S, or T.

A "tail fragment" of a DNABII polypeptide intends a region of the protein that is both exposed to the bulk medium and not occluded by DNA or other polypeptides.

An example of a anti-DNABII antibody is a humanized antibody that specifically binds a tip domain or chimera thereof of a DNABII (e.g., IHF) peptide. Non-limiting examples of such are provided in PCT Publication No.: PCT/US2020/041082.

A non-limiting example of an anti-DNABII antibody or fragment thereof comprises: a heavy chain complementarity-determining region 1 (CDRH1) comprising a sequence of GFTFRTY (SEQ ID NO: 4); a heavy chain complementarity-determining region 2 (CDRH2) comprising a sequence of GSDRRH (SEQ ID NO: 5); a heavy chain complementarity-determining region 3 (CDRH3) comprising a sequence of VGPYDGYYGEFDY (SEQ ID NO: 6); a light chain complementarity-determining region 1 (CDRL1) comprising a sequence of QSLLDSDGKTF (SEQ ID NO: 7); a light chain complementarity-determining region 2 (CDRL2) comprising a sequence of LVS; and a light chain complementarity-determining region 3 (CDRL3) comprising a sequence of WQGTHFP (SEQ ID NO: 8). Another non-limiting example of an antibody or fragment thereof comprises: a heavy chain complementarity-determining region 1 (CDRH1) comprising a sequence of GFTFRTYA (SEQ ID NO: 9); a heavy chain complementarity-determining region 2 (CDRH2) comprising a sequence of IGSDRRHT (SEQ ID NO: 10); a heavy chain complementarity-determining region 3 (CDRH3) comprising a sequence of VGPYDGYYGEFDY(SEQ ID NO: 6); a light chain complementarity-determining region 1 (CDRL1) comprising a sequence of QSLLDSDGKTF (SEQ ID NO: 7); a light chain complementarity-determining region 2 (CDRL2) comprising a sequence of LVS; and a light chain complementarity-determining region 3 (CDRL3) comprising a sequence of WQGTHFPYT (SEQ ID NO: 11). A further example is an antibody or a fragment thereof, which comprises: a heavy chain complementarity-determining region 1 (CDRH1) comprising a sequence of aASGFTFRTYAMS (SEQ ID NO: 12), wherein the small letter a is A or K; a heavy chain complementarity-determining region 2 (CDRH2) comprising a sequence of TIGSDRRHTY (SEQ ID NO: 13); a heavy chain complementarity-determining region 3 (CDRH3) comprising a sequence of VGPYDGYYGEFDY (SEQ ID NO: 6); a light chain complementarity-determining region 1 (CDRL1) comprising a sequence of rSSQSLLDSDGKTFLN (SEQ ID NO: 14), wherein the smaller letter r is R or K; a light chain complementarity-determining region 2 (CDRL2) comprising a sequence of YLVSKIDS, (SEQ ID NO: 15) wherein the smaller letter l is L or R; and a light chain complementarity-determining region 3 (CDRL3) comprising a sequence of WQGTHFPYT (SEQ ID NO: 11). Another example is an antibody or a fragment thereof that comprises: a heavy chain complementarity-determining region 1 (CDRH1) comprising a sequence of GFTFSRY (SEQ ID NO: 16); a heavy chain complementarity-determining region 2 (CDRH2) comprising a sequence of SSGGSY (SEQ ID NO: 17); a heavy chain complementarity-determining region 3 (CDRH3) comprising a sequence of ER; a light chain complementarity-determining region 1 (CDRL1) comprising a sequence of QDISNY (SEQ ID NO: 18); a light chain complementarity-determining region 2 (CDRL2) comprising a sequence of YTS; and a light chain complementarity-determining region 3 (CDRL3) comprising a sequence of QQ. These antibodies or a fragments thereof can further comprise a constant region selected from the group of: an IgA constant region, an IgD constant region, an IgE constant region, an IgG constant region or an IgM constant region. In one aspect, the constant region is an IgG1 constant region. In one aspect, the antibody identified as HuTipMab intends an antibody having the heavy and light chains or the CDRs:
(1F8.F1 Humanized HCl))

Bold font indicates an exemplified variable region while the bold, italic and underlined font indicates exemplified CDRs:

```
                                          (SEQ ID NO: 19)
MDPKGSLSWRILLFLSLAFELSYGEVQLVESGGGLVQPGGSLRLSCAAS

GFTFRTYAMSWVRQAPGKGLEWVATIGSDRRHTYYPDSVKGRFTISRDN

SKNTLYLQMNSLRAEDTAVVYCVGPYDGYYGEFDYWGQGTLVTVSSAST

KGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPK

SCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNG

KEYCKVSNKALPAPIEKTISKAKGQPREPQVYTLPPSREEMTKNQVLST

CLVKGFYPSDIAVEWESNGQPENNYKTTPPVLDSDGSFFLYSKLTVDKS

RWQQGNVFSCSVMHEALHNHYTQKSLSLSPG**
```

1F8.F1 Humanized (LC2) Bold font indicates an exemplified variable region while the bold, italic and underlined font indicates exemplified CDRs:

```
                                          (SEQ ID NO: 20)
METDTLLLWVLLLWVPGSTGDVVMTQSPLSLPVTLGQPASISCRSS

QSLLDSDGKTFLNWLQQRPGQSPRRLIYLVSKRDSGVPDRFSGSGS

GTDFTLKISRVEAEDVGVYYCWQGTHFPYTFGQGTKLEIKRTVAAP

SVFIFPPSDEQLKSGTASVVCLLNNFYPREAKVQWKVDNALQSGNS

QESVTEQDSKDSTYSLSSTLTLSKADYEKHKVYACEVTHQGLSSPV

TKSFNRGEC*
```

Additional antibodies and fragments comprising the peptides are provided as examples below:

| | | 1 | 2 | 3 | 4 | 5 | 6 | 7 | 8 |
|---|---|---|---|---|---|---|---|---|---|
| VH1 | CDR1 | AASGFTFRTYAMS (SEQ ID NO: 21) | GFTFRTYA (SEQ ID NO: 9) | GFTFRTY (SEQ ID NO: 4); | AASGFTFRTYAMS (SEQ ID NO: 21) | GFTFRTYA (SEQ ID NO: 9) | GFTFRTY (SEQ ID NO: 4); | GFTFRTYA (SEQ ID NO: 9) | GFTFRTY (SEQ ID NO: 4); |
| | CDR2 | TIGSDRRHTY (SEQ ID NO: 13) | IGSDRRHT (SEQ ID NO: 10) | GSDRRH (SEQ ID NO: 5) | TIGSDRRHTY (SEQ ID NO: 13) | IGSDRRHT (SEQ ID NO: 10) | GSDRRH (SEQ ID NO: 5) | IGSDRRHT (SEQ ID NO: 10) | GSDRRH (SEQ ID NO: 5) |

-continued

|  |  | 1 | 2 | 3 | 4 | 5 | 6 | 7 | 8 |
|---|---|---|---|---|---|---|---|---|---|
|  | CDR3 | Not determined | Not determined | Not determined | Not determined | Not determined | Not determined | VGPYDGYYGEFDY (SEQ ID NO: 6) | VGPYDGYYGEFDY (SEQ ID NO: 6) |
| VH2 | CDR1 | AASGFTFRTYAMS (SEQ ID NO: 21) | GFTFRTYA (SEQ ID NO: 9) | GFTFRTY (SEQ ID NO: 9) | AASGFTFRTYAMS (SEQ ID NO: 21) | GFTFRTYA (SEQ ID NO: 9) | GFTFRTY (SEQ ID NO: 4); | GFTFRT (SEQ ID NO: 9) | GFTFRT (SEQ ID NO: 4); |
|  | CDR2 | TIGSDRRHTY (SEQ ID NO: 13) | IGSDRRHT (SEQ ID NO: 10) | GSDRRH (SEQ ID NO: 5) | TIGSDRRHTY (SEQ ID NO: 13) | IGSDRRHT (SEQ ID NO: 10) | GSDRRH (SEQ ID NO: 5) | IGSDRRHT (SEQ ID NO: 10) | GSDRRH (SEQ ID NO: 5) |
|  | CDR3 | Not determined | Not determined | Not determined | Not determined | Not determined | Not determined | VGPYDGYYGEFDY (SEQ ID NO: 6) | VGPYDGYYGEFDY (SEQ ID NO: 6) |
| VH3 | CDR1 | KASGFTFRTYAMS (SEQ ID NO: 22) | GFTFRTYA (SEQ ID NO: 9) | GFTFRTY (SEQ ID NO: 4); | KASGFTFRTYAMS (SEQ ID NO: 22) | GFTFRTYA (SEQ ID NO: 9) | GFTFRTY (SEQ ID NO: 4); | GFTFRTYA (SEQ ID NO: 9) | GFTFRT (SEQ ID NO: 4); |
|  | CDR2 | TIGSDRRHTY (SEQ ID NO: 13) | IGSDRRHT (SEQ ID NO: 10) | GSDRRH (SEQ ID NO: 5) | TIGSDRRHTY (SEQ ID NO: 13) | IGSDRRHT (SEQ ID NO: 10) | GSDRRH (SEQ ID NO: 5) | IGSDRRHTY (SEQ ID NO: 23) | GSDRRH (SEQ ID NO: 5) |
|  | CDR3 | Not determined | Not determined | Not determined | Not determined | Not determined | Not determined | VGPYDGYYGEFDY (SEQ ID NO: 6) | VGPYDGYYGEFDY (SEQ ID NO: 6) |
| VL1 | CDR1 | RSSQSLLDSDGKTFLN (SEQ ID NO: 24) | QSLLDSDGKTF (SEQ ID NO: 7) | RSSQSLLDSDGKTFLN (SEQ ID NO: 24) | RSSQSLLDSDGKTFLN (SEQ ID NO: 24) | QSLLDSDGKTF (SEQ ID NO: 7) | RSSQSLLDSDGKTFLN (SEQ ID NO: 24) | QSLLDSGKTF (SEQ ID NO: 7) | QSLLDSGKTF (SEQ ID NO: 7) |
|  | CDR2 | YLVSKLDS (SEQ ID NO: 25) | LVS | LVSKLDS (SEQ ID NO: 26) | YLVSKLDS (SEQ ID NO: 25) | LVS | LVSKLDS (SEQ ID NO: 26) | LVS | LVS |
|  | CDR3 | WQGTHFPYT (SEQ ID NO: 11) | WGGTHFPYT (SEQ ID NO: 11) | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) |
| VL2 | CDR1 | RSSQSLLDSDGKTFLN (SEQ ID NO: 24) | QSLLDSDGKTF (SEQ ID NO: 7) | RSSQSLLDSDGKTFLN (SEQ ID NO: 24) | RSSQSLLDSDGKTFLN (SEQ ID NO: 24) | QSLLDSDGKTF (SEQ ID NO: 7) | RSSQSLLDSDGKTFLN (SEQ ID NO: 24) | QSLLDSGKTF (SEQ ID NO: 7) | QSLLDSGKTF (SEQ ID NO: 7) |
|  | CDR2 | YLVSKRDS (SEQ ID NO: 27) | LVS | LVSKRDS (SEQ ID NO: 28) | YLVSKRDS (SEQ ID NO: 27) | LVS | LVSKRDS (SEQ ID NO: 28) | LVS | LVS |
|  | CDR3 | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) |
| VL3 | CDR1 | KSSQSLLDSDGKTFLN (SEQ ID NO: 29) | QSLLDSDGKTF (SEQ ID NO: 7) | KSSQSLLDSDGKTFLN (SEQ ID NO: 29) | KSSQSLLDSDGKTFLN (SEQ ID NO: 29) | QSLLDSDGKTF (SEQ ID NO: 7) | KSSQSLLDSDGKTFLN (SEQ ID NO: 29) | QSLLDSDGKTF (SEQ ID NO: 7) | QSLLDSDGKTF (SEQ ID NO: 7) |
|  | CDR2 | YLVSKLDS (SEQ ID NO: 25) | LVS | LVSKLDS (SEQ ID NO: 26) | YLVSKLDS (SEQ ID NO: 25) | LVS | LVSKLDS (SEQ ID NO: 26) | LVS | LVS |

-continued

|     |      | 1 | 2 | 3 | 4 | 5 | 6 | 7 | 8 |
|-----|------|---|---|---|---|---|---|---|---|
|     | CDR3 | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) | WQGTHFPYT (SEQ ID NO: 11) |
| VH1 | CDR1 | AASGFTFSRYGMS (SEQ ID NO: 30) | GFTFSRYG (SEQ ID NO: 31) | GFTFSRY (SEQ ID NO: 16) | AASGFTFSRYGMS (SEQ ID NO: 30) | GFTFSRYG (SEQ ID NO: 31) | GFTFSRY (SEQ ID NO: 16) | GFTFSRYG (SEQ ID NO: 31) | SGFTFSRY (SEQ ID NO: 16) |
|     | CDR2 | TISSGGSYTY (SEQ ID NO: 32) | ISSGGSYT (SEQ ID NO: 33) | SSGGSY (SEQ ID NO: 17) | TISSGGSYTY (SEQ ID NO: 32) | ISSGGSYT (SEQ ID NO: 33) | SSGGSY (SEQ ID NO: 17) | ISSGGSYT (SEQ ID NO: 33) | SSGGSY (SEQ ID NO: 17) |
|     | CDR3 | Not determined | Not determined | Not determined | Not determined | Not determined | Not determined | ERHGGDGYWYFDV (SEQ ID NO: 34) | ERHGGDGYWYFDV (SEQ ID NO: 34) |
| VH2 | CDR1 | AASGFTFSRYGMS (SEQ ID NO: 30) | GFTFSRYG (SEQ ID NO: 31) | GFTFSRY (SEQ ID NO: 16) | AASGFTFSRYGMS (SEQ ID NO: 30) | GFTFSRYG (SEQ ID NO: 31) | GFTFSRY (SEQ ID NO: 16) | GFTFSRYG (SEQ ID NO: 31) | GFTFSRY (SEQ ID NO: 16) |
|     | CDR2 | TISSGGSYTY (SEQ ID NO: 32) | ISSGGSYT (SEQ ID NO: 33) | SSGGSY (SEQ ID NO: 17) | TISSGGSYTY (SEQ ID NO: 32) | ISSGGSYT (SEQ ID NO: 33) | SSGGSY (SEQ ID NO: 17) | ISSGGSYT (SEQ ID NO: 33) | SSGGSY (SEQ ID NO: 17) |
|     | CDR3 | Not determined | Not determined | Not determined | Not determined | Not determined | Not determined | ERHGGDGYWYFDV (SEQ ID NO: 34) | ERHGGDGYWYFDV (SEQ ID NO: 34) |
| VH3 | CDR1 | TASGFTFSRYGMS (SEQ ID NO: 35) | GFTFSRYG (SEQ ID NO: 31) | GFTFSRY (SEQ ID NO: 16) | TASGFTFSRYGMS (SEQ ID NO: 35) | GFTFSRYG (SEQ ID NO: 31) | GFTFSRY (SEQ ID NO: 16) | GFTFSRYG (SEQ ID NO: 31) | GFTFSRY (SEQ ID NO: 16) |
|     | CDR2 | TISSGGSYTY (SEQ ID NO: 32) | ISSGGSYT (SEQ ID NO: 33) | SSGGSY (SEQ ID NO: 17) | TISSGGSYTY (SEQ ID NO: 32) | ISSGGSYT (SEQ ID NO: 33) | SSGGSY (SEQ ID NO: 17) | ISSGGSYT (SEQ ID NO: 33) | SSGGSY (SEQ ID NO: 17) |
|     | CDR3 | Not determined | Not determined | Not determined | Not determined | Not determined | Not determined | ERHGGDGYWYFDV (SEQ ID NO: 34) | ERHGGDGYWYFDV (SEQ ID NO: 34) |
| VL1 | CDR1 | RASQDISNYLN (SEQ ID NO: 36) | QDISNY (SEQ ID NO: 18) | RASQDISNYLN (SEQ ID NO: 36) | RASQDISNYLN (SEQ ID NO: 36) | QDISNY (SEQ ID NO: 18) | RASQDISNYLN (SEQ ID NO: 36) | QDISNY (SEQ ID NO: 18) | QDISNY (SEQ ID NO: 18) |
|     | CDR2 | YYTSRLHS (SEQ ID NO: 37) | YTS | YTSRLHS (SEQ ID NO: 38) | YYTSRLHS (SEQ ID NO: 37) | YTS | YTSRLHS (SEQ ID NO: 38) | YTS | YTS |
|     | CDR3 | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) |
| VL2 | CDR1 | RASQDISNYLN (SEQ ID NO: 36) | QDISNY (SEQ ID NO: 18) | RASQDISNYLN (SEQ ID NO: 36) | RASQDISNYLN (SEQ ID NO: 36) | QDISNY (SEQ ID NO: 18) | RASQDISNYLN (SEQ ID NO: 36) | QDISNY (SEQ ID NO: 18) | QDISNY (SEQ ID NO: 18) |
|     | CDR2 | YYTSRLHS (SEQ ID NO: 37) | YTS | YTSRLHS (SEQ ID NO: 38) | YYTSRLHS (SEQ ID NO: 37) | YTS | YTSRLHS (SEQ ID NO: 38) | YTS | YTS |

-continued

|   |      | 1 | 2 | 3 | 4 | 5 | 6 | 7 | 8 |
|---|------|---|---|---|---|---|---|---|---|
|   | CDR3 | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) |
| VL3 | CDR1 | RASQDISNYLN (SEQ ID NO: 36) | QDISNY (SEQ ID NO: 18) | RASQDISNYLN (SEQ ID NO: 36) | RASQDISNYLN (SEQ ID NO: 36) | QDISNY (SEQ ID NO: 18) | RASQDISNYLN (SEQ ID NO: 36) | QDISNY (SEQ ID NO: 18) | QDISNY (SEQ ID NO: 18) |
|   | CDR2 | YYTSRLHS (SEQ ID NO: 37) | YTS | YTSRLHS (SEQ ID NO: 38) | YYTSRLHS (SEQ ID NO: 37) | YTS | YTSRLHS (SEQ ID NO: 38 | YTS | YTS |
|   | CDR3 | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) | QQGNPLRT (SEQ ID NO: 39) |

The antibodies or antigen binding fragments thereof can be selected from the group of Fab, F(ab')$_2$, Fab', scFv, or Fv.

Complementarity determining regions (CDRs) are part of the variable region of an antibody or a T cell receptor generated by B-cells and T-cells respectively, wherein these molecules bind to their specific antigen (also called epitope). In certain embodiments, the terms "variable region" and "variable domain" are used interchangeably, referring to the polypeptide of a light or heavy chain of an antibody that varies greatly in its sequence of amino acid residues from one antibody to another, and that determines the conformation of the combining site which confers the specificity of the antibody for a particular antigen. In a further embodiment, the variable region is about 90 amino acids long to about 200 amino acids long, including but not limited to about 100 amino acids long, or alternatively about 110 amino acids long, or alternatively about 120 amino acids long, or alternatively about 130 amino acids long, or alternatively about 140 amino acids long, or alternatively about 150 amino acids long, or alternatively about 160 amino acids long, or alternatively about 170 amino acids long, or alternatively about 180 amino acids long, or alternatively about 190 amino acids long. In certain embodiments, a variable region of an amino acid sequence, as used herein, refers to that the first about 100 amino acids, or alternatively about 110 amino acids, or alternatively about 120 amino acids, or alternatively about 130 amino acids, or alternatively about 140 amino acids, or alternatively about 150 amino acids of the amino acid sequence (including or excluding a signal peptide if applicable) is the variable region.

A set of CDRs constitutes a paratope also called an antigen-binding site, which is a part of an antibody that recognizes and binds to an antigen. There are three CDRs (CDR1, CDR2 and CDR3), arranged non-consecutively, optionally from the amino terminus to the carboxyl terminus, on the amino acid sequence of a variable region of an antigen receptor, such as a heavy chain or a light chain. As used herein, CDRn refers to a CDRn in an immunoglobulin chain or derived from an immunoglobulin chain, wherein the number n is selected from 1-3. In one embodiment, CDRLn refers to a CDRn in a light chain or derived from a light chain, wherein the number n is selected from 1-3; while CDRHn refers to a CDRn in a heavy chain or derived from a heavy chain, wherein the number n is selected from 1-3. In certain embodiments, framework region (FR) refers to the part of a variable region which is not a CDR. In certain embodiments, FRn refers to a FR in a heavy chain or a light chain or derived from a heavy chain or a light chain, and wherein the number n is selected from 1-4. In certain embodiments, a variable region comprises or consists essentially of, or yet further consists of the following (optionally following the order as provided, and further optionally from the amino terminus to the carboxyl terminus): FR1, CDR1, FR2, CDR2, FR3, CDR3 and FR4.

Variable regions and/or CDRs of an antibody or a fragment thereof can be determined by one of skill in the art, for example, using publically or commercially available tools. Non-limiting examples of such tools include, IgBlast (accessible at www.ncbi.nlm.nih.gov/igblast/), Scaligner (available from drugdesigntech at www.scaligner.com/), IMGT rules and/or tools (see, for example, www.imgt.org/IMGT-ScientificChart/Nomenclature/IMGT-FRCDRdefinition.html, also accessible at www.imgt.org/), Chothia Canonical Assignment (accessible at www.bioinf.org.uk/abs/chothia.html), Antigen receptor Numbering And Receptor CalssificatiIon (ANARCI, accessible at opig.stats.ox.ac.uk/webapps/newsabdab/sabpred/anarci/), the Kabat numbering method/scheme (e.g., Kabat, E. A., et al. (1991) Sequences of Proteins of Immunological Interest, Fifth Edition, U.S. Department of Health and Human Services, NIH Publication No. 91-3242,) or the Paratome web server (accessible at www.ofranlab.org/paratome/, see Vered Kunik, et al, Nucleic Acids Research, Volume 40, Issue W1, 1 Jul. 2012, Pages W521-W524).

The antibodies can be polyclonal, monoclonal, multispecific (e.g., bispecific antibodies), humanized or antibody fragments, so long as they exhibit the desired biological activity. Antibodies can be isolated from any suitable biological source, e.g., murine, rat, sheep and canine.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous sample of a specific monoclonal antibody. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies disclosed herein may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region or a fragment thereof (for example, 1, 2, 3, 4, 5, or all 6 CDRs) of the recipient are replaced by residues from a variable region or a fragment thereof (for example, 1, 2, 3, 4, 5, or all 6 CDRs) of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. Without wishing to be bound by the theory, humanized antibodies produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine. Specifically, the humanized antibodies as disclosed herein specifically binds to a DNABII polypeptide or a fragment thereof (such as the tip chimeric peptide or the tail chimeric peptide) with certain range(s) of one or more of the following: $EC_{50}$, $K_{on}$, $K_{off}$, $K_A$ and/or $K_D$, and inhibits or releases certain cytokine(s) upon treating a subject. In a further embodiment, the humanized antibody specifically binding to the tip region of a DNABII polypeptide (such as the tip chimeric peptide) disrupts biofilm both in vivo and in vitro. In addition, the process of humanization, while a rational design process, may produce unexpected changes (positive or negative) in e.g. binding affinity, antigen specificity, or physical properties such as solubility or aggregatability; hence, properties of humanized antibodies are not inherently predictable from the properties of the starting non-human antibody.

In one embodiment, an antibody as used herein may be a recombinant antibody. The term "recombinant antibody", as used herein, includes all antibodies that are prepared, expressed, created or isolated by recombinant means, such as antibodies isolated from an animal (e.g., a mouse) that is transgenic or transchromosomal for immunoglobulin genes or a hybridoma prepared therefrom, antibodies isolated from a host cell transformed to express the antibody, e.g., from a transfectoma, antibodies isolated from a recombinant, combinatorial antibody library, and antibodies prepared, expressed, created or isolated by any other means that involve splicing of immunoglobulin (Ig) gene sequences to other DNA sequences. In certain embodiments, however, such recombinant antibodies can be subjected to in vitro mutagenesis (or, when an animal transgenic for Ig sequences is used, in vivo somatic mutagenesis) and thus the amino acid sequences of the VH and VL regions of the recombinant antibodies are sequences that may not naturally exist within the antibody germline repertoire in vivo. Methods to making these antibodies are known in the art.

In one embodiment, an antibody as used herein may be a chimeric antibody. As used herein, chimeric antibodies are antibodies whose light and heavy chain genes have been constructed, typically by genetic engineering, from antibody variable and constant region genes belonging to different species.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals ($6^{th}$ ed). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Eukaryotic cells" comprise all of the life kingdoms except Monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 µm in diameter and 10 µm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" or "binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances which are immunogenic, i.e., immunogens, as well as substances which induce immunological unresponsiveness, or anergy, i.e., anergens.

"Immune response" broadly refers to the antigen-specific responses of lymphocytes to foreign substances. The terms "immunogen" and "immunogenic" refer to molecules with the capacity to elicit an immune response. All immunogens are antigens, however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

The term "passive immunity" refers to the transfer of immunity from one subject to another through the transfer of antibodies. Passive immunity may occur naturally, as when maternal antibodies are transferred to a fetus. Passive immunity may also occur artificially as when antibody compositions are administered to non-immune subjects. Antibody donors and recipients may be human or non-human subjects. Antibodies may be polyclonal or monoclonal, may be generated in vitro or in vivo, and may be purified, partially purified, or unpurified depending on the embodiment. In some embodiments described herein, passive immunity is conferred on a subject in need thereof through the administration of antibodies or antigen binding fragments that specifically recognize or bind to a particular antigen. In some embodiments, passive immunity is conferred through the administration of an isolated or recombinant polynucleotide encoding an antibody or antigen binding fragment that specifically recognizes or binds to a particular antigen.

In the context of this disclosure, a "ligand" is a polypeptide. In one aspect, the term "ligand" as used herein refers to any molecule that binds to a specific site on another molecule. In other words, the ligand confers the specificity of the protein in a reaction with an immune effector cell or an antibody to a protein or DNA to a protein. In one aspect it is the ligand site within the protein that combines directly with the complementary binding site on the immune effector cell.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, Calif.).

An example of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

As used herein, a biological sample, or a sample, can be obtained from a subject, cell line or cultured cell or tissue. Exemplary samples include, but are not limited to, cell sample, tissue sample, liquid samples such as blood and other liquid samples of biological origin (including, but not limited to, ocular fluids (aqueous and vitreous humor), peripheral blood, sera, plasma, ascites, urine, cerebrospinal fluid (CSF), sputum, saliva, bone marrow, synovial fluid, aqueous humor, amniotic fluid, cerumen, breast milk, bronchoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood. In one embodiment, the biological sample is suspect of having a biofilm. In another embodiment, the biological sample comprise a biofilm.

As used herein, the term "signal peptide" or "signal polypeptide" intends an amino acid sequence usually present at the N-terminal end of newly synthesized secretory or membrane polypeptides or proteins. It acts to direct the polypeptide to a specific cellular location, e.g. across a cell membrane, into a cell membrane, or into the nucleus. In some embodiments, the signal peptide is removed following localization. Examples of signal peptides are well known in the art. Non-limiting examples are those described in U.S. Pat. Nos. 8,853,381, 5,958,736, and 8,795,965.

As used herein, the term "$EC_{50}$" refers to the concentration of an antibody or a fragment thereof which induces a response (for example, binding between the antibody or a fragment thereof and its target) halfway between the baseline and maximum after a specified exposure time.

Several parameters are used herein to described the binding and unbinding reaction of receptor (R, such as an antibody or a fragment thereof) and ligand (L, such as the target of the antibody or a fragment thereof) molecules, which is formalized as: $R+L \rightleftharpoons RL$. The reaction is characterized by the on-rate constant $k_{on}$ and the off-rate constant $k_{off}$, which have units of $M^{-1} s^{-1}$ and $s^{-1}$, respectively. In equilibrium, the forward binding transition $R+L \rightarrow RL$ should be balanced by the backward unbinding transition $RL \rightarrow R+L$. That is $k_{on}[R][L]=k_{off}[RL]$ where [R], [L] and [RL] represent the concentration of unbound free receptors, the concentration of unbound free ligand and the concentration of receptor-ligand complexes. Further, the equilibrium dissociation constant "$K_D$" can be calculated as $k_{off}/k_{on}$ which is [R]×[L]/[RL], while the equilibrium association constant "$K_A$" can be calculated as $k_{on}/k_{off}$ which is [RL]/([R]×[L]).

As used herein, the term "anti-infective" refers to a medicine that is capable of inhibiting the spread of an infectious organism or by killing the infectious organism outright. This term encompasses, but is not limited to, antibiotics, antifungals, anthelmintics, antimalarials, antiprotozoals, antituberculosis agents, and antivirals. Antifungal agents are also called antimycotic agents. They kill or inactivate fungi and are used to treat fungal infections (including yeast infections). One non-limiting example, polyene antifungals are not absorbed when given orally, so are used to treat fungal infections of the gastrointestinal tract, such as oral thrush. Another non-limiting examples are azole antifungals which are synthetic, fungistatic agents with broad-spectrum activity, Echinocandins which are lipopeptide molecules that noncompetitively inhibit (1,3) beta-d-glucan synthase enzyme and target the fungal cell wall, Fulvicin U/F (i.e., griseofulvin), Grifulvin V (Pro) (i.e., griseofulvin), Lamisil (Pro) (i.e., terbinafine), Gris-PEG (Pro) (i.e., griseofulvin), Ancobon (Pro) (i.e., flucytosine), Fulvicin P/G (i.e., griseofulvin) and Terbinex (Pro) (i.e., terbinafine). More anti-infective agents can be found, for example, at www.drugbank.ca/categories/DBCAT000065. The term "anti-viral" or "antiviral" refers to a class of medication used for treating viral infections. Most antivirals target specific viruses, while a broad-spectrum antiviral is effective against a wide range of viruses. Unlike most antibiotics, antiviral drugs do not destroy their target pathogen; instead they inhibit their development. Some of the ways they may act include preventing viral replication by inhibiting viral DNA polymerase; binding to specific cell-surface receptors and inhibiting viral penetration or uncoating; inhibiting viral protein synthesis; or blocking late stages of virus assembly. Non-limiting examples of anti-viral agents can be found, for example, at www.drugbank.ca/categories/DBCAT000066.

As used herein, the term "anti-parasitic" refers to a class of medications which are indicated for the treatment of parasitic diseases, such as those caused by helminths, amoeba, ectoparasites, parasitic fungi, and protozoa, among others. Non-limiting examples of anti-parasitics can be found, for example, at www.drugbank.ca/categories/DBCAT000522.

The EC50 is the concentration of a drug that gives half-maximal response. The IC50 is the concentration of an inhibitor where the response (or binding) is reduced by half.

MIC refers to minimal inhibitory concentration of an active agent such as a drug that is the lowest concentration that will inhibit the visible growth of a microorganism after overnight incubation and minimal bactericidal concentrations as the lowest concentration of an antimicrobial that will prevent the growth of an organism after subculture on antibiotic free media. Methods to determine these values are well known in the art and describe in Andrews, J. (2002) Antimicrob Chemother June; 49(6):1049.

Modes for Carrying Out the Disclosure

In various embodiments, a sensitivity of a bacterium to a given antibiotic is used in determining protocols for using antibiotics to treat bacterial infections. Using antibiotics to more effectively treat bacterial infections applies a measure of the degree of sensitivity that a causative bacterium has to a given antibiotic. Confounding measurement is the fact that bacteria exist in different physiologic states with highly variable antibiotic sensitivities. Bacteria were previously thought to only exist in nature in 2 distinct states: planktonic and biofilm. The former is free living, while the latter exists in a community architecture where the bacteria are embedded in a self-made matrix with a common underlying structure of scaffolded extracellular DNA. Operationally, these two states can be distinguished by antibiotic sensitivities where biofilm-resident bacteria are typically 1000-fold (or greater) more resistant to antibiotics than the same bacteria in its planktonic state. Moreover, depending on how each state is grown will further elicit variation in antibiotic sensitivities.

Various embodiments of the disclosure may identify two additional but distinct physiologic states that may transiently exist. In the first newly described state, bacteria that are associated but not physically resident within the biofilm (Biofilm Non-Associated or BNA) are most likely to mimic the free-living state of native bacteria when compared to planktonic bacteria grown in vitro; sensitivity of BNA to killing by antibiotics vary from those grown planktonically. In the second newly described state, when bacteria are Newly Released (NRel) from biofilm residence they are operationally significantly more sensitive to antibiotics than even their planktonic counterparts. Various embodiments of the disclosure recognize: 1) Antibiotic sensitivities of BNA bacteria will more closely mimic the native bacteria derived from disease sequelae; 2) the NRel phenotype can be predicted by the rate at which the bacteria are released from biofilm residence regardless of the means of release [e.g. via an induced dispersion (bacterial programmed) or disruption (non-native release)]; 3) the NRel state can be described by changes in gene expression of a given bacterium upon release from a biofilm; increases or decreases of the expression of specific repertoires of bacterial genes indicative of NRel are definitive for specific antibiotic sensitivities. Thus, any disease causing bacterium whose virulence is dependent on the biofilm state can be better targeted for treatment with a combination of knowing the ground state of antibiotic sensitivities of BNA, a means to release those bacteria with known kinetics, and knowing that rate of release and or the changes in gene expression which occur upon release induction.

In various embodiments, one or more antibiotics may be selected for a chronic/recurrent infection resulting from a biofilm so as to reduce the dose and/or length of course of antibiotic treatment. For example, if a bacterial pathogen is determined to be sensitive to an antibiotic in its planktonic form but resistant to that antibiotic in its biofilm form, then the biofilm may be dispersed or disrupted from the biofilm residence in order to clear the infection. In various embodiments, a dispersal or disruption method and/or agent may be determined based at least in part on a rate of bacterial release from a biofilm that sensitizes the pathogen to a chosen antibiotic.

Various embodiments of the disclosed approach provide an enhanced, more accurate selection of antibiotics to be used to treat individuals with chronic or recurrent bacterial infections, for example, when used in conjunction with known biofilm dispersal or disruption techniques and/or agents.

Thus, in one aspect, provided herein is a method to identify antibiotic sensitivity of a bacteria released from a biofilm by pre-treatment with an agent that disrupts the biofilm, comprising contacting newly released bacteria (NRel bacteria) with a range of varying concentrations of one or more candidate agent(s) and determining the range of varying concentrations that inhibit the growth of NRel bacteria thereby identifying antibiotic sensitivity. Methods to contact the bacteria with the one or more candidate agent(s) to identify antibiotic sensitivity are known in the art and described herein. Using this information, MIC can be determined and used to modify dosage and treatment regimens for patients with pre-existing biofilms or at risk of developing a biofilm. The biofilm and bacteria can be from a clinical isolate, e.g., blood, sputum, wounds, cornea, tissue sample, and can be from a healthy or from a patient or subject with a biofilm infection, e.g., a cystic fibrosis patient. The subject can be a mammal, e.g., a canine, feline, bovine, equine or a human patient as appropriate. The biofilm also can grown in vitro, using the methods known in the art and as described herein.

The methods are useful to determine antibiotic sensitivity, MIC and patient dosing information for NRel that have been treated with one or more of an anti-DNABII or anti-PilA or anti-rsPilA antibody or a fragment thereof. Examples of such antibodies and fragments thereof are known in the art and described herein and include polyclonal as well as monoclonal antibodies. Non-limiting examples of such include anti-tip chimer antibodies, anti-IHF antibodies and fragments thereof.

In one aspect, antibiotic sensitivity is determined by a method that determines the concentration that kills from about 10% to about 50%, or alternative, from about 20% to about 40%, from about 20% to about 30%, from about 20% to about 50%, from about 10% to about 40%, from about 10% to about 30%, or at least 25%, or at least 30%, or at least 35%, or at least 50%, or at least 55%, or at least 60%, or at least 65%, of the NRel bacteria.

In another aspect, two or more agents that disrupt a biofilm can be combined. Alternatively or in addition, antibiotic sensitivity is determined for varying concentrations of more than one candidate agent. In a particular aspect, antibiotic sensitivity is determined for two candidate agents. In a further aspect, antibiotic sensitive is determined for two candidate agents and two agents that disrupt a biofilm. When more than one agent that inhibits a biofilm is combined with one or more candidate agents, various combinations and amounts should be tested. The agents that inhibit a biofilm and/or the candidate agents can be provided in a ratio of 1:1 to 1:10, or alternatively 1:2, or 1:3, or 1:4, or 1:5, or 1:6, or 1:7, or 1:8, or 1:9 or 1:10, or 1:11, or 1:12; 1:13 or more as non-limiting examples.

Biofilm forming bacteria are known in the art. Non-limiting examples for use in the disclosed method include a bacteria is selected from *Moraxella catarrhalis, Enterococcus faecium, Staphylococcus aureus, Klebsiella pneumoniae, Acinetobacter baumannii, Pseudomonas aeruginosa* or *Enterobacter* spp. As noted above, the biofilm can comprise a single or dual species biofilm. Examples of such dual species biofilms include those formed by a bacteria comprising one or more of *Aggregatibacter actinomycetemcomitans, Enterococcus faecium, Staphylococcus aureus, Klebsiella pneumoniae, Acinetobacter baumannii, Pseudomonas aeruginosa* or *Enterobacter* spp. In one aspect, the biofilm is formed by *Moraxella catarrhalis* and one or more of *Aggregatibacter actinomycetemcomitans, Enterococcus faecium, Staphylococcus aureus, Klebsiella pneumoniae, Acinetobacter baumannii, Pseudomonas aeruginosa* or *Enterobacter* spp.

Also as noted above, more than one candidate agent can be combined. In one aspect, the candidate agent comprises, or consists essentially of, or further consists of one or more of piperacillin, ceftazidime, sulfonamide, a β-lactam antibiotic, tobramycin, colisin, trimethoprim, sulfamethoxazole, clarithromycin, glutamate, ampicillin, amoxicillin, clavulanate or cefdinir. In one aspect, the two candidate are selected from glutamate and tobramycin, glutamate and colisin, trimethoprim and sulfamethoxazole, trimethoprim and clarithromycin, amoxicillin and clavulanate, or trimethoprim and sulfamethoxazole.

The timing of the release of the bacteria from the biofilm prior to use of the method can vary. In one aspect, the NRel bacteria are newly dispersed from the biofilm at least 5, or 10, or 30, or 45 minutes post by pre-treatment with the agent that disrupts the biofilm. In another aspect, the NRel bacteria are newly dispersed from the biofilm at least 1 or 2, or 3, 4, or 5, or 6, or 7, or 8, or 9 6 hours post by pre-treatment with the agent that disrupts the biofilm.

In another embodiment, the method further comprises identifying the minimal inhibitory concentration for the candidate agent or combination thereof. In a further aspect, the method further comprises performing transcriptional profiling of the NRel bacteria.

Based on this new information, this disclosure also provides administering the new effective amount of the antibiotic therapy to the subject or patient in need thereof, which will reduce toxicity and unnecessary side effects as a lower effective does is required. The method further comprises co-administration of the antibiotic and the agent that disrupts the biofilm before or concurrently with the antibiotic using methods known in the art. Any appropriate method of administration is used and will vary with the disease, the biofilm, the patient or subject and the location of the biofilm, e.g., inner ear versus in the lung. The agents can be combined with a carrier, such as a pharmaceutically acceptable carrier, for stabilization, storage and ease of administration. The subject can be a mammal, e.g., a canine, feline, murine, chinchilla, or human patient. When administered to an animal, they can be used for therapy or for pre-clinical studies.

In one aspect, provided herein is a method to inhibit the growth of a biofilm-forming bacteria in a biofilm comprising contacting the biofilm with an effective amount of an anti-PilA antibody or fragment thereof and an effective amount of trimethoprim and sulfamethoxazole (TMP/SMX) as determined using the MIC as determined herein. In another aspect, provided herein is a method to inhibit the growth of a biofilm-forming bacteria in a biofilm comprising contacting the biofilm with an effective amount of an anti-DNABII (e.g., anti-IHF) or fragment thereof and an effective amount of amoxicillin (AMC) or amoxicillin and clavulanate as determined using the MIC as determined herein. In another aspect, provided herein is a method to treat or prevent a disease or condition associated with a biofilm in a subject in need thereof by administering an effective amount of an anti-PilA antibody or fragment thereof and an effective amount of trimethoprim and sulfamethoxazole (TMP/SMX) as determined using the MIC as determined herein. In another aspect, provided herein is a method to inhibit the growth of a biofilm-forming bacteria in a biofilm comprising contacting the biofilm with an effective amount of an anti-DNABII (e.g., anti-IHF) or fragment thereof and an effective amount of amoxicillin (AMC) or amoxicillin and clavulanate as determined using the MIC as determined herein. In another aspect, provided herein is a method to inhibit the growth of a *P. aeruginosa* in a biofilm comprising contacting the biofilm with an effective amount of an anti-PilA antibody or fragment thereof and an effective amount of tobramycin as determined using the MIC as determined herein.

Non-limiting examples of the biofilm-forming bacteria include a bacteria is selected from *Moraxella catarrhalis, Enterococcus faecium, Staphylococcus aureus, Klebsiella pneumoniae, Acinetobacter baumannii, Pseudomonas aeruginosa* or *Enterobacter* spp. As noted above, the biofilm can comprise a single or dual species biofilm. Examples of such dual species biofilms include those formed by a bacteria comprising one or more of *Aggregatibacter actinomycetemcomitans, Enterococcus faecium, Staphylococcus aureus, Klebsiella pneumoniae, Acinetobacter baumannii, Pseudomonas aeruginosa* or *Enterobacter* spp. In one aspect, the biofilm is formed by *Moraxella catarrhalis* and one or more of *Aggregatibacter actinomycetemcomitans, Enterococcus faecium, Staphylococcus aureus, Klebsiella pneumoniae, Acinetobacter baumannii, Pseudomonas aeruginosa* or *Enterobacter* spp.

The contacting can be in vitro or in vivo.

In one aspect, provided herein is a method to inhibit the growth of a biofilm-forming bacteria in a subject or treat a disease caused by such or associated with a biofilm, (e.g., cystic fibrosis, dental caries and the like) comprising, or consisting essentially of, or yet further consisting of administering to the subject an effective amount of an anti-PilA antibody or fragment thereof and an effective amount of trimethoprim and sulfamethoxazole (TMP/SMX) as determined using the MIC as determined herein. In another aspect, provided herein is a method to inhibit the growth of a biofilm-forming bacteria in a biofilm in a subject or treat a disease caused by such comprising, or consisting essentially of, or yet further consisting of administering to the subject an effective amount of an anti-DNABII (e.g., anti-IHF) or fragment thereof and an effective amount of amoxicillin (AMC) or amoxicillin and clavulanate as determined using the MIC as determined herein. In another aspect, provided herein is a method to inhibit the growth of a *P. aeruginosa* in a biofilm in a subject or treat a disease caused by such comprising, or consisting essentially of, or yet further consisting of administering to the subject comprising administering to the subject an effective amount of an anti-PilA antibody or fragment thereof and an effective amount of tobramycin as determined using the MIC as determined herein. In one aspect, the disease is cystic fibrosis. Any appropriate method of administration is used and will vary with the disease, the biofilm, the patient or subject and the location of the biofilm, e.g., inner ear versus in the lung. The agents can be combined with a carrier, such as a pharmaceutically acceptable carrier, for stabilization, storage and ease of administration. The subject can be a mammal, e.g., a canine, feline, murine, chinchilla, or human patient. When administered to an animal, they can be used for therapy or for pre-clinical studies.

Non-limiting examples of the biofilm-forming bacteria include a bacteria is selected from *Moraxella catarrhalis, Enterococcus faecium, Staphylococcus aureus, Klebsiella pneumoniae, Acinetobacter baumannii, Pseudomonas aeruginosa* or *Enterobacter* spp. As noted above, the biofilm can comprise a single or dual species biofilm. Examples of such dual species biofilms include those formed by a bacteria comprising one or more of *Aggregatibacter actinomycetemcomitans, Enterococcus faecium, Staphylococcus aureus, Klebsiella pneumoniae, Acinetobacter baumannii, Pseudomonas aeruginosa* or *Enterobacter* spp. In one aspect, the biofilm is formed by *Moraxella catarrhalis* and one or more of *Aggregatibacter actinomycetemcomitans, Enterococcus faecium, Staphylococcus aureus, Klebsiella pneumoniae, Acinetobacter baumannii, Pseudomonas aeruginosa* or *Enterobacter* spp.

In one aspect, a device such as a sinus implant can be pre-treated with an anti-PilA or anti-DNABII antibody or fragment thereof and then the antibiotic administered in an effective amount, in some aspect determined to be at a dose below the MIC as previously determined. See Martyn et al. (2020) Larygoscope June 130(6):1364-1371.

The diseases and conditions related to a biofilm-forming bacterial infection are present in the upper, mid and lower airway (otitis, sinusitis, bronchitis but also exacerbations of chronic obstructive pulmonary disease (COPD), chronic cough, complications of and/or primary cause of cystic fibrosis (CF) and community acquired pneumonia (CAP). Thus, by practicing the in vivo methods disclosed herein, these diseases and complications from these infections can also be prevented or treated.

Infections might also occur in the oral cavity (caries, periodontitis) and caused by *Streptococcus mutans, Porphyromonas gingivalis, Aggregatibacter actinomvctemcomitans*. Infections might also be localized to the skin (abscesses, 'staph' infections, impetigo, secondary infection of burns, Lyme disease) and caused by *Staphylococcus aureus, Staphylococcus epidermidis, Pseudomonas aeruginosa* and *Borrelia burdorferi*. Infections of the urinary tract (UTI) can also be treated and are typically caused by *Escherichia coli*. Infections of the gastrointestinal tract (GI) (diarrhea, cholera, gall stones, gastric ulcers) are typically caused by *Salmonella enterica serovar, Vibrio cholerae* and *Helicobacter pylori*. Infections of the genital tract include and are typically caused by *Neisseria gonorrhoeae*. Infections can be of the bladder or of an indwelling device caused by *Enterococcus faecalis*. Infections associated with implanted prosthetic devices, such as artificial hip or knee replacements, or dental implants, or medical devices such as pumps, catheters, stents, or monitoring systems, typically caused by a variety of bacteria, can be treated by the methods disclosed herein. These devices can be coated or conjugated to an agent as described herein. Thus, by practicing the in vivo methods disclosed herein, these diseases and complications from these infections can also be prevented or treated.

Thus, routes of administration applicable to the methods disclosed herein include intranasal, intramuscular, urethrally, intratracheal, subcutaneous, intradermal, transdermal, topical application, intravenous, rectal, nasal, oral, inhalation, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery include systemic or localized routes. In general, routes of administration suitable for the methods disclosed herein include, but are not limited to, direct injection, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The agents disclosed herein can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

In various embodiments of the methods disclosed herein, the interfering agent will be administered by inhalation, injection or orally on a continuous, daily basis, at least once per day (QD), and in various embodiments two (BID), three (TID), or even four times a day. Typically, the therapeutically effective daily dose will be at least about 1 mg, or at least about 10 mg, or at least about 100 mg, or about 200 to about 500 mg, and sometimes, depending on the compound, up to as much as about 1 g to about 2.5 g.

Dosing of can be accomplished in accordance with the methods disclosed herein using capsules, tablets, oral suspension, suspension for intra-muscular injection, suspension for intravenous infusion, get or cream for topical application, or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In certain embodiments, compositions exhibit high therapeutic indices. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies (in certain embodiments, within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

Methods to determine if a disease or biofilm has been treated are known in the art and briefly described herein.

Kits containing the agents and instructions necessary to perform the in vitro and in vivo methods as described herein also are claimed. Accordingly, the disclosure provides kits for performing these methods which may include an antibody, antibody fragment, polypeptide, polynucleotide, vector or host cell, as well as instructions for carrying out the methods disclosed herein such as collecting tissue and/or performing the screen, and/or analyzing the results, and/or administration of an effective amount of an antibody, antibody fragment, polypeptide, polynucleotide, vector or host cell, as defined herein. These can be used alone or in combination with other suitable antimicrobial agents.

For example, a kit can comprise, or alternatively consist essentially of, or yet further consist of any one or more of agents identified above, e.g., antibody, antibody fragment, and antibiotic or drug. The kit can further comprise one or more of an adjuvant, an antigenic peptide or a carrier. Examples of carriers include a liquid carrier, a pharmaceutically acceptable carrier, a solid phase carrier, a pharmaceutically acceptable carrier, a pharmaceutically acceptable polymer, a liposome, a micelle, an implant, a stent, a paste, a gel, a dental implant, or a medical implant.

EXPERIMENTAL

Delivery of vaccines is the most cost-effective way to manage infectious diseases as these target prevention (Andre et al., 2008), and as such, vaccine development remains a viable and truly ideal goal. However, for those children and adults with existing biofilm-associated chronic or recurrent infections, an effective therapeutic approach is greatly needed. One target for this approach is the NTHI T4P, a critical adhesin with multiple roles in adherence, colonization, biofilm formation, twitching motility and competence (Bakaletz et al., 2005; Carruthers et al., 2012; Das et al., 2017; Jurcisek et al., 2007; Mokrzan et al., 2019; Mokrzan et al., 2016; Toone et al., 2020). Antibodies against the majority subunit of NTHI T4P (PilA), and specifically a recombinant and soluble form of PilA ('rsPilA'), induce dispersal of pre-existing NTHI as well as polymicrobial biofilms in vitro, and also those present within the middle ear in a chinchilla model of NTHI-induced OM wherein biofilm dispersal leads to rapid disease resolution. Examples of such antibodies are disclosed in Mokrzan et al., 2018; Novotny et al., 2009; Novotny et al., 2013b; Novotny et al., 2016; Novotny et al., 2015; Ysebaert et al., 2019).

Additional studies revealed an additional role for luxS quorum signaling specifically during biofilm dispersal induced by anti-rsPilA antibodies, which requires both NTHI T4P expression and luxS-induced production of AI-2. NTHI are released in a 'top down' process, with maximal dispersal into the supernatant within 6 h of incubation. Armbruster et al. also showed that *Moraxella catarrhalis*, which does not express AI-2, nonetheless "eavesdrops" on the AI-2 signal produced by NTHI within a polymicrobial biofilm formed by these two species, which leads to increased *M. catarrhalis* biofilm formation. Intriguingly, when Applicant incubated a pre-formed dual-species NTHI plus *M. catarrhalis* biofilm with antibody directed against rsPilA (to target an antigen expressed exclusively by NTHI), both NTHI and *M. catarrhalis* were dispersed from the biofilm. The mechanism for *M. catarrhalis* dispersal revealed another example wherein *M. catarrhalis* had eavesdropped on the AI-2 produced by NTHI in response to exposure to anti-rsPilA.

A second target, Integration Host Factor (IHF), is a critical structural element of the bacterial biofilm matrix. IHF and HU (a histone-like protein) comprise the ubiquitous two-membered DNABII family of bacterial DNA-binding proteins. Genes that encode IHF and/or HU are present in the genome of every member of Eubacteria (Kamashev et al., 2017). Hence, this target is not unique to NTHI but is instead species-independent due to its presence in all tested pathogen-formed biofilms to date, including each of the high priority ESKAPE pathogens (*Enterococcus faecium, Staphylococcus aureus, Klebsiella pneumoniae, Acinetobacter baumannii, Pseudomonas aeruginosa* and *Enterobacter* spp.) (Devaraj et al., 2018; Devaraj et al., 2015; Novotny et al., 2013a). Extracellular DNA (eDNA) and associated DNABII proteins are essential to the underlying architecture and structural integrity of these biofilms (Flemming and Wingender, 2010; Goodman et al., 2011; Jurcisek and Bakaletz, 2007; Whitchurch et al., 2002). Within the biofilm matrix, crossed strands of eDNA are stabilized by IHF and HU (Goodman et al., 2011). The result is a lattice-like eDNA scaffold that supports and maintains the biofilm architecture. Exposure of bacterial biofilms to antibody against DNABII proteins destabilizes the eDNA matrix and causes collapse of the biofilm structure (Goodman et al., 2011). The mechanism for this outcome is induction of an equilibrium shift wherein DNABII molecules in the milieu that surrounds the biofilm are sequestered due to formation of an antibody complex, thus DNABII proteins within the eDNA matrix are released (Brockson et al., 2014; Novotny et al., 2016). The result is a sudden, complete collapse of the eDNA scaffold and release of the biofilm-resident bacteria that begins within 3 min of exposure to anti-DNABII antibodies in vitro (Brockson et al., 2014; Novotny et al., 2019). Vaccination-induced antibodies against DNABII proteins disrupt pre-existing biofilms in a chinchilla model of NTHI-induced OM which permits clearance by host immune effectors (Goodman et al., 2011; Novotny et al., 2019; Novotny et al., 2016). Moreover, therapeutic treatment with anti-DNABII antibodies resolves osteolytic peri-implantitis in a rat model of pre-existing *Aggregatibacter actinomycetemcomitans* biofilms (Freire et al., 2017), and also eradicates aggregate biofilms of *P. aeruginosa* from the murine lung (Novotny et al., 2016).

Despite the fact that the mechanisms and kinetics of the two targeted antisera used here are very different, the outcome of exposure of NTHI biofilms to anti-rsPilA antibodies or anti-DNABII antibodies is release of NTHI from biofilm residence into the surrounding milieu.

Applicant used herein NTHI as a model organism to further characterize the phenotype of newly released bacteria, hereafter referred to as 'NRel'. Given the unique ways in which NTHI are released from biofilms by anti-rsPilA compared to anti-DNABII antibodies, a comparative analysis of abundances of all expressed proteins (as determined by quantitative mass spectrometry), targeted transcriptomics, flow cytometry and susceptibility to killing by a sulfonamide or β-lactam antibiotic was used to investigate whether anti-rsPilA induced NRel NTHI (Novotny et al., 2015) were phenotypically different than anti-DNABII induced NRel NTHI (Brockson et al., 2014), despite the genetic identity of these two populations.

The following examples are provided to illustrate but not limit the inventions as disclosed herein.

Experiment No. 1

Materials and Methods

Collection and Quantitation of NRel NTHI

Nontypeable *Haemophilus influenzae* strain 86-028NP is a clinical isolate that Applicant has maintained frozen at a low passage number since its recovery from the nasopharynx of a child undergoing tympanostomy tube insertion due to chronic otitis media (Harrison, A. et al., *J Bacteriol* 187, pgs. 4627-4636, (2005); Sirakova, T. et al., *Infect Immun* 62, 2002-2020 (1994)). NTHI biofilms were established in brain heart infusion broth supplemented with 2 µg each of β-Nicotinamide adenine dinucleotide (β-NAD) and heme per ml for 24 hr in 8-well chambered cover glass slides as described (Jurcisek, J. A., Dickson, *J Vis Exp*, doi: 10.3791/2481 (2011)). After 16 hr, biofilms were washed with 200 µl of equilibrated (37° C.) Dulbecco's phosphate buffered saline (DPBS).

To collect and enumerate NRels, NTHI biofilms were incubated with 5 µg rabbit polyclonal IgG derived from anti-native IHF antiserum (generated against IHF isolated from NTHI strain 86-028NP) 48 for 15 min ('anti-IHF NRels') or 11 µg rabbit polyclonal IgG derived from anti-rsPilA antiserum (generated against rsPilA designed to mimic the soluble portion of recombinant PilA expressed by NTHI strain 86-028NP) 28 for 6 hr ('anti-rsPilA NRels'). Rabbit polyclonal IgG derived from anti-NTHI OMP P5 or that isolated from naive rabbit serum served as negative controls. Rabbit polyclonal IgG was generated by passage of whole serum or antiserum through rProtein A Protein G GraviTrap columns per manufacturer's instructions (GE Healthcare Life Sciences). After incubation for either 15 min (anti-IHF NRels) or 6 h (anti-rsPilA NRels), 190 µl of medium was gently collected from each well, serially diluted and plated on chocolate agar to quantitate CFU NTHI.

Antibiotic Sensitivity of Biofilm-Resident, Planktonic, or NRel NTHI

Biofilms were established for 16 hr at 37° C. as described above. For biofilm-resident NTHI: biofilms were washed twice with DPBS and incubated in sBHI supplemented with the indicated antibiotics for at 37° C. 2 h. For planktonic NTHI: NTHI were incubated in sBHI for 3 hr as described above to reach log phase of growth, then diluted to the approximate concentration of either the anti-IHF ($2\times10^8$ CFU/ml) or anti-rsPilA NRels ($3\times10^8$ CFU/ml) to permit comparison between anti-IHF or anti-rsPilA NRels, (see FIG. 1). Planktonic NTHI were incubated with the indicated antibiotics at 37° C. for 2 hr. For NRel NTHI: anti-IHF or anti-rsPilA NRel, generated and collected as described above were incubated at 37° C. for 2 hr with the indicated antibiotics. CFU NTHI were determined by serial dilution and plating. Amoxicillin (Sigma-Aldrich, St. Louis, MO) and clavulanate (U.S. Pharmacopeia, Rockville, MD) were used at a ratio of 2:1. Trimethoprim (Sigma-Aldrich) and sulfamethoxazole (Santa Cruz Biotech, Dallas, TX) were used at a ratio of 1:5. For each antibiotic used, Applicant determined the concentration that killed approximately 20% of planktonic NTHI diluted to reproduce the bacterial density typical of anti-rsPilA or anti-IHF NRels (0.94/4.7 µg T/S or 2.5/1.25 µg A/C per ml for anti-rsPilA NRels and their planktonic or biofilm-resident counterparts; 0.05/0.25 µg T/S or 0.25/0.50 µg A/C per ml for anti-IHF NRels and their counterparts). All experiments were performed at least three times on separate days with two technical replicates for each treatment and control group.

Sample Preparation for LC-MS/MS

Anti-IHF and anti-rsPilA NRel NTHI were collected as described. Planktonic NTHI were incubated in sBHI for 3 hr to an OD490 of 0.65. Samples were centrifuged for 4 min at 13,200×rcf in an Eppendorf 5430 Microcentrifuge, resuspended in 1 ml DPBS and centrifuged again. Pellets were flash frozen in dry ice and 100% ethanol and stored at −80° C. All further processing was done by MS Bioworks LLC (Ann Arbor, MI).

Cell pellets were suspended in buffer (2% sodium dodecyl sulfate, 150 mM NaCl, 50 mM Tris pH 8), lysed with a sonic probe (Q Sonica, Newtown, CT) and heated at 100° C. for 10 min. Protein concentration of the extract was determined by Qubit fluorometry, and 10 μg of each sample was processed by SDS-PAGE using a 10% Bis Tris NuPage mini-gel (Invitrogen) in the MES buffer system. The migration windows (1 cm gel lane) were excised and digested in-gel with trypsin using a ProGest robot (DigiLab, Hopkinton, MA) with the following protocol: 1) wash with 25 mM ammonium bicarbonate followed by acetonitrile; 2) reduce with 10 mM dithiothreitol at 60° C. followed by alkylation with 50 mM iodoacetamide at room temperature; 3) digest with trypsin (Promega, Madison, WI) at 37° C. for 4 h; 4) quench with formic acid. Supernatants were analyzed directly without further processing.

Mass Spectrometry

Half of each pooled fraction was analyzed by nano LC-MS/MS with a Waters M-Class HPLC system interfaced to a ThermoFisher Fusion Lumos mass spectrometer. Peptides were loaded on a trapping column and eluted over a 75 μm analytical column at 350 nL/min; both columns were packed with Luna C18 resin (Phenomenex, Torrance, CA). The mass spectrometer was operated in data-dependent mode, with MS and MS-MS performed in the Orbitrap at 60,000 FWHM (full width at half maximum) resolution and 15,000 FWHM resolution, respectively. The instrument was run with a 3 s cycle for MS and MS/MS. Two hours of instrument time was employed for the analysis of each sample.

Mass Spectrometry Data Processing

Data were searched using a local copy of Mascot (Matrix Science) with the following parameters: enzyme, trypsin/P; database, https://www.ncbi.nlm.nih.gov/nuccore/CP000057.2 (concatenated forward and reverse plus common contaminants); fixed modifications, carbamidomethyl (C); variable modifications: acetyl (N-term), deamidation (N,Q), oxidation (M), pyro-glu (N-term Q); mass values, monoisotopic; peptide mass tolerance, 10 ppm; fragment mass tolerance, 0.02 Da; maximum missed cleavages, (Flemming, H. C., *Nat Rev Microbiol* 8, 623-633, doi: 10.1038/nrmicro2415 (2010)). Mascot DAT files were parsed into Scaffold (Proteome Software) for validation, filtering and to create a non-redundant list per sample. Data were filtered using at 1% protein and peptide false discovery rate (FDR), requiring at least two unique peptides per protein. Applicant used the normalized spectral counts for downstream analysis. To evaluate the variation and reproducibility in the replicates, Applicant generated the PCA plot with 95% confidence ellipses surrounding each population (using the FactoMineR and ggplot2 packages in R), with the normalized spectral counts for each protein identified by mass spectrometry in the three samples of planktonic, anti-rsPilA, and anti-IHF groups (FIG. 2A) (Lê, S., *Journal of Statistical Software* 25, 1-18, doi:10.18637/jss.v025.i01 (2008); Wickham, H. et al., *Elegant Graphics for Data Analysis*. (Springer-Verlag, New York, 2016)).

Differential Expression Analysis

With the normalized spectral counts from three biological replicates of the three sample groups: planktonic, anti-IHF NRel, anti-rsPilA NRel, were used for pairwise comparisons, to determine the differential expression of each protein using a two-tailed t-test. The P-values, Benjamini-Hochberg adjusted P-values, and fold changes were determined (Table 2). Proteins with >1.5-fold increase or decrease and with an associated P<0.05 were considered to have significantly difference in expression. Annotation of proteins by Clusters of Orthologous protein Groups of proteins from NTHI strain 86-028NP was used as published by (Tatusov, R. L., *Nucleic Acids Res* 28, 33-36, doi: 10.1093/nar/28.1.33 (2000); Aziz, A. et al., *Front Microbiol* 10, 1622, doi: 10.3389/fmicb.2019.01622 (2019)).

Statistics

Data are expressed as mean±SEM of at least three biological replicates performed on separate days with two technical replicates per sample. Statistical analyses were performed with GraphPad (Prism) software version 8.2. Multiple comparisons were made by one-way analysis of variance with the Holm-Sidak correction. All other comparisons were made with student's t-test. Comparisons of fold changes in normalized spectral counts of proteins identified by mass spectrometry and generation principal component analysis were performed in R (Bioconductor).

TABLE 1

Differences between mechanisms of NTHI release from biofilm-residence to the NRel state as mediated by anti-rsPilA or anti-IHF.

|  | anti-rsPilA | anti-IHF |
|---|---|---|
| Antigen location | NTHI surface [22] | Biofilm structural linchpin [39] |
| NTHI contribution | Active-native/programmed [30] | Passive-artificially induced |
| Release speed | Slow [30] | Fast [41] |
| Release mode | Top-down [30] | All at once [48] |
| NTHI-specific antigen? | Yes | No, species-agnostic [39] |
| Term used to define release from biofilm | Dispersal | Disruption |

TABLE 2

Summary of proteins with significant (P < 0.05) 1.5-fold increase or decrease in abundance of NRel versus planktonically grown NTHI or anti-IHF versus anti-rsPilA comparisons.

| COG category* | Protein† | Function† | Acc. No. ᵟ | Fc‡ |
|---|---|---|---|---|
| anti-rsPilA NRel/Planktonic | | | | |
| Energy production & conversion | ᵠTrxA | thioredoxin-like protein | AAX88118.1 | 5.1 |
|  | LctP | putative L-lactate permease | AAX88216.1 | 3.4 |
|  | NdhA | NADH dehydrogenase | AAX87796.1 | 1.9 |
|  | LldD | L-lactate dehydrogenase | AAX88789.1 | 1.8 |
|  | FumC | fumarate hydratase class II | AAX88535.1 | −1.6 |

TABLE 2-continued

Summary of proteins with significant (P < 0.05) 1.5-fold increase or decrease in abundance of NRel versus planktonically grown NTHI or anti-IHF versus anti-rsPilA comparisons.

| COG category* | Protein† | Function† | Acc. No.δ | Fc‡ |
|---|---|---|---|---|
| | GpsA | glycerol-3-phosphate dehydrogenase | AAX87756.1 | −1.7 |
| | φDsbE | thiol:disulfide interchange protein | AAX88104.1 | −2.3 |
| | NrfC | Fe-S-cluster-containing hydrogenase component 1 | AAX88077.1 | −2.3 |
| | PpC | phosphoenolpyruvate carboxylase | AAX88226.1 | −2.5 |
| | NapA | periplasmic nitrate reductase | AAX87401.1 | −3.8 |
| | GlpC | anaerobic glycerol-3-phosphate dehydrogenase subunit C | AAX87714.1 | −4.0 |
| | GlpA | anaerobic glycerol-3-phosphate dehydrogenase subunit A | AAX87716.1 | −4.1 |
| Amino acid transport & metabolism | TrpC | tryptophan biosynthesis protein TrpCF | AAX88545.1 | 12.5 |
| | δHisJ | probable amino-acid ABC transporter binding protein cystine import | AAX88089.1 | 2.3 |
| | TrpD | anthranilate phosphoribosyltransferase | AAX88546.1 | 2.2 |
| | TrpA | tryptophan synthase alpha chain | AAX88491.1 | 1.9 |
| | TrpB | tryptophan synthase beta chain | AAX88492.1 | 1.8 |
| | NifS2 | cysteine desulfurase | AAX87433.1 | 1.6 |
| | NTHI1208 | Transglutaminase-like enzyme, putative cysteine protease | AAX88062.1 | 1.6 |
| | AroK | shikimate kinase | AAX87264.1 | −1.5 |
| | ThrB | homoserine kinase | AAX87151.1 | −1.9 |
| | PepT | peptidase T | AAX88589.1 | −2.0 |
| | GlpB | anaerobic glycerol-3-phosphate dehydrogenase subunit B | AAX87715.1 | −3.5 |
| Inorganic ion transport & metabolism | Tbp1 | transferrin-binding protein 1 | AAX88031.1 | 9.4 |
| | HfeB | putative ABC-type chelated iron transport system, ATPase component | AAX87416.1 | 2.4 |
| | TehB | tellurite resistance protein | AAX88653.1 | 2.3 |
| | HxuC | heme/hemopexin-binding protein C | AAX87321.1 | 2.1 |
| | HfeA | putative periplasmic chelated iron binding protein | AAX87417.1 | 2.1 |
| | HitA | iron-utilization periplasmic protein | AAX87160.1 | 1.9 |
| | HktE | catalase | AAX87967.1 | 1.8 |
| | SodA | [Mn] superoxide dismutase | AAX88097.1 | 1.7 |
| | FtnB | ferritin like protein 2 | AAX88550.1 | −1.7 |
| | NrfA | cytochrome c552 | AAX88079.1 | −8.1 |
| | NrfB | cytochrome c-type protein | AAX88078.1 | −9.9 |
| Posttranslational modification, protein turnover, chaperones | φTrxA | thioredoxin-like protein | AAX88118.1 | 5.1 |
| | PdgX | peroxiredoxin/glutaredoxin | AAX87624.1 | 2.0 |
| | ClpB | ATP-dependent chaperone | AAX87905.1 | 1.7 |
| | OrfG | conserved hypothetical 21.9 kD protein in locus involved in transformation | AAX87485.1 | 1.6 |
| | RadA | DNA repair protein RadA homolog | AAX88271.1 | −1.8 |
| | φDsbE | thiol:disulfide interchange protein | AAX88104.1 | −2.3 |
| | CcmA | heme exporter protein A | AAX88098.1 | −2.7 |
| Cell envelope biogenesis | LpxC | UDP-3-O-[3-hydroxymyristoyl] N-acetylglucosamine deacetylase | AAX88145.1 | 2.3 |
| | LpsA | lipooligosaccharide glycosyl transferase | AAX87813.1 | −1.5 |
| | FtsI | peptidoglycan synthetase | AAX88133.1 | −3.3 |
| | TolA | cell envelope integrity inner membrane protein | AAX87438.1 | −4.0 |
| Coenzyme metabolism | NTHI0175 | conserved hypothetical protein SAM-dependent methyltransferase | AAX87158.1 | 3.6 |
| | PdxH | pyridoxamine 5'-phosphate oxidase | AAX87909.1 | −1.6 |
| | MenC | O-succinylbenzoate synthase | AAX88008.1 | −2.7 |
| DNA replication, recombination, & repair | RecN | DNA repair protein | AAX87073.1 | 1.7 |
| | UvrB | UvrABC system protein B | AAX88673.1 | −1.6 |
| Translation, ribosomal structure & biogenesis | RbfA | ribosome-binding factor A | AAX88605.1 | 1.5 |

TABLE 2-continued

Summary of proteins with significant (P < 0.05) 1.5-fold increase or decrease in abundance of NRel versus planktonically grown NTHI or anti-IHF versus anti-rsPilA comparisons.

| COG category* | Protein† | Function† | Acc. No. δ | Fc‡ |
|---|---|---|---|---|
| Transcription | PrfB | peptide chain release factor 2 | AAX88210.1 | −1.8 |
| | AsnC | regulatory protein AsnC | AAX87611.1 | 1.6 |
| | Sxy | DNA transformation protein TfoX | AAX87644.1 | −1.8 |
| Nucleotide transport & metabolism | CyaA | Adenylate cyclase | AAX87755.1 | 2.3 |
| Signal transduction | ᵠHisJ | probable amino-acid ABC transporter binding protein cystine import | AAX88089.1 | 2.3 |
| Intracellular trafficking | ExbD | transport protein | AAX87311.1 | 2.1 |
| General function prediction only | NTHI1703 | conserved hypothetical oxidoreductase | AAX88493.1 | 1.9 |
| | Hfq | host factor-I protein Hfq | AAX87465.1 | −1.7 |
| | NTHI0732 | predicted hydrolase of the HAD superfamily | AAX87648.1 | −1.9 |
| | NTHI0053 | conserved hypothetical protein | AAX87048.1 | −1.9 |
| | NTHI0249 | conserved hypothetical protein | AAX87219.1 | −1.9 |
| Function unknown | NTHI1214 | conserved putative gamma-carboxymuconolactone decarboxylase subunit | AAX88067.1 | 1.7 |
| | NTHI1503 | hypothetical protein | AAX88314.1 | −1.6 |
| | NTHI0349 | conserved hypothetical protein anti-IHF NRel/Planktonic | AAX87303.1 | −4.8 |
| Translation, ribosomal structure & biogenesis | RpsQ | 30S ribosomal protein S17 | AAX87834.1 | 2.8 |
| | NTHI0364 | conserved hypothetical protein ribosome-associated inhibitor A | AAX87316.1 | 2.0 |
| | RpmE | 50S ribosomal protein L31 | AAX87806.1 | 1.9 |
| | RpsT | 30S ribosomal protein S20 | AAX88005.1 | 1.8 |
| | RpsJ | 30S ribosomal protein S10 | AAX87824.1 | 1.7 |
| | RplO | 50S ribosomal protein L15 | AAX87845.1 | 1.6 |
| | RplU | 50S ribosomal protein L21 | AAX87919.1 | 1.6 |
| | RpsE | 30S ribosomal protein SS | AAX87843.1 | 1.6 |
| | RpsL | 30S ribosomal protein S12 | AAX87659.1 | 1.6 |
| | InfB | translation initiation factor IF-2 | AAX88610.1 | −1.6 |
| | RplW | 50S ribosomal protein L23 | AAX87827.1 | −2.0 |
| | InfA | translation initiation factor IF-1 | AAX87597.1 | −4.9 |
| | TruA | tRNA pseudouridine synthase A | AAX88218.1 | −5.7 |
| | PhoB | phosphate regulon transcriptional regulatory protein | AAX88556.1 | −5.8 |
| Inorganic ion transport & metabolism | HktE | catalase | AAX87967.1 | 2.0 |
| | HgpB | hemoglobin-haptoglobin binding protein B | AAX87692.1 | 2.0 |
| | HfeB | putative ABC-type chelated iron transport system, ATPase component | AAX87416.1 | 2.0 |
| | HfeA | putative periplasmic chelated iron binding protein | AAX87417.1 | 1.9 |
| | ZnuA | high-affinity zinc uptake system protein | AAX87184.1 | 1.6 |
| | TehB | tellurite resistance protein | AAX88653.1 | 1.5 |
| | CitT | citrate/succinate antiporter | AAX87023.1 | −1.7 |
| | Fur | ferric uptake regulation protein | AAX87247.1 | −1.7 |
| | NTHI1439 | conserved hypothetical phosphate transport regulator | AAX88259.1 | −1.8 |
| | NrfB | cytochrome c-type protein | AAX88078.1 | −2.4 |
| | NrfA | cytochrome c552 | AAX88079.1 | −2.7 |
| Posttranslational modification, protein turnover, chaperones | ᵠCydD | hypothetical ABC transporter, ATP-binding protein | AAX87693.1 | 2.4 |
| | PdgX | peroxiredoxin/glutaredoxin | AAX87624.1 | 1.8 |
| | GroES | 10 kDa chaperonin | AAX87591.1 | 1.8 |
| | TrxA | Thioredoxin | AAX87086.1 | 1.7 |
| | ClpB | ATP-dependent chaperone | AAX87905.1 | 1.6 |
| | DjlA | DnaJ-like protein | AAX87329.1 | −1.8 |
| | PpiB | peptidyl-prolyl cis-trans isomerase B | AAX87081.1 | −1.9 |
| | ᵠUreG | urease accessory protein UreG | AAX87585.1 | −2.0 |
| | ᵠDsbE | thiol:disulfide interchange protein | AAX88104.1 | −7.8 |

TABLE 2-continued

Summary of proteins with significant (P < 0.05) 1.5-fold increase or decrease in abundance of NRel versus planktonically grown NTHI or anti-IHF versus anti-rsPilA comparisons.

| COG category* | Protein† | Function† | Acc. No.δ | Fc‡ |
|---|---|---|---|---|
| Energy production & conversion | LctP | putative L-lactate permease | AAX88216.1 | 2.8 |
| | φCydD | hypothetical ABC transporter, ATP-binding protein | AAX87693.1 | 2.4 |
| | DlD | D-lactate dehydrogenase | AAX88704.1 | 2.1 |
| | PpC | phosphoenolpyruvate carboxylase | AAX88226.1 | −1.9 |
| | GlpA | anaerobic glycerol-3-phosphate dehydrogenase subunit A | AAX87716.1 | −2.0 |
| | FdhX | formate dehydrogenase major subunit | AAX87009.1 | −2.1 |
| | AtpH | ATP synthase delta chain | AAX87536.1 | −2.2 |
| | CitD | citrate lyase acyl carrier protein | AAX87027.1 | −3.3 |
| | φDsbE | thiol:disulfide interchange protein | AAX88104.1 | −7.8 |
| Cell envelope biogenesis | TonB | Periplasmic protein TonB, links inner and outer membrane | AAX87310.1 | 2.0 |
| | Pal | outer membrane protein P6 precursor | AAX87436.1 | 1.6 |
| | OmpP2 | outer membrane protein P2 precursor | AAX87199.1 | 1.5 |
| | LicC | phosphocholine cytidylyltransferase | AAX88398.1 | −1.8 |
| | LolA | outer-membrane lipoproteins carrier protein precursor | AAX88274.1 | −2.0 |
| | FtsI | peptidoglycan synthetase | AAX88133.1 | −3.0 |
| | Lic2A | UDP-Gal--lipooligosaccharide galactosyltransferase | AAX87599.1 | −3.0 |
| | LicD | phosphorylcholine transferase | AAX88397.1 | −5.7 |
| | NTHI1085 | predicted membrane bound zinc metalloprotease with PDZ domain | AAX87956.1 | −6.0 |
| Amino acid transport & metabolism | φHisJ | probable amino-acid ABC transporter binding protein cystine import | AAX88089.1 | 1.7 |
| | NTHI1208 | conserved hypothetical protein Transglutaminase-like enzyme, putative cysteine protease | AAX88062.1 | 1.5 |
| | OppF | oligopeptide transport ATP-binding protein | AAX88123.1 | −1.8 |
| | GlpB | anaerobic glycerol-3-phosphate dehydrogenase subunit B | AAX87715.1 | −2.0 |
| | AroK | shikimate kinase | AAX87264.1 | −2.2 |
| | ArtP | arginine transport ATP-binding protein | AAX88179.1 | −3.5 |
| | AroE | shikimate 5-dehydrogenase | AAX87686.1 | −8.7 |
| Coenzyme metabolism | BioB | Biotin synthase | AAX88047.1 | −1.6 |
| | RibA | GTP cyclohydrolase II | AAX87269.1 | −2.0 |
| | PdxH | pyridoxamine 5'-phosphate oxidase | AAX87909.1 | −2.6 |
| | CoaD | phosphopantetheine adenylyltransferase | AAX87681.1 | −3.7 |
| | menC | O-succinylbenzoate synthase | AAX88008.1 | −4.3 |
| | BioF | 8-amino-7-oxononanoate synthase | AAX88384.1 | −5.3 |
| DNA replication, recombination, & repair | RecN | DNA repair protein | AAX87073.1 | 1.9 |
| | PolA | DNA polymerase I | AAX87902.1 | −1.7 |
| | DnaE | DNA polymerase III alpha subunit | AAX87791.1 | −2.0 |
| | RelB | DNA-damage-inducible protein J, negative regulator of translation | AAX87739.1 | −5.3 |
| | DnaQ | DNA polymerase III, epsilon chain | AAX87197.1 | −5.8 |
| Transcription | φUreG | urease accessory protein UreG | AAX87585.1 | −2.0 |
| | RpoZ | DNA-directed RNA polymerase omega chain | AAX88793.1 | −2.1 |
| | GreA | transcription elongation factor GreA | AAX88453.1 | −2.2 |
| | RpoE | RNA polymerase sigma-E factor | AAX87635.1 | −3.3 |
| Lipid metabolism | PlsC | 1-acyl-sn-glycerol-3-phosphate acyltransferase | AAX87785.1 | −1.8 |
| | TesB | Acyl-CoA thioesterase II | AAX87079.1 | −4.5 |
| | IspD | 2-C-methyl-D-erythritol 4-phosphate cytidylyltransferase | AAX87703.1 | −5.0 |
| | IspF | 2-C-methyl-D-erythritol 2,4-cyclodiphosphate synthase | AAX87702.1 | −8.7 |
| Signal transduction | φHisJ | probable amino-acid ABC transporter binding protein cystine import | AAX88089.1 | 1.7 |
| | NTHI1437 | conserved hypothetical protein, SH3 domain | AAX88257.1 | −2.3 |
| | DksA | DnaK suppressor protein | AAX87065.1 | −3.3 |
| | RseA | sigma-E factor negative regulatory protein homolog | AAX87634.1 | −6.5 |

TABLE 2-continued

Summary of proteins with significant (P < 0.05) 1.5-fold increase or decrease in abundance of NRel versus planktonically grown NTHI or anti-IHF versus anti-rsPilA comparisons.

| COG category* | Protein† | Function† | Acc. No.δ | Fc‡ |
|---|---|---|---|---|
| Intracellular trafficking & secretion | ExbD | transport protein | AAX87311.1 | 2.3 |
|  | TolB | Tol-Pal system protein TolB | AAX87437.1 | 1.7 |
| Cell division & chromosome partitioning | FtsE | cell division ATP-binding protein | AAX87817.1 | −3.6 |
| General function prediction only | NTHI0052 | conserved hypothetical FtsH-interacting integral membrane protein | AAX87047.1 | 5.2 |
|  | NTHI0043 | conserved hypothetical membrane protein | AAX87038.1 | 1.6 |
|  | NTHI1199 | predicted ATPase | AAX88055.1 | −1.7 |
|  | UuaP | ABC transporter ATP-binding protein | AAX88594.1 | −1.8 |
|  | Hfq | host factor-I protein Hfq | AAX87465.1 | −1.8 |
|  | AbgA | aminobenzoyl-glutamate utilization protein A | AAX87654.1 | −1.9 |
|  | NTHI1590 | putative NAD(P)H oxidoreductase | AAX88393.1 | −2.0 |
|  | NTHI0779 | probable ABC transporter, ATP-binding protein | AAX87689.1 | −2.5 |
| Function unknown | NTHI0053 | conserved hypothetical protein | AAX87048.1 | −7.0 |
|  | NTHI0490 | conserved hypothetical protein Putative negative regulator of RcsB-dependent stress response | AAX87425.1 | −1.6 |
|  | NTHI0820 | conserved hypothetical protein Autotransporter translocation and assembly factor TamB | AAX87724.1 | −1.7 |
|  | NTHI0487 | conserved hypothetical transcriptional regulator with an N-terminal xre-type HTH domain | AAX87422.1 | −2.1 |
|  | NTHI0555 | conserved hypothetical protein | AAX87483.1 | −3.4 |
|  | NTHI1025 | conserved hypothetical protein Cell division protein ZapA | AAX87903.1 | −3.5 |
|  | NTHI0436 | conserved hypothetical protein isoprenylcysteine carboxyl methyltransferase | AAX87377.1 | −5.1 |
|  | NTHI1748 | conserved hypothetical protein Chalcone isomerase-like | AAX88534.1 | −5.2 |
|  | NTHI0319 | conserved hypothetical protein membrane protein YkgB | AAX87278.1 | −10.2 | anti-IHF NRel/anti-rsPilA NRel

| COG category* | Protein† | Function† | Acc. No.δ | Fc‡ |
|---|---|---|---|---|
| Translation, ribosomal structure & biogenesis | φDeaD | Cold-shock DEAD-box protein A homolog | AAX87292.1 | 2.2 |
|  | RpsT | 30S ribosomal protein S20 | AAX88005.1 | 1.9 |
|  | NTHI1369 | putative translation factor, SUA5 | AAX88196.1 | 1.9 |
|  | RpsQ | 30S ribosomal protein S17 | AAX87834.1 | 1.8 |
|  | RplU | 50S ribosomal protein L21 | AAX87919.1 | 1.6 |
|  | RpsE | 30S ribosomal protein S5 | AAX87843.1 | 1.5 |
|  | RpsL | 30S ribosomal protein S12 | AAX87659.1 | 1.5 |
|  | InfA | translation initiation factor IF-1 | AAX87597.1 | −5.5 |
|  | PhoB | phosphate regulon transcriptional regulatory protein | AAX88556.1 | −5.5 |
| Cell envelope biogenesis | MurB | UDP-N-acetylenolpyruvoylglucosamine reductase | AAX87327.1 | 1.9 |
|  | Pal | outer membrane protein P6 precursor | AAX87436.1 | 1.6 |
|  | NTHI0291 | putative small-conductance mechanosensitive channel: potassium efflux protein KefA | AAX87252.1 | −1.5 |
|  | LicD | phosphorylcholine transferase | AAX88397.1 | −4.8 |
| Transcription | φDeaD | Cold-shock DEAD-box protein A homolog | AAX87292.1 | 2.2 |
|  | GreA | transcription elongation factor GreA | AAX88453.1 | −2.2 |
|  | AsnC | regulatory protein AsnC | AAX87611.1 | −1.6 |
| DNA replication, recombination, & repair | φDeaD | Cold-shock DEAD-box protein A homolog | AAX87292.1 | 2.2 |
|  | RelB | DNA-damage-inducible protein J, negative regulator of translation | AAX87739.1 | −4.9 |
|  | UnG | uracil-DNA glycosylase | AAX87021.1 | −4.9 |

TABLE 2-continued

Summary of proteins with significant (P < 0.05) 1.5-fold increase or decrease in abundance of NRel versus planktonically grown NTHI or anti-IHF versus anti-rsPilA comparisons.

| COG category* | Protein† | Function† | Acc. No.⁸ | Fc‡ |
|---|---|---|---|---|
| Inorganic ion transport & metabolism | NrfA | cytochrome c552 | AAX88079.1 | 3.0 |
| | TehB | tellurite resistance protein | AAX88653.1 | −1.5 |
| | HugZ | putative heme iron utilization protein | AAX87900.1 | −1.9 |
| Energy production & conversion | ΨCydD | hypothetical ABC transporter, ATP-binding protein | AAX87693.1 | 3.6 |
| | GlpC | anaerobic glycerol-3-phosphate dehydrogenase subunit C | AAX87714.1 | 2.8 |
| | DmsB | anaerobic dimethyl sulfoxide reductase chain B | AAX88060.1 | 1.5 |
| Posttranslational modification, protein turnover, chaperones | ΨCydD | hypothetical ABC transporter, ATP-binding protein | AAX87693.1 | 3.6 |
| | DjlA | DnaJ-like protein | AAX87329.1 | −2.0 |
| Lipid metabolism | PlsC | 1-acyl-sn-glycerol-3-phosphate acyltransferase | AAX87785.1 | −1.9 |
| | IspF | 2-C-methyl-D-erythritol 2,4-cyclodiphosphate synthase | AAX87702.1 | −8.6 |
| Coenzyme metabolism | PanF | sodium/pantothenate symporter | AAX88013.1 | −1.5 |
| | RibA | GTP cyclohydrolase II | AAX87269.1 | −2.1 |
| | CoaD | phosphopantetheine adenylyltransferase | AAX87681.1 | −3.2 |
| Nucleotide transport & metabolism | GmK | guanylate kinase | AAX88794.1 | −1.5 |
| | CmK | cytidylate kinase | AAX87701.1 | −2.0 |
| | PurU | formyltetrahydrofolate deformylase | AAX88279.1 | −2.0 |
| | DcD | deoxycytidine triphosphate deaminase | AAX87193.1 | −2.3 |
| | CyaA | adenylate cyclase | AAX87755.1 | −4.7 |
| | OppF | oligopeptide transport ATP-binding protein | AAX88123.1 | −1.5 |
| | TrpB | tryptophan synthase beta chain | AAX88492.1 | −1.8 |
| | HisI | histidine biosynthesis bifunctional protein HisIE | AAX87529.1 | −3.0 |
| | TrpC | tryptophan biosynthesis protein TrpCF | AAX88545.1 | −3.6 |
| | TrpD | anthranilate phosphoribosyltransferase | AAX88546.1 | −5.2 |
| | AroE | shikimate 5-dehydrogenase | AAX87686.1 | −8.3 |
| Intracellular trafficking & secretion | SecF | protein-export membrane protein SecF | AAX87299.1 | −2.0 |
| Secondary metabolite biosynthesis, transport, & catabolism | FabG | putative oxidoreductase | AAX87052.1 | −1.5 |
| Cell division & chromosome partitioning | FtsE | cell division ATP-binding protein | AAX87817.1 | −3.7 |
| General function prediction only | NTHI0052 | conserved hypothetical FtsH-interacting integral membrane protein | AAX87047.1 | 4.8 |
| | NTHI0043 | conserved hypothetical membrane protein | AAX87038.1 | 2.0 |
| | NTHI1199 | predicted ATPase | AAX88055.1 | −1.6 |
| | NTHI0779 | probable ABC transporter, ATP-binding protein | AAX87689.1 | −2.4 |
| Function unknown | NTHI0487 | conserved hypothetical transcriptional regulator with an N-terminal xre-type HTH domain | AAX87422.1 | −2.0 |
| | NTHI0319 | conserved hypothetical protein membrane protein YkgB | AAX87278.1 | −6.0 |

Results

Quantitation of NTHI NRel after Release from Biofilm Residence by Anti-rsPilA or Anti-IHF Antibodies A summary of the differences known to date between the two mechanisms of release of biofilm-resident NTHI to the NRel state used here are presented in Table 1 (Novotny, L. A., *EBioMedicine* 10, 33-44, doi: 10.1016/j.ebiom.2016.06.022 (2016); Devaraj, A., *Mol Microbiol* 96, 1119-1135, doi: 10.1111/mmi.12994 (2015); Novotny, L. A., *PLOS One* 8, e67629, doi: 10.1371/journal.pone.0067629 (2013); Goodman, S. D. et al., *Mucosal Immunol* 4, 625-637, doi:10.1038/mi.2011.27 (2011)). Briefly, anti-rsPilA which specifically targets PilA, the majority subunit of NTHI T4P induces a gradual top-down release referred to as 'dispersal' that requires active NTHI participation (e.g. expression of both T4P and autoinducer-2) (Novotny, L. A. et al.,

*Mol Microbiol* 96, 276-292, doi: 10.1111/mmi.12934 (2015)). In contrast, anti-IHF induces a rapid, species-agnostic collapse with immediate release of bacteria en masse, referred to as 'disruption' (Table 1) (Goodman, S. D. et al., *Mucosal Immunol* 4, 625-637, doi:10.1038/mi.2011.27 (2011); Brockson, M. E. et al., *Mol Microbiol* 93, 1246-1258, doi:10.1111/mmi.12735 (2014)). This latter outcome does not require bacterial function.

Applicant first quantitated the number of NTHI NRel released from established biofilms after incubation with rabbit polyclonal IgG recovered from either anti-rsPilA or anti-IHF serum. As negative controls, biofilms were incubated with polyclonal IgG recovered from either naive serum or from antiserum against the NTHI adhesin outer membrane protein P5 (OMP P5), which are unable to disperse established NTHI biofilms (Novotny, L. A. et al., *Mol Microbiol* 96, 276-292, doi: 10.1111/mmi.12934 (2015); Mokrzan, E. M., *MBio* 9, doi: 10.1128/mBio.02423-18 (2018)). Herein, biofilms were incubated for 6 hr with anti-rsPilA as maximal dispersal of NTHI occurs at this timepoint (Novotny, L. A. et al., *Mol Microbiol* 96, 276-292, doi: 10.1111/mmi.12934 (2015); Mokrzan, E. M., *MBio* 9, doi: 10.1128/mBio.02423-18 (2018)). For anti-IHF, prior work showed that maximal biofilm disruption occurred within 15 minutes of exposure (Novotny, L. A., *NPJ Vaccines* 4, 43, doi: 10.1038/s41541-019-0137-1 (2019)), therefore NRel were collected at this timepoint for enumeration.

Figure 1B:
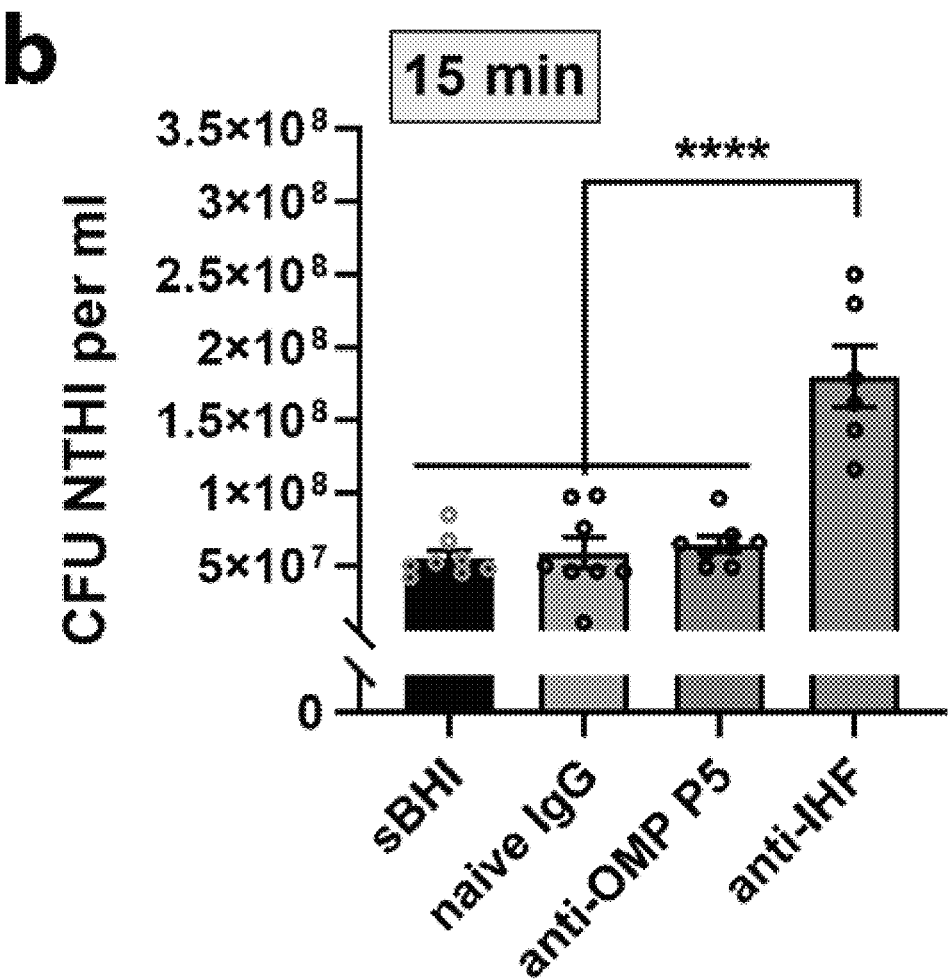

There were no difference between the number of NTHI recovered in the supernatant above biofilms when incubated with either polyclonal IgG from naive serum or polyclonal IgG from anti-OMP P5 serum compared to those incubated with sBHI (FIG. 1A). These bacteria thus represented those that were either simply planktonically growing NTHI or those that had come off the biofilm as a natural part of NTHI biofilm growth and remodeling. Conversely, incubation with anti-rsPilA induced a significant >2-fold increase in the concentration of recovered NTHI (P<0.0001). Similarly, incubation with anti-IHF resulted in a significant >3-fold increase in concentration of recovered NTHI compared to controls (P<0.0001) (FIG. 1B). These latter recovered subpopulations were considered to be either 'anti-rsPilA NRel' or 'anti-IHF NRel', respectively as they represented those NTHI released from the biofilms by the specific action of the targeted antisera (combined with any as previously characterized when recovered from the negative control samples). Thus, whereas the mechanisms for release of biofilm-resident NTHI were different, a 6 hr incubation with anti-rsPilA or a 15 min exposure to anti-IHF resulted in significant release of NTHI from established biofilms to generate two NRel subpopulations.

Proteomic Expression Profiles of Anti-rsPilA and Anti-IHF NRels were Distinct Both from their Planktonic Counterparts and Importantly, from One Another.

Figure 2A:
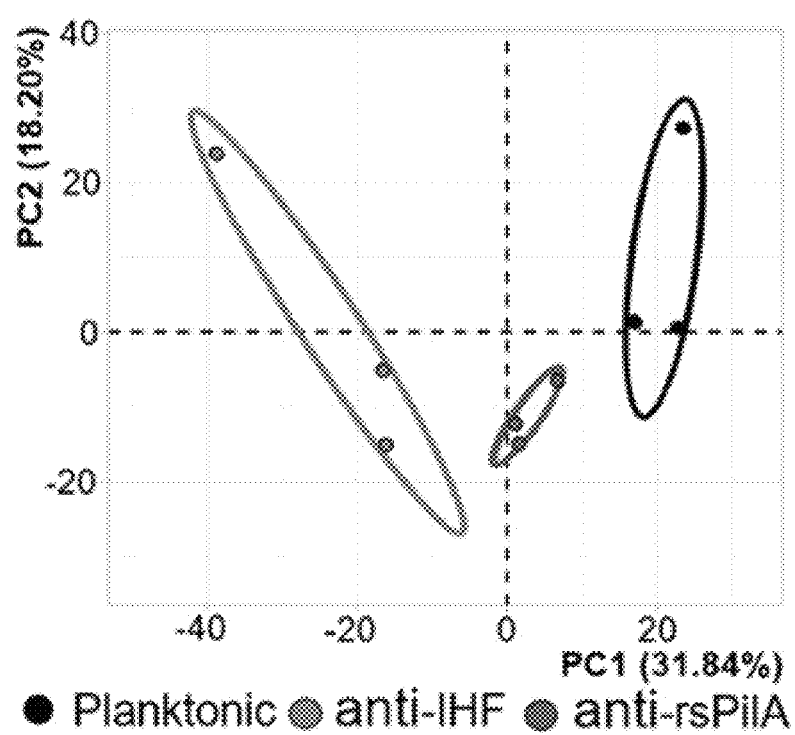
FIGS. 2A to 2D show the mechanism of release generates NRels with distinct proteomic expression profiles compared to planktonically grown NTHI and, importantly, one another.

To begin to address the question central to this work, Applicant examined the proteomic expression profiles between anti-rsPilA NRel, anti-IHF NRel, or planktonic NTHI. Mass spectrometric analysis was performed to determine the relative abundances of individual proteins expressed in each of these three subpopulations. Comparison of the proteomic expression profiles by principal component analysis (PCA) showed that NRels induced by anti-rsPilA or anti-IHF localized to discrete positions on the plot both distal from each other, as well as from planktonic NTHI (FIG. 2A). Therefore, whereas it likely could have been expected that the NTHI NRel would be different from planktonic NTHI, these two subpopulations were also very different from each other. Notably, the mechanism by which biofilm-release was induced (e.g. anti-rsPilA versus anti-IHF) resulted in two subpopulations of NTHI with distinct proteomic phenotypes, despite genetic identity.

Due to the global changes in protein expression between the anti-rsPilA or anti-IHF NRels and planktonic NTHI, Applicant next focused on identification of functional categories of proteins with differences in abundances between NRels versus planktonic NTHI. There were 63 and 103 differentially expressed proteins (DEPs) with a significant >1.5-fold increase or decrease in abundance compared to planktonic NTHI (P≤0.05) in anti-rsPilA NRels and anti-IHF NRel subpopulations, respectively, [Table 2]. Specific to anti-rsPilA NRel, annotation of DEPs by Clusters of Orthologous Groups of proteins (COG) categories revealed that the majority of DEPs were involved in energy production and conversion (19.0%) as well as amino acid transport & metabolism (17.5%) (FIG. 2B, grey bars & Table 2) (Tatusov, R. L., *Nucleic Acids Res* 28, 33-36, doi: 10.1093/nar/28.1.33 (2000); (Aziz, A. et al., *Front Microbiol* 10, 1622, doi:10.3389/fmicb.2019.01622 (2019)). Among proteins within the energy production and conversion category, enzymes involved in glycolysis, tricarboxylic acid (TCA) cycle, nitrogen metabolism, and anaerobic metabolism of glycerol were >1.5-fold decreased in abundance compared to planktonic NTHI. In contrast, proteins involved in lactate uptake and utilization were >1.5 fold increased in abundance compared to planktonic NTHI [Table 2]. Further, among anti-rsPilA NRel DEPs with >1.5-fold increase within the amino acid transport and metabolism category were tryptophan biosynthesis and cysteine metabolism enzymes. The collective differences in protein functional categories indicated that anti-rsPilA NRel were in an adaptive energy utilization and amino acid metabolic state.

Figure 2B:
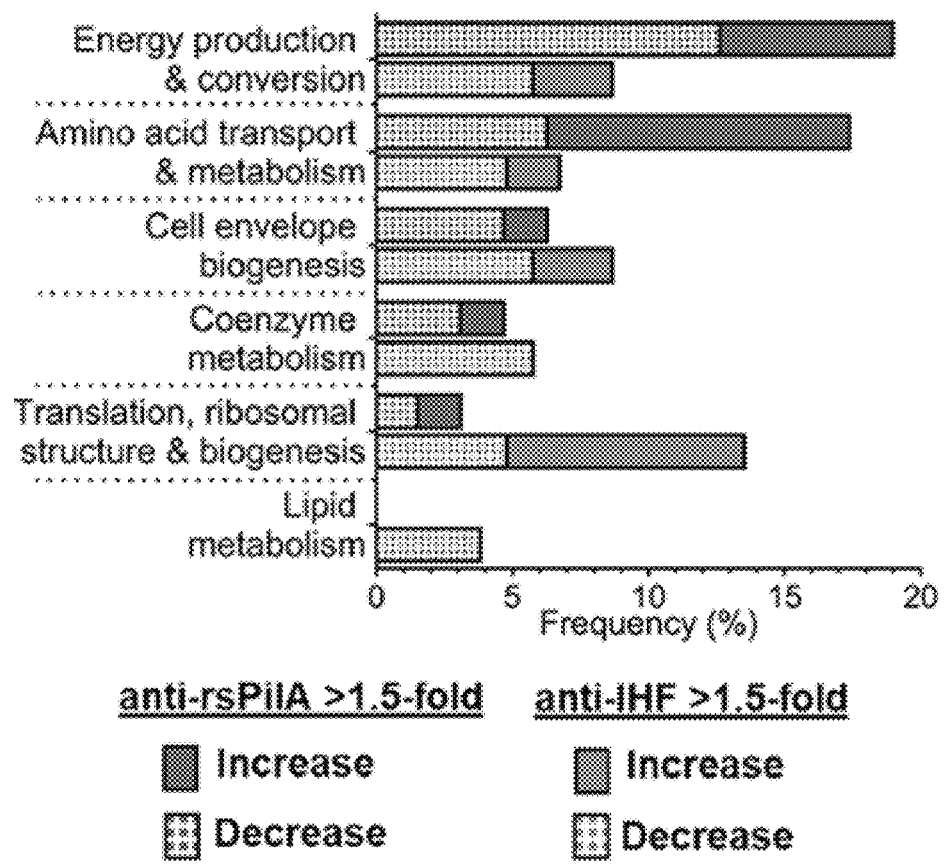

Specific to the anti-IHF NRel subpopulation, 'translation, ribosomal structure & biogenesis' was the most frequently represented (13.6%) COG category among the 103 DEPs, compared to planktonic NTHI (FIG. 2B, grey bars & Table 2). Amid these proteins, eight were 30S and 50S ribosomal proteins with >1.5-fold increase, and although ribosomal structural proteins were also increased, two translation ignition factors were decreased >1.5-fold [Table 2]. In anti-IHF NRels, expression of each of the cell envelope biogenesis, coenzyme metabolism, and lipid metabolism COG category proteins were >1.5-fold decreased compared to planktonic NTHI. For example, there was a significant decrease in Lic2A, LicC, and LicD, proteins responsible for modification of lipooligosaccharide (LOS) and decoration with a phosphorylcholine moiety (Poole, J. et al., *J Infect Dis* 208, 720-727, doi: 10.1093/infdis/jit240 (2013); Swords, W. E., *J Endotoxin Res* 9, 131-144, doi: 10.1179/096805103125001531 (2003)), and the lipoprotein carrier protein LolA, which shuttles lipoproteins from the inner membrane to the outer membrane, was also significantly decreased (Kaplan, E., *Proc Natl Acad Sci USA* 115, E7389-E7397, doi:10.1073/pnas. 1806822115 (2018)). Moreover, there were four anti-IHF NRel DEPs within the lipid metabolism category which were significantly >1.5-fold decreased in expression compared to planktonic NTHI (FIG. 2B). Additionally, coenzyme metabolism proteins required for biosynthesis of biotin, a cofactor in fatty acid biosynthesis, were also significantly >1.5-fold decreased in expression (Parsons, J. B., *Prog Lipid Res* 52, 249-276, doi: 10.1016/j.plipres.2013.02.002 (2013)). In contrast, the outer membrane lipoprotein OMP P6, involved in maintenance of outer membrane integrity and attachment to peptidoglycan, was significantly increased in expression compared to planktonic NTHI [Table 2] (Murphy, T. F., *Infect Immun* 74, 5169-5176, doi: 10.1128/IAI.00692-06 (2006)). Collectively, these data suggested that anti-IHF NRel were producing ribosomes for translation of proteins, however production of translation initiation factor proteins had yet to increase. Further anti-IHF NRels demonstrated decreased expression of LOS-modifying enzymes and lipid metabolism genes, with a concurrent increase in expression of an outer membrane integrity maintenance protein, which suggested that anti-IHF NRels had an altered membrane composition in comparison to planktonically grown NTHI.

In sum, there were distinct differences in the functional categories of DEPs between the two NRel subpopulations and planktonic NTHI. Interestingly, the DEPs were not the same for the two NRel subpopulations. These data indicated that the mechanisms of NTHI release (e.g. anti-rsPilA versus anti-IHF) generated specific protein expression signatures that were distinct for each NRel subpopulation.

Figure 2C:
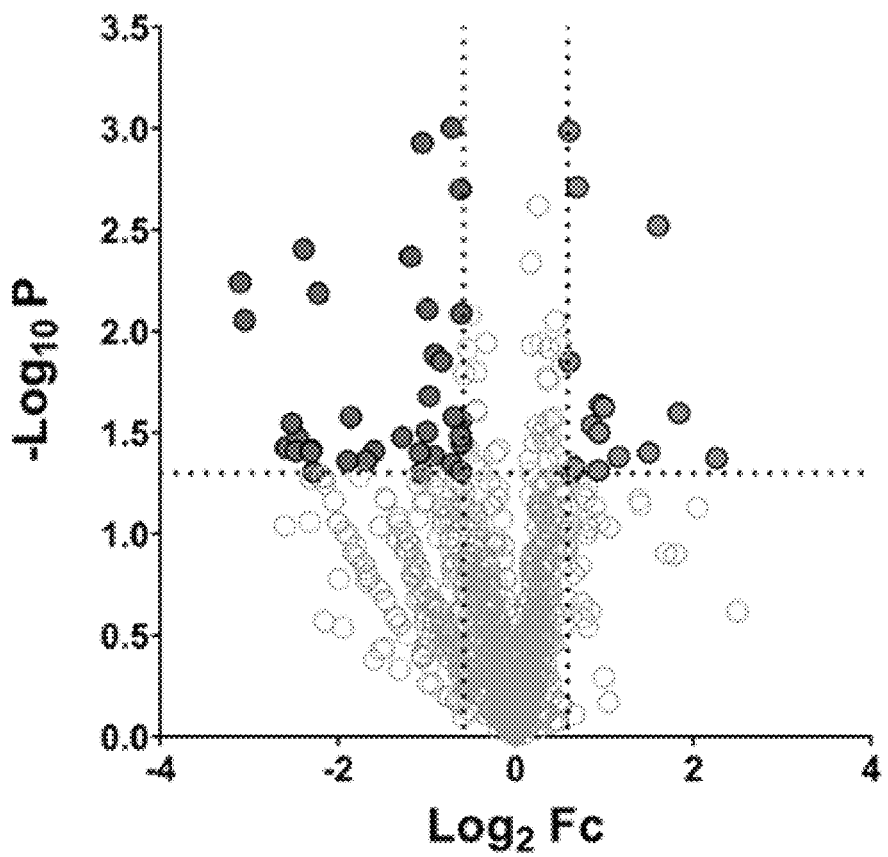

Applicant next endeavored to identify the distinct protein expression signatures between the two NRel populations. Fifty-one DEPs with >1.5-fold increase or decrease were identified amongst anti-IHF NRels versus anti-rsPilA NRels (FIG. 2C & Table 2). Of these, 15 proteins (29.4%) demonstrated a >1.5-fold increase in expression by anti-IHF NRels compared to anti-rsPilA NRels, these proteins included five of the 30S and 50S ribosomal proteins described prior. Also in greater abundance in the anti-IHF NRels compared to anti-rsPilA NRels, was OMP P6. Whereas not detected when compared to planktonic NTHI, there was a significant increase in the peptidoglycan synthesis protein, MurB, within the anti-IHF NRel DEPs compared to anti-rsPilA NRel 56. DEPs with a >1.5-fold decrease in the anti-IHF NRel compared to anti-rsPilA NRel (e.g. greater abundance in anti-rsPilA NRels) were characteristic of the abundantly expressed tryptophan biosynthesis proteins. These were in addition to lipid metabolism proteins that had already been identified as decreased in expression in the anti-IHF NRel when compared to planktonic NTHI.

Comparatively, anti-IHF NRels adopted changes in proteins involved in ribosome biogenesis and cell envelope biogenesis, whereas anti-rsPilA NRels altered expression of amino acid metabolism and energy production proteins. In total, our proteomic analyses revealed that (1) NRels were different from the planktonic NTHI and (2) each NRel subpopulation was distinct from the other. Collectively, these data indicated that the phenotype of these two NRel subpopulations was a direct consequence of the mechanism of release from biofilm residence; e.g. either active but slower, top-down dispersal due to anti-rsPilA versus rapid but passive disruption and en masse release as mediated by anti-IHF.

Figures 3A, 3B, 3C, 3D, 3E:
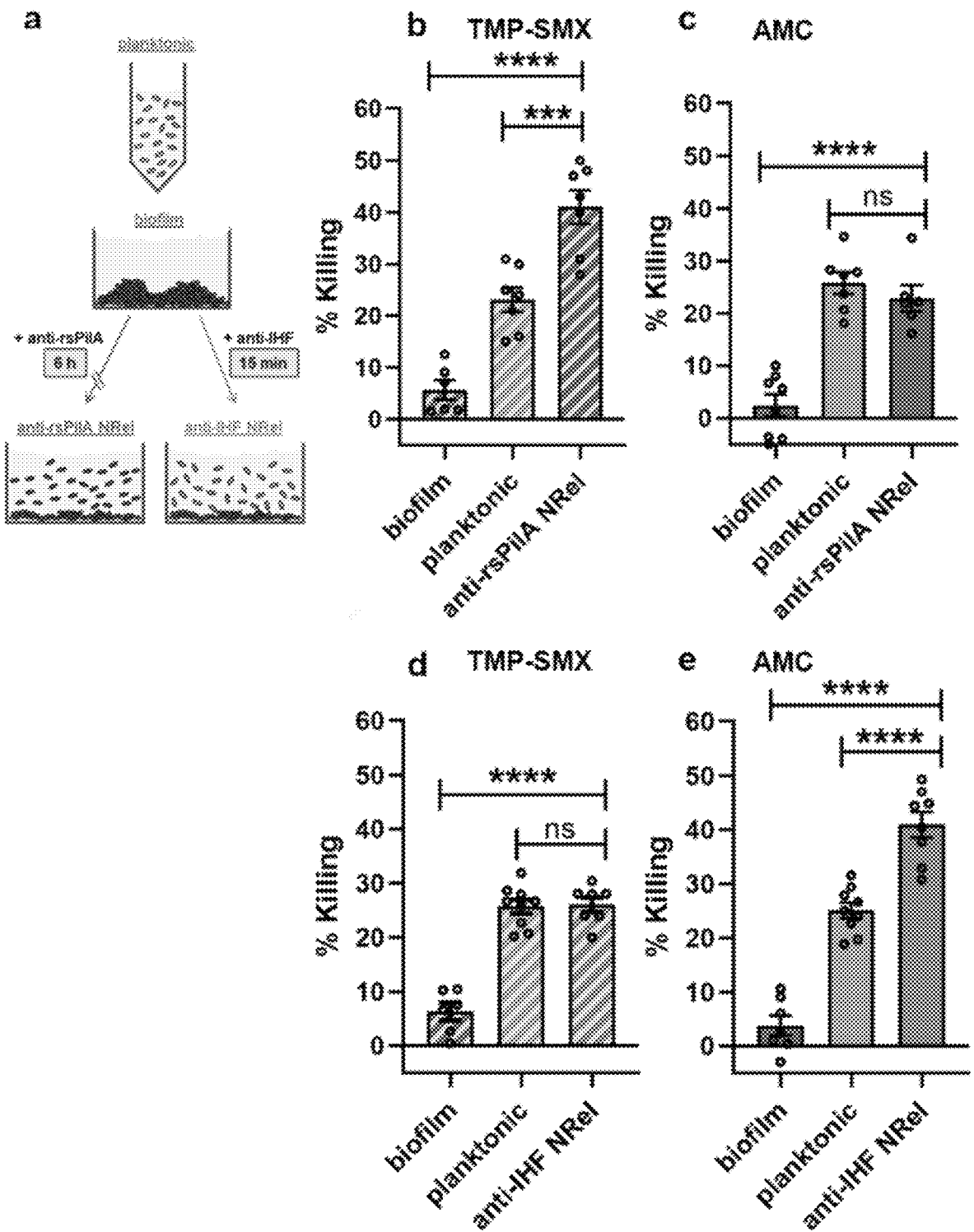
FIGS. 3A to 3E show that NRel NTHI subpopulations were more sensitive to killing than their planktonic counterparts, however this sensitivity was unique and distinct from each other.

Anti-rsPilA or Anti-IHF NRels were Significantly More Sensitive to Killing by Specific Antibiotics than Planktonic NTHI With distinct differences in relative protein expression between NRel and planktonic NTHI as well as distinct differences between the two NRel subpopulations shown, Applicant next examined whether these differences might result in additional phenotypic character, specifically antibiotic sensitivity when compared to planktonic NTHI (FIG. 3A). Given that NRel bacteria are typically more sensitive to killing by antibiotics than their planktonic counterparts (Mokrzan, E. M., MBio 9, doi: 10.1128/mBio.02423-18 (2018); Brockson, M. E. et al., Mol Microbiol 93, 1246-1258, doi: 10.1111/mmi.12735 (2014); Goodwine, J. et al., Sci Rep 9, 3763, doi: 10.1038/s41598-019-40378-z (2019); Chambers, J. R., Antimicrob Agents Chemother 61, doi: 10.1128/AAC.00846-17 (2017). Applicant assessed the sensitivity of NRels to amoxicillin and clavulanic acid ("augmentin", A/C) or trimethoprim and sulfamethoxazole (T/S), drug combinations commonly used to treat NTHI-induced respiratory tract infections (Tristram, S., Clin Microbiol Rev 20, 368-389, doi: 10.1128/CMR.00040-06 (2007); Harrison, C. J., J Antimicrob Chemother 63, 511-519, doi: 10.1093/jac/dkn538 (2009); Sethi, S., N Engl J Med 359, 2355-2365, doi: 10.1056/NEJMra0800353 (2008); K, L. C. H. et al., Infez Med 25, 27-32 (2017).) For comparison, Applicant also evaluated the relative sensitivity to these antibiotics by biofilm-resident NTHI (expected to be highly resistant) and planktonic NTHI at log phase of growth (expected to be highly sensitive) (FIG. 3A).

Anti-rsPilA NRels were significantly more sensitive than biofilm-resident NTHI to killing by either T/S or A/C ($P \leq 0.01$) (FIG. 3B & FIG. 3C). Moreover, sensitivity to T/S was significantly greater for anti-rsPilA NRels vs. mid-log phase planktonic NTHI (FIG. 3B). In contrast however, this enhanced sensitivity to killing was not observed for anti-rsPilA NRels when exposed to A/C; instead they were only as equally as sensitive as their planktonic counterparts (FIG. 3C). When Applicant evaluated anti-IHF NRels, it was found that they were also significantly more sensitive than biofilm-resident NTHI to either T/S or A/C ($P<0.05$), again as expected (FIG. 3D & FIG. 3E). Intriguingly however, and in opposition to data obtained via assessment of anti-rsPilA NRels, the anti-IHF NRel subpopulation was equally as sensitive to T/S mediated killing as their planktonic counterparts (FIG. 3D), but significantly more sensitive to A/C ($P<0.01$) (FIG. 3E). Collectively these data added yet another important distinction between these two genetically identical, yet epigenetically distinct NRel populations which supported our assertion that the exact mechanism of release from the biofilm-resident to the NRel state had a significant influence on the biological character of these newly released bacteria.

Experiment No. 2

The following examples are provided to supplement and expand on the disclosure described in Experiment No. 1.

Material and Methods

Collection and Quantitation of NRel NTHI

Nontypeable *Haemophilus influenzae* strain 86-028NP is a clinical isolate recovered from the nasopharynx of a child undergoing tympanostomy tube insertion due to chronic OM (Harrison et al., 2005; Sirakova et al., 1994) and has been maintained frozen at a low passage number. NTHI biofilms were established in brain heart infusion broth supplemented (sBHI) with 2 µg each of β-nicotinamide adenine dinucleotide (β-NAD) and heme per ml for 16 h in 8-well chambered coverglass slides as described (Jurcisek et al., 2011). After 16 h, biofilms were washed with 200 µl of equilibrated (37° C.) Dulbecco's phosphate buffered saline without calcium or magnesium (DPBS).

To collect and enumerate NRel, 16 h NTHI biofilms were gently washed, then incubated with 11 µg rabbit polyclonal IgG derived from anti-rsPilA antiserum (generated against rsPilA expressed by NTHI strain 86-028NP) (Novotny et al., 2009) for 6 h ('anti-rsPilA NRel') or 5.0 µg rabbit polyclonal IgG derived from anti-native IHF antiserum (generated against native IHF expressed by NTHI strain 86-028NP) (Novotny et al., 2019) for 15 min ('anti-IHF NRel'), antibodies were diluted in pre-warmed equilibrated (37° C., 5% $CO_2$) sBHI. These amounts of IgG match the IgG concentration present within a 1:50 dilution of each respective rabbit hyperimmune serum we used in previous studies (Brockson et al., 2014; Mokrzan et al., 2018). The incubation times used coincide with the time wherein maximal release of NTHI from biofilm residence is achieved (Mokrzan et al., 2018; Novotny et al., 2019). Rabbit polyclonal IgG derived from anti-NTHI OMP P5 or that isolated from naive rabbit serum served as negative controls and were used at equivalent concentrations to the NRel-inducing antisera (e.g. either 11 µg when compared to anti-rsPilA or 5 µg when compared to anti-IHF). Rabbit polyclonal IgG was generated by passage of whole serum or antiserum through rProtein A Protein G GraviTrap columns per manufacturer's instructions (GE Healthcare Life Sciences, Chicago, IL). After incubation for either 6 h (anti-rsPilA NRel) or 15 min (anti-IHF NRel), 190 µl of supernatant above the biofilm was gently collected from each well, sonicated for 2 min in a water bath sonicator to break up any aggregated NTHI, then serially diluted and plated on chocolate agar to quantitate CFU NTHI.

Sample Preparation for LC-MS/MS

Anti-rsPilA NRel and anti-IHF NTHI were collected as described above. Planktonic NTHI were incubated statically in sBHI until mid-log phase of growth. Samples were centrifuged for 4 min at 13,200×g, resuspended in 1 ml DPBS and centrifuged again. Pellets were flash frozen and stored at −80° C. All further processing was done by MS Bioworks, LLC (Ann Arbor, MI) as described next.

Cell pellets were suspended in buffer (2% sodium dodecyl sulfate, 150 mM NaCl, 50 mM Tris pH 8), lysed with a sonic probe (Q Sonica, Newtown, CT) and heated at 100° C. for 10 min. Protein concentration of the extract was determined by Qubit fluorometry, and 10 µg of each sample was processed by SDS-PAGE using a 10% Bis Tris NuPage mini-gel (Invitrogen) in the MES buffer system. The migration windows (1 cm gel lane) were excised and digested in-gel with trypsin using a ProGest robot (DigiLab, Hopkinton, MA) with the following protocol: 1) wash with 25 mM ammonium bicarbonate followed by acetonitrile; 2) reduce with 10 mM dithiothreitol at 60° C. followed by alkylation with 50 mM iodoacetamide at room temperature; 3) digest with trypsin (Promega, Madison, WI) at 37° C. for 4 h; 4) quench with formic acid. Supernatants were analyzed directly without further processing.

Mass Spectrometry

Half of each pooled fraction was analyzed by nano LC-MS/MS with a Waters M-Class HPLC system interfaced to a ThermoFisher Fusion Lumos mass spectrometer. Peptides were loaded on a trapping column and eluted over a 75 µm analytical column at 350 nL/min; both columns were packed with Luna C18 resin (Phenomenex, Torrance, CA). The mass spectrometer was operated in data-dependent mode, with MS and MS-MS performed in the Orbitrap at 60,000 FWHM (full width at half maximum) resolution and 15,000 FWHM resolution, respectively. The instrument was run with a 3 s cycle for MS and MS/MS. Two hours of instrument time was employed for the analysis of each sample.

Mass Spectrometry Data Processing

Data were searched using a local copy of Mascot (Matrix Science) with the following parameters: enzyme, trypsin/P; database, https://www.ncbi.nlm.nih.gov/nuccore/CP000057.2 (concatenated forward and reverse plus common contaminants); fixed modifications, carbamidomethyl (C); variable modifications: acetyl (N-term), deamidation (N,Q), oxidation (M), pyro-glu (N-term Q); mass values, monoisotopic; peptide mass tolerance, 10 ppm; fragment mass tolerance, 0.02 Da; maximum missed cleavages, 2. Mascot DAT files were parsed into Scaffold (Proteome Software) for validation, filtering and to create a non-redundant list per sample. Data were filtered using a 1% protein and peptide false discovery rate (FDR), requiring at least two unique peptides per protein. Applicant used the normalized spectral counts for downstream analysis. To evaluate the variation and reproducibility in the replicates, Applicant generated the PCA plot with 95% confidence ellipses surrounding each population (using the FactoMineR and ggplot2 packages in R), with the normalized spectral counts for each protein identified by mass spectrometry in the three samples of planktonic, anti-rsPilA NRel, and anti-IHF NRel groups (Lê et al., 2008; Wickham et al., 2016).

Differential Expression Analysis

Normalized spectral counts from three biological replicates of the three sample groups (planktonic, anti-rsPilA NRel and anti-IHF NRel), were used for pairwise comparisons to determine the differential expression of each protein using a two-tailed t-test. The P-values, Benjamini-Hochberg adjusted P-values, and fold changes are provided (Table 2). Proteins with >1.5-fold increase or decrease and with an associated P<0.05 were considered to be significantly different in expression. NTHI strain 86-028NP proteins were annotated by Clusters of Orthologous Groups of proteins (Aziz et al., 2019; Tatusov et al., 2000).

Antibiotic Sensitivity of Biofilm-Resident, Planktonic or NRel NTHI

Without being bound by theory, NRel were tested for sensitivity as compared to planktonic NTHI to certain antibiotics. The baseline for planktonic killing was set to 25% so that Applicant would be able to demonstrate a dynamic range in NRel killing by a given antibiotic. To avoid excessive manipulation or dilution of NRel NTHI, and to permit direct comparison of equal numbers of planktonic and NRel, the planktonic cell density was adjusted to the same CFU per ml as the NRel population in each experiment as follows: NTHI were incubated statically to mid log phase growth then diluted to either $3\times10^8$ CFU/ml for comparison with anti-rsPilA NRel collected at 6 h, or to $2\times10^8$ CFU/ml for comparison with anti-IHF NRel collected at 15 min (see FIG. 1). Applicant then determined the concentrations of amoxicillin (Sigma-Aldrich, St. Louis, MO) and clavulanate (U.S. Pharmacopeia, Rockville, MD), or of trimethoprim (Sigma-Aldrich) and sulfamethoxazole (Santa Cruz Biotech, Dallas, TX) that killed approximately 25% of planktonic NTHI at each density. The same antibiotic concentrations were used for the anti-IHF or anti-rsPilA NRel, the density-matched (same CFU/ml) planktonic NTHI, and the adherent biofilm for each relevant experiment. Likewise, for anti-IHF or anti-rsPilA NRel collected at 2 h, Applicant first quantitated NRel, and found ~$2.0\times10^8$ or $4.0\times10^8$ CFU/ml released by exposure of biofilms to anti-rsPilA or anti-IHF IgG, respectively. Applicant then assessed killing of anti-IHF or anti-rsPilA NRel by concentrations of amoxicillin plus clavulanic acid ("augmentin", AMC) or trimethoprim plus sulfamethoxazole (TMP-SMX) that killed 25% of the planktonic NTHI at the same density.

Anti-rsPilA or anti-IHF NRel were collected and sonicated as described above. After sonication for 2 min in a water bath sonicator to break up any NTHI aggregates, NRel or planktonic NTHI were incubated with the indicated antibiotics at 37° C. for 2 h, then serially diluted and plated on chocolate agar to quantify viable NTHI. To assay biofilm-resident NTHI, biofilms were established for 16 h at 37° C. as described above, washed twice with DPBS and incubated in sBHI supplemented with the indicated antibiotics at 37° C. After 2 h, biofilm-resident NTHI were collected by forceful pipetting, sonicated for 2 min and enumerated as described above. All experiments were performed at least three times on separate days with two or three technical replicates for each treatment and control group.

Flow Cytometry

As described above, NTHI biofilms were established in 8-well chambered coverglass slides. After 16 h, medium was aspirated from each well and biofilms incubated with 5 µg IgG from rabbit polyclonal IHF for 15 min or 11 µg IgG from polyclonal rabbit anti-rsPilA for 6 h at 37° C., 5% $CO_2$. At each respective timepoint, 190 µl of supernatant above each biofilm was collected, transferred into 1 µM FM1-43FX (Invitrogen, Carlsbad, CA) in Hank's Balanced Salt Solution and incubated static for 15 min at room temperature. NTHI scraped from a chocolate agar plate into buffer served as a 'clumped' bacterial control. NTHI suspended in buffer by gentle pipetting followed by sonication for 5 min served as a 'non-clumped' bacterial control. Forward scatter and side scatter profiles of fluorescently stained NTHI were examined with a BD LSR II flow cytometer and FloJo software. 10,000 events were collected for each sample.

RNA Isolation and qRT-PCR Assay

For RNA isolation, Applicant seeded 6 ml of NTHI at $2 \times 10^5$ CFU/ml into a T-25 tissue culture flask. After 16 h incubation at 37° C., 5% $CO_2$, the flask was gently inverted, and the medium poured off. With the flask upside down, 6 ml prewarmed DPBS was added then the flask was slowly inverted to gently wash the biofilm. To remove the DPBS wash, the flask was inverted again and DPBS poured off. Antibody diluted in sBHI was added with the flask still upside down, to deliver the same concentration of antibody/$cm^2$ as used in chamberslide assays [this translated to ~52 µg anti-IHF IgG per ml or ~113 µg anti-rsPilA IgG per ml]. The flask was returned to the incubator, inverted gently so that the medium again covered the biofilm. After 3 min for anti-IHF, or 3 h for anti-rsPilA, the flask was inverted and the NRel NTHI collected by pouring into a 15 ml conical tube. NRel were centrifuged for 1 min at 16,000×g, the supernatant aspirated, and 1 ml TRIzol™ Reagent (ThermoFisher, Waltham, MA) was immediately added to the bacterial pellet. Samples were stored at −80° C.

RNA was purified with a Qiagen RNeasy kit (Qiagen, Germantown, MD). Residual DNA was removed by treatment with DNase I (NEB, Ipswich, MA), per manufacturer's instructions for 45 min at 37° C. in the presence of 20 U SUPERase In RNase inhibitor (Ambion, Austin, TX). Relative gene expression was assessed by quantitative reverse transcription-PCR (qRT-PCR) with a Superscript III Platinum SYBR Green One-Step qRT-PCR kit (ThermoFisher) per manufacturer. Gene expression was normalized to 16S, and relative expression was calculated by the comparative ($\Delta\Delta C_T$) method, with fold change in gene expression expressed as $2^{(-\Delta\Delta C_T)}$. Results represent the mean of 3 biological samples, each assayed in triplicate. A 2-fold change in gene expression was considered biologically significant. Primers used are listed in Table 3.

TABLE 3

Primers used in this study

| Primer | Sequence |
|---|---|
| acrR-forward | CGGCGATAAATTTAGCCTCTGA |
| acrR-reverse | TGAATCGCACGCCAAGAG |
| artM-forward | GTCTTATCCAATGCGTGGTTCT |
| artM-reverse | GGATGCTAATGCCGTTCCTTTA |
| deaD-forward | TGTGGTGAACTACGACATTCC |
| deaD-reverse | GATCCTGATCGGCTGTGAATAA |
| emrA-forward | CCGCAAATACAGAATGCGATAAA |
| emrA-reverse | ATTACGACGCGCCACATAG |
| emrB-forward | CGGTAACTTTCGAGCCATCA |
| emrB-reverse | GCCAGACAGCGTTATTGTAGTA |
| fis-forward | TAATCCTGCCGATGCCTTAAC |
| fis-reverse | CGGGTTTGATTACCACGAGTAT |
| folA-forward | TTGGTCGTCCACTACCTAAAC |
| folA-reverse | GACCGCACTTTCAAAGCTATC |
| folP-forward | TGCTGGATTTCTGTCGATTCTT |
| folP-reverse | GCTCTTGCAAAGCACGAATATC |
| 16S-forward | AAAGGAGACTGCCAGTGATAAA |
| 16S-reverse | CCCTCTGTATACGCCATTGTAG |

(SEQ ID NO: 40-(SEQ ID NO: 57)

Statistical Analyses

Data are expressed as mean±SEM of at least three biological replicates performed on separate days with two or three technical replicates per sample. Statistical analyses were performed with GraphPad (Prism) software version 8.2. Multiple comparisons were made by one-way analysis of variance with the Holm-Sidak correction. All other comparisons were made with student's t-test. Comparisons of fold changes in normalized spectral counts of proteins identified by mass spectrometry and generation principal component analysis were performed in R (Bioconductor). Flow cytometry data were analyzed by the Kolmogorov-Smirnov test to compare the cumulative distribution of anti-rsPilA NRel versus anti-IHF NRel for forward scatter and side scatter profiles.

Data Availability

Results

Incubation of NTHI Biofilms with Anti-rsPilA or Anti-IHF Antibodies Released NTHI from Biofilm Residence Anti-rsPilA antibodies specifically target PilA, the majority subunit of NTHI T4P (Novotny et al., 2015), to induce a more gradual, top-down release of NTHI from the biofilm which we refer to as 'dispersal' as this is a programmed process that requires active NTHI participation by expression of both T4P and AI-2-dependent signaling (Novotny et al., 2015). In contrast, anti-IHF antibodies induce a rapid, non-programmed, species-independent, biofilm matrix collapse with immediate release of bacteria en masse, we refer to as 'disruption' (Brockson et al., 2014; Goodman et al., 2011). This latter outcome does not require bacterial action Table 2 (Devaraj et al., 2015; Goodman et al., 2011; Novotny et al., 2013a; Novotny et al., 2016). (Devaraj et al., 2015; Goodman et al., 2011; Novotny et al., 2013a; Novotny et al., 2016). Applicant quantified herein the number of NTHI released from biofilm residence after incubation with rabbit polyclonal IgG isolated from either anti-rsPilA or anti-IHF serum. Sterile culture medium or an equivalent concentration of polyclonal IgG recovered from either naive serum or from antiserum against the NTHI adhesin outer membrane protein P5 (OMP P5), none of which disperse established NTHI biofilms (Mokrzan et al., 2018; Novotny et al., 2015), served as negative controls. It was previously shown that NTHI biofilms established for 16 h and incubated with anti-rsPilA are maximally dispersed after 6 h (Mokrzan et al., 2018; Novotny et al., 2015), whereas complete collapse of a similarly aged biofilm is achieved after 15 min with anti-IHF (Novotny et al., 2019). Thus, for this assay, NRel induced by anti-rsPilA or anti-IHF were collected for enumeration at either 6 h or 15 min, respectively (Mokrzan et al., 2018; Novotny et al., 2019; Novotny et al., 2015).

The concentration of NTHI recovered from supernatants above biofilms that had been incubated with polyclonal IgG from either naive or anti-OMP P5 serum was similar to that when incubated with sterile sBHI (FIG. 1A and FIG. 1B). This was anticipated as none of these three treatments were expected to significantly alter the normal equilibrium wherein bacteria go on/come off a biofilm as a natural part of biofilm growth and remodeling within the 6 h or 15 min incubation periods. Conversely, incubation with anti-rsPilA IgG for 6 h induced a significant >2-fold increase in the concentration of released NTHI (FIG. 1A, P<0.0001). Similarly, incubation with anti-IHF IgG for 15 min resulted in a significant >3-fold increase in concentration of released NTHI (P<0.0001) (FIG. 1B). The lower concentration of the 3 control populations, compared to those similarly depicted in FIG. 1A, reflects the shorter 15 min incubation period. Applicant referred to these populations of NTHI newly released from biofilm-residence as 'anti-rsPilA NRel' or 'anti-IHF NRel' to reflect their generation due to the action of two unique and specifically-targeted antibodies wherein the mechanisms and kinetics of release of biofilm resident NTHI are different (Table 2).

FACS Analysis of Anti-rsPilA and Anti-IHF NRel Populations

Figure 5A:
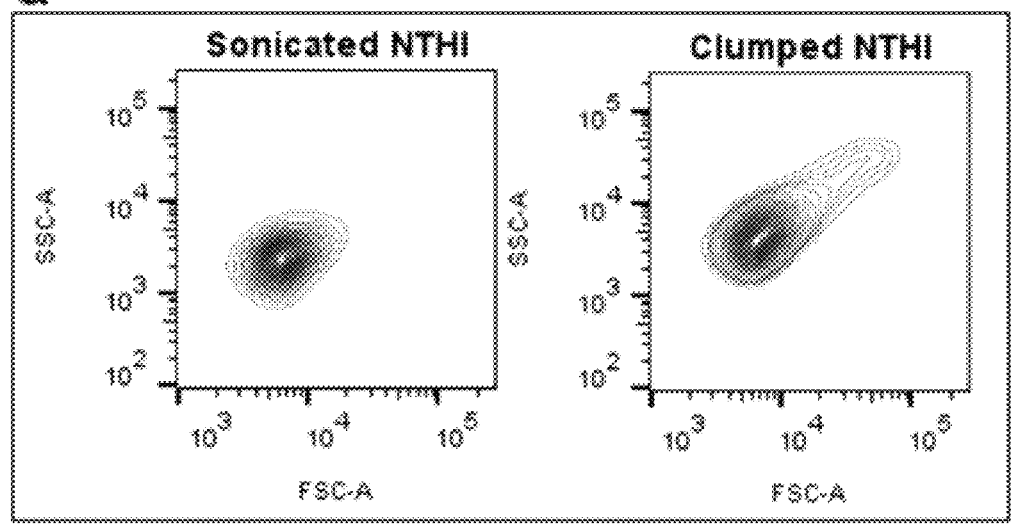
FIGS. 5A to 5E show anti-rsPilA NRel were released from a biofilm as individual cells whereas anti-IHF NRel were aggregated.
Figure 5B:
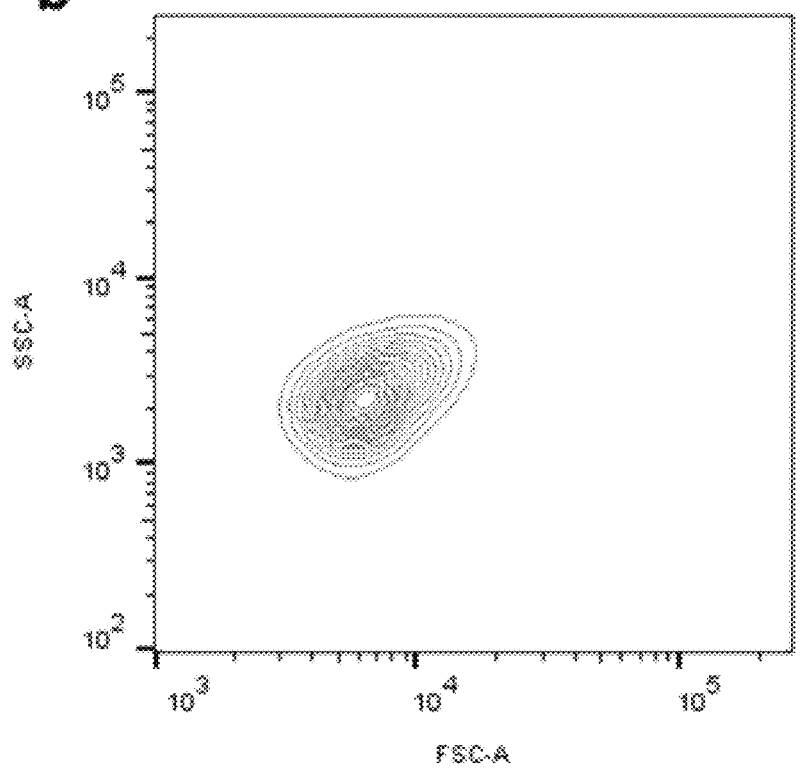
Figure 5C:
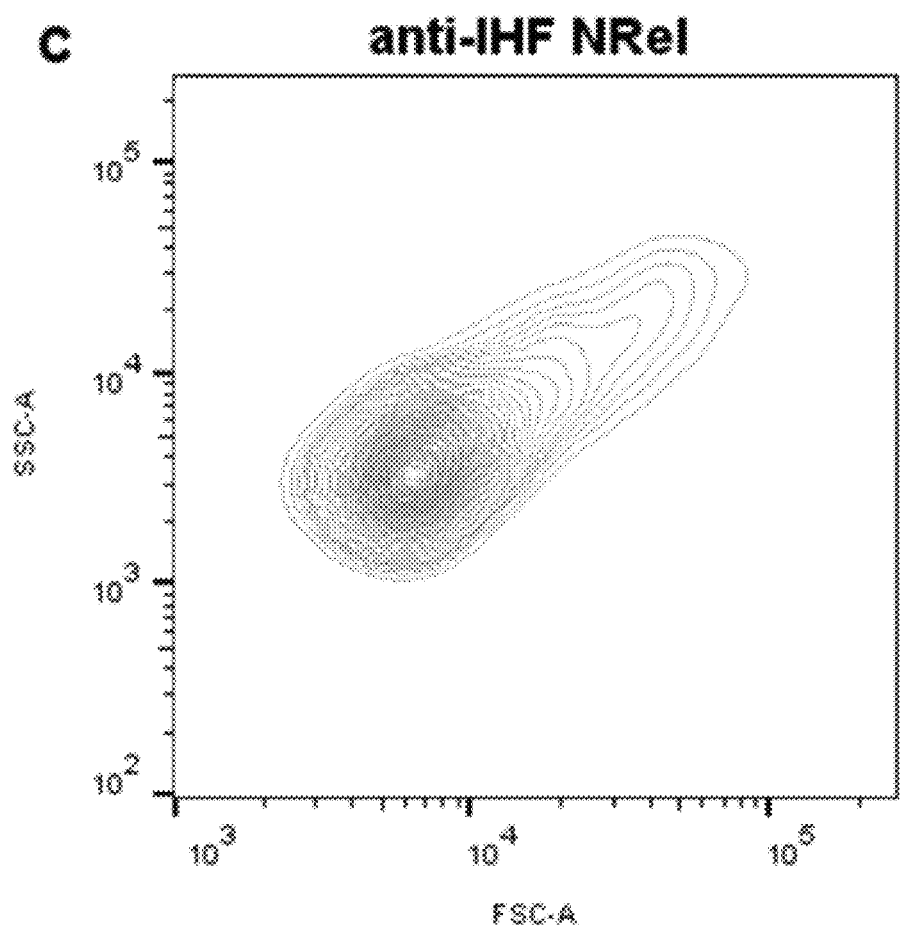
Figures 5D, 5E:
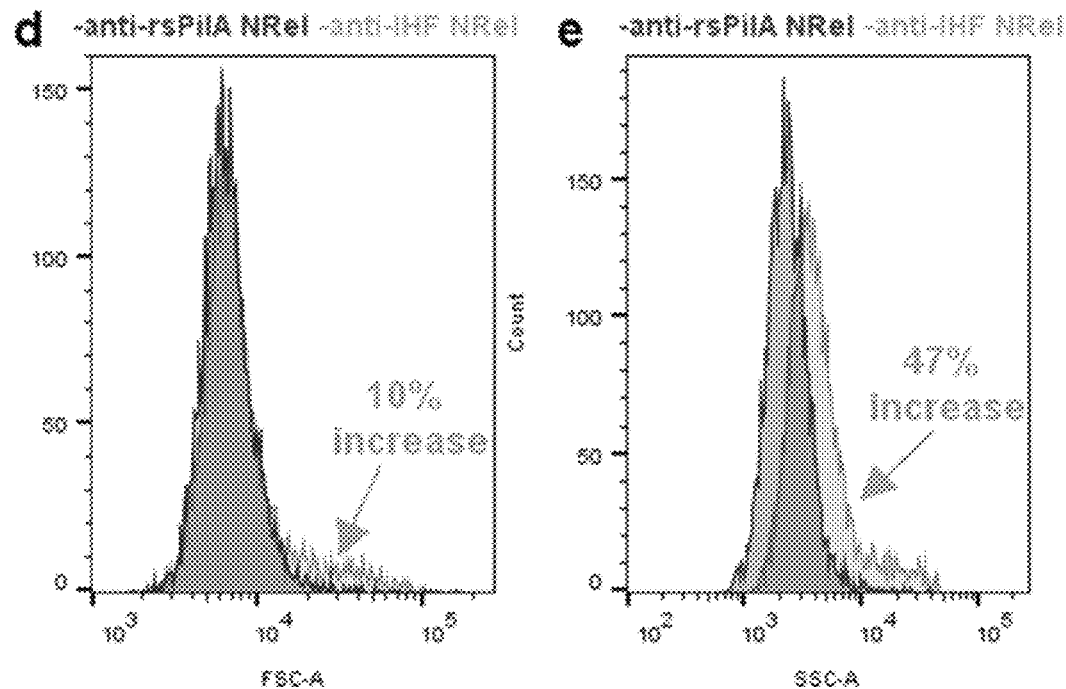

As hypothesized and based on gross observations of the NRel populations as they were recovered, the scatter profiles for anti-rsPilA NRel and anti-IHF NRel are also distinct. Applicant performed flow cytometry and examined the forward scatter and side scatter profiles for each NRel population to reveal potential differences in size and complexity. The scatter profile for a suspension of NTHI that was briefly sonicated prior to assessment revealed a population of cells of similar size (i.e. single cells), whereas a larger and more complex population (i.e. aggregates) was additionally observed in the sample with bacterial aggregates, indicated by greater side scatter and forward scatter (FIG. 5A). Anti-rsPilA NRel appear to be released as individual cells (FIG. 5B), as a single, uniform population was revealed. Conversely, the scatter profile for anti-IHF NRel included a larger population, indicative of bacterial aggregates and/or biofilm remnants (FIG. 5C). Moreover, the anti-IHF NRel population was 10% larger in size (FIG. 5D) and 47% more complex (FIG. 5E) compared to the anti-rsPilA NRel, further evidence of distinct character of each population. Moreover, these data fit well with the described differences for how each antiserum mediates release of NTHI from biofilm residence (Table 2) as the programmed release mediated via dispersal would indeed favor release as individual cells, whereas the rapid physical collapse of the biofilm to release NTHI via disruption would favor release as aggregates.

Proteomic Expression Profiles of Anti-rsPilA and Anti-IHF NRel were Distinct from Both their Planktonically Grown Counterparts and Importantly, from Each Other Given our ultimate interest in the relative sensitivity of NRel NTHI to killing by antibiotics, Applicant next questioned how the anti-rsPilA and anti-IHF NRel populations compared phenotypically to not only planktonically grown NTHI (the population used clinically to determine antibiotic sensitivities, or MIC values), but also to each other. To begin to address this central question, Applicant examined the proteomic expression profiles of anti-rsPilA NRel, anti-IHF NRel and planktonic NTHI (grown statically in broth to mid-log phase) by mass spectrometric analysis. The total proteomic expression profiles for anti-rsPilA and anti-IHF NRel were different from planktonic NTHI, as shown by the discrete locations of each population on the principal component analysis (PCA) plot (FIG. 2A). Moreover, although it had been shown that NRel population proteomic profiles would be different from planktonic cells (Brockson et al., 2014; Mokrzan et al., 2018), the two NRel populations were also very different from each other, as highlighted by the 95% confidence ellipses, despite genetic identity.

Figure 2D:
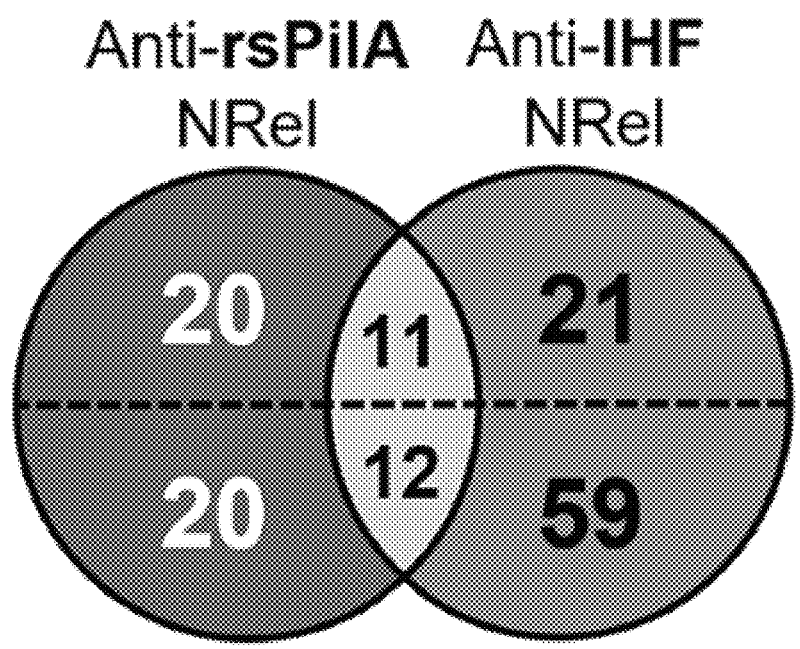

Due to the overall global changes in protein expression between the anti-rsPilA or anti-IHF NRel and planktonically grown NTHI, Applicant next examined proteins with differences in abundance between the two NRel populations, after each was first compared to planktonic NTHI. There was a total of 63 and 103 differentially expressed proteins (DEPs) with a significant >1.5-fold increase or decrease in abundance compared to planktonic NTHI (P<0.05) in anti-rsPilA NRel and anti-IHF NRel populations, respectively (FIG. 2D & Table 2). Moreover, anti-rsPilA NRel expressed 40 proteins and anti-IHF NRel expressed 80 proteins with uniquely significant differences in abundance compared to planktonic NTHI, which provided further evidence of the difference between the two NRel populations (FIG. 2D, dark versus lighter grey sections).

Applicant next annotated the DEPs by Clusters of Orthologous Groups of proteins (COG) (Aziz et al., 2019; Tatusov et al., 2000) to assess the relative functions of the two NRel DEPs as a result of release from biofilm residence via distinct antibody-mediated dispersal versus disruption. For the anti-rsPilA NRels, annotation of the 63 DEPs revealed that the most frequently represented COG categories (36.5%) were involved in either energy production & conversion (19.0%) or amino acid transport & metabolism (17.5%) (FIG. 2C, purple bars & Table 2). Specific to energy production & conversion category, enzymes involved in glycolysis, tricarboxylic acid cycle, nitrogen metabolism, and anaerobic metabolism of glycerol were >1.5-fold decreased in abundance compared to planktonic NTHI. Whereas proteins involved in lactate uptake and utilization were >1.5 fold increased in abundance compared to planktonic NTHI (Table 2). In the same category, DEPs specific to anti-rsPilA NRel with >1.5-fold increase included tryptophan biosynthesis and cysteine metabolism enzymes. The collective differences in protein functional categories indicated that anti-rsPilA NRel were primarily in an active-adaptive energy utilization and amino acid metabolic state.

In contrast, within the anti-IHF NRel population, 'translation, ribosomal structure & biogenesis' was the most frequently represented COG category (13.6%) among the 103 DEPs, compared to planktonic NTHI (FIG. 2B, orange bars & Table 2). Specific to anti-IHF NRel DEPs, eight were 30S and 50S ribosomal proteins with >1.5-fold increase, and although ribosomal structural proteins were also increased, two translation initiation factors were decreased >1.5-fold (Table 2). Further, expression of each of the cell envelope biogenesis, coenzyme metabolism, and lipid metabolism COG category proteins were >1.5-fold decreased compared to planktonic NTHI, for example, Lic2A, LicC, and LicD, proteins responsible for modification of lipooligosaccharide (LOS) and decoration with a phosphorylcholine moiety (Poole et al., 2013; Swords et al., 2003), and the lipoprotein carrier protein LolA, which shuttles lipoproteins from the inner membrane to the outer membrane (Kaplan et al., 2018). Moreover, there were four anti-IHF NRel DEPs within the lipid metabolism category which were significantly >1.5-fold decreased in expression compared to planktonic NTHI (FIG. 2B). Additionally, coenzyme metabolism proteins required for biosynthesis of biotin, a cofactor in fatty acid biosynthesis, were also significantly >1.5-fold decreased in expression (Parsons and Rock, 2013). In contrast, the outer membrane lipoprotein OMP P6, involved in maintenance of outer membrane integrity and attachment to peptidoglycan, and the major outer membrane protein OMP P2 were significantly increased in expression compared to planktonic NTHI (Table 2) (Murphy et al., 2006; Sikkema and Murphy, 1992). Collectively, these data suggested that anti-IHF NRel contained abundant ribosomes for translation of proteins, however translation was limited due to the reduced translation initiation factor proteins. Further, anti-IHF NRel demonstrated decreased expression of LOS-modifying enzymes and lipid metabolism genes, with a concurrent increase in expression of outer membrane integrity maintenance proteins, which suggested differences in membrane composition of anti-IHF NRel compared to planktonically grown NTHI.

Figures 6A, 6B, 6C:
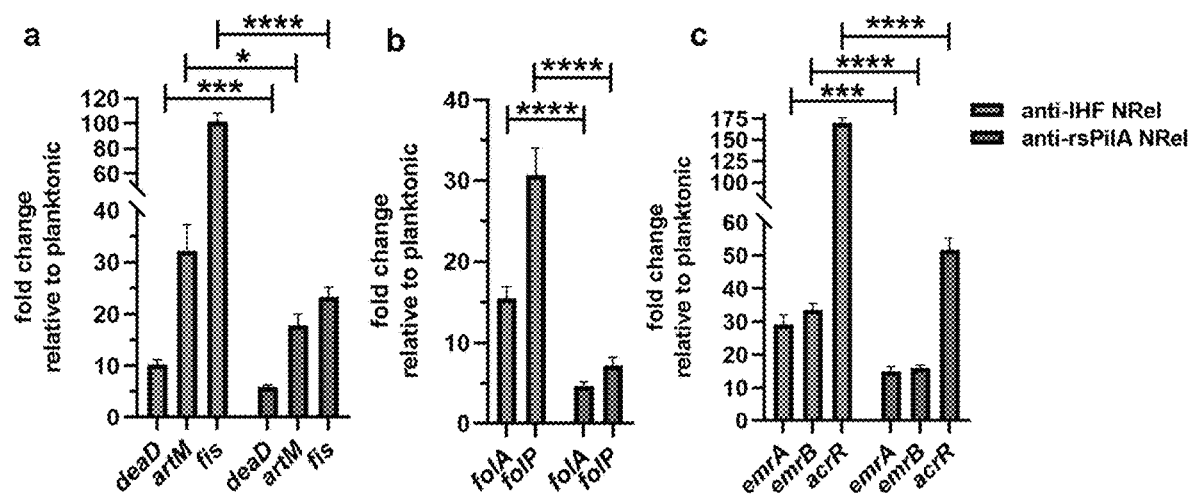
FIGS. 6A to 6C show the differences in relative gene expression support the observed distinct anti-IHF and anti-rsPilA NRel phenotypes, including antibiotic sensitivities. Results of qRT-PCR assay to examine the expression of genes by NRel relative to planktonic NTHI.
Figure 7:
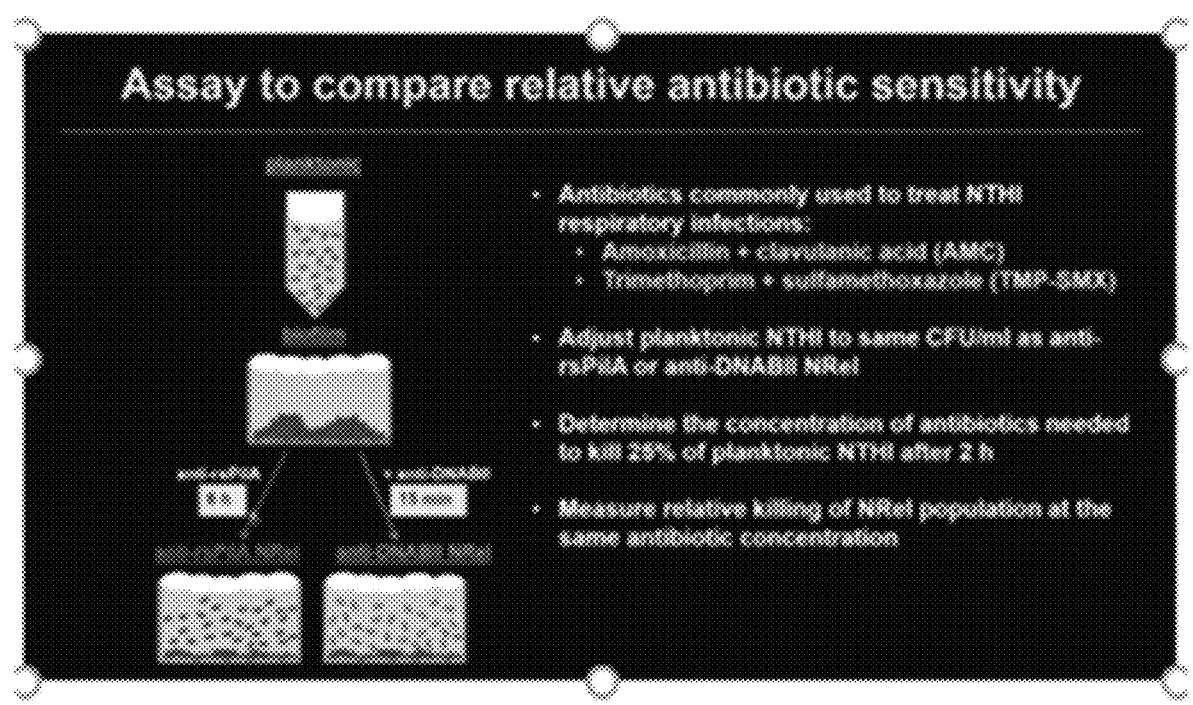
FIG. 7 is a schematic showing the different lifestyles of bacteria wherein when grown planktonically (a very artificial environment that does not represent growth in chronic/recurrent human disease, but rather the way bacteria are grown in clinical microbiology labs to determine which antibiotic to use for the patient and at what dose). Planktonic bacteria are canonically considered to be the most sensitive to being killed by antibiotics whereas those resident within a biofilm (as they exist during disease) are extremely resistant to being killed by antibiotics. As disclosed herein is Applicant's discovery that bacteria newly released (NRel) from biofilm residence are often now either as sensitive to being killed by antibiotics as their planktonic counterparts, or often significantly more sensitive to being killed than their planktonic counterparts.
Figure 8A:
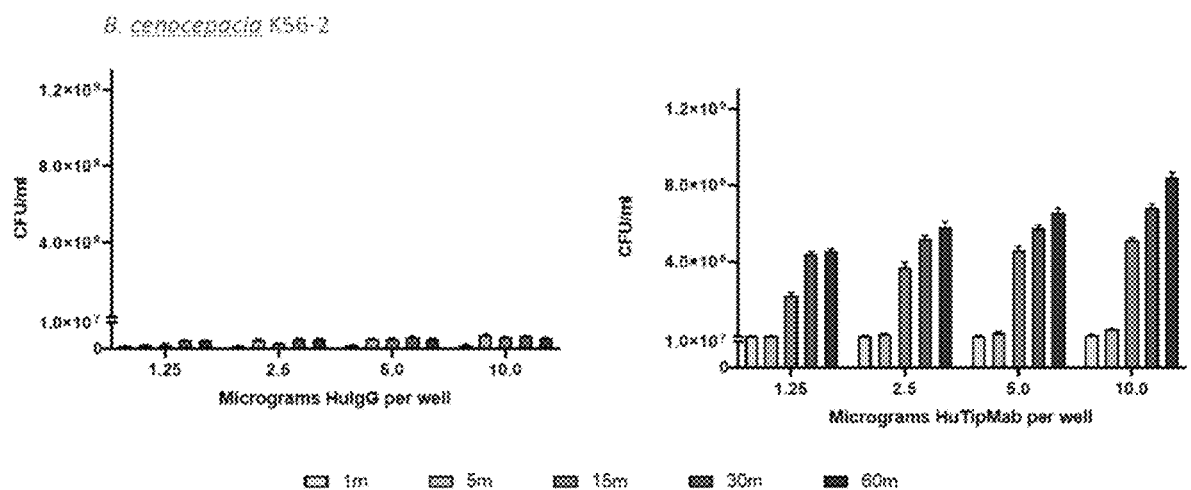
FIGS. 8A to 8F show the time and dose-dependence of release of six diverse species of human pathogens into the NRel state by anti-DNABII which occurs when established biofilms are incubated with a humanized monoclonal antibody raised against a chimeric peptide identified as IhfA5-mIhfB4 tip chimer (The humanized antibody utilized in this example (identified in the Figure and herein as "HuTip-Mab") comprises heavy chain 1 (HCl) and light chain 2 (LC2) as disclosed herein) but not when similarly incubated with the negative control ("HulgG" a commercially available naïve human serum of the isotype IgG). (Note that some examples are plotted in light grey and others in dark grey.) This is due to the fact that while all are released to the NRel state rapidly by this antibody, in this particular assay some species, also demonstrate a jump in the number of NRel at 30 mins regardless of dose e.g. B. cenocepacia, A. baumanii, S. aureus and nontypeable H. influenzae (NTHI)]. Other species (e.g. S. pneumoniae and P. aeruginosa) are also released rapidly, however we observed a gradual, more linear increase over time.
Figure 8B:
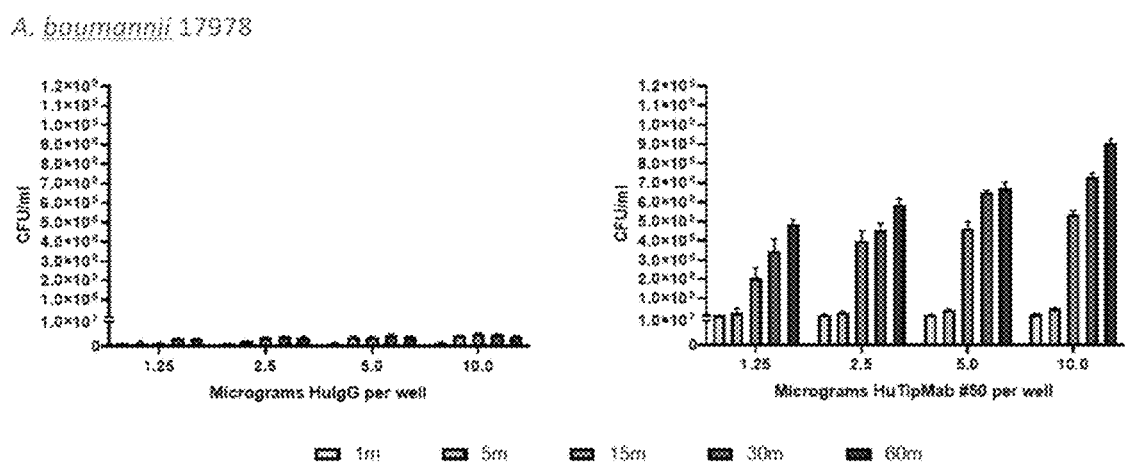
Figure 8C:
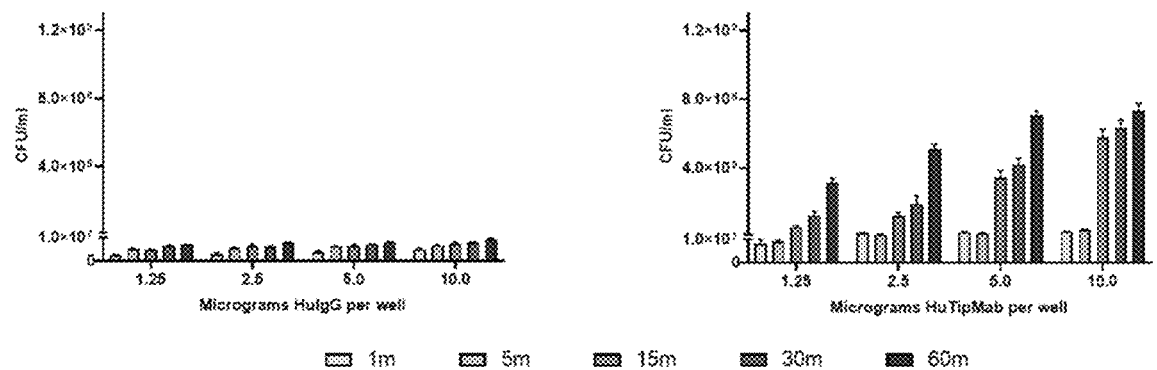
Figure 8D:
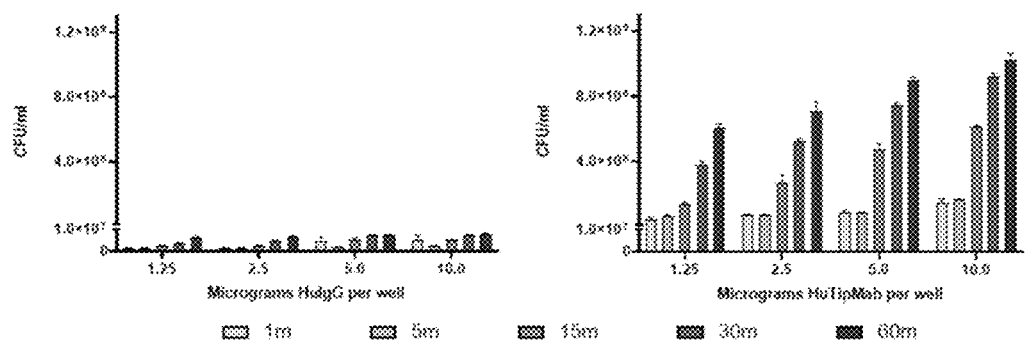
Figure 8E:
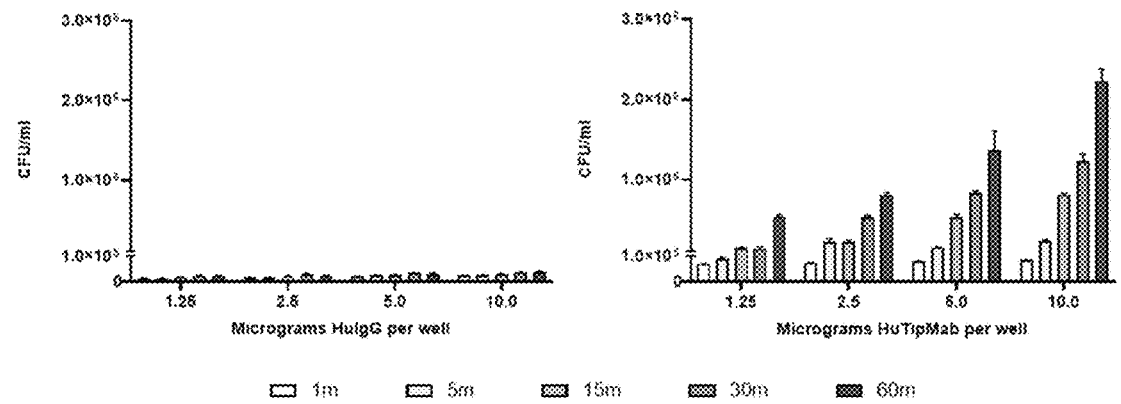
Figure 8F:
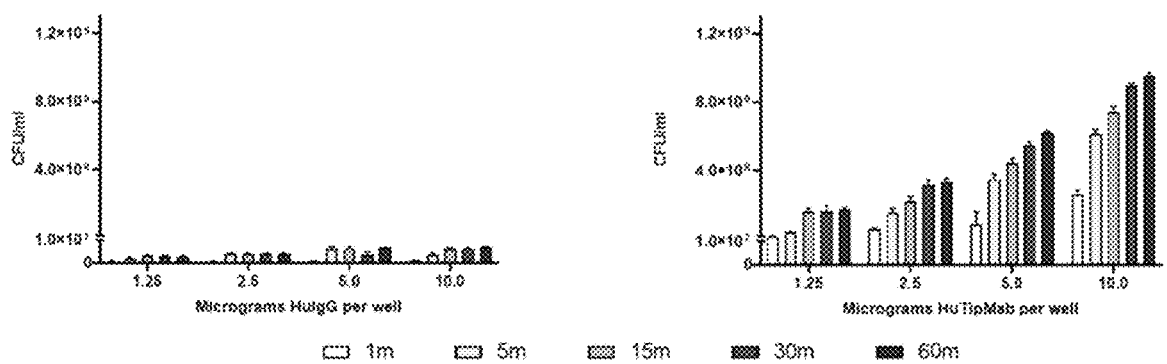
Figure 9:
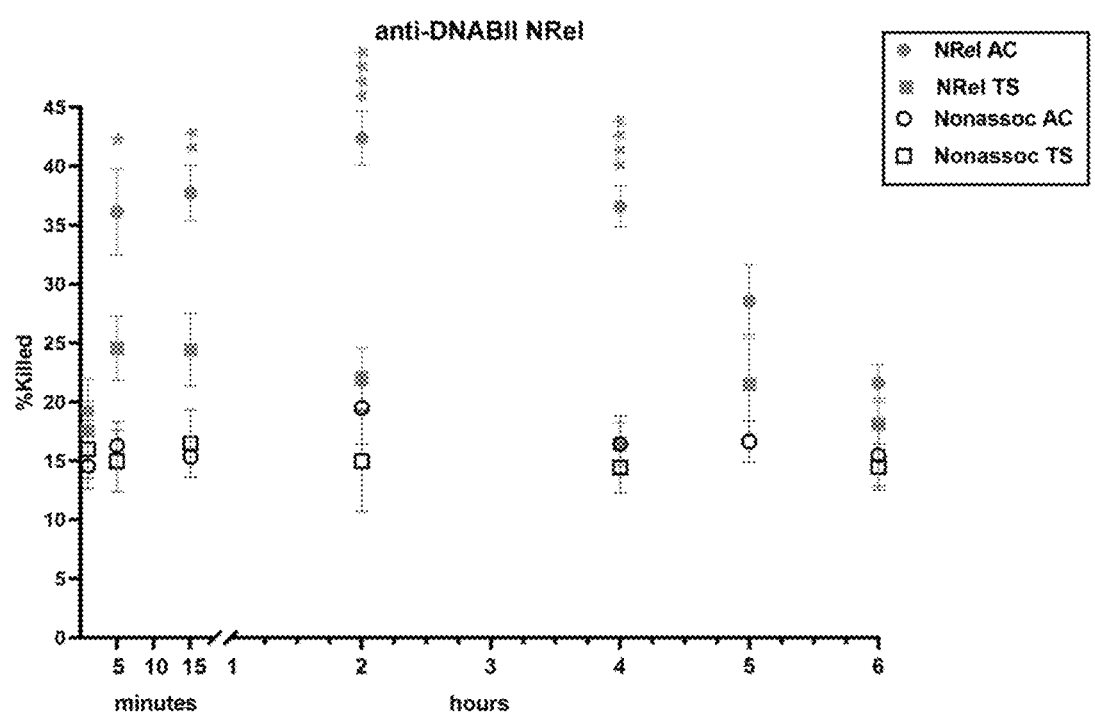
FIG. 9 show the kinetics of the development of the significant but distinct sensitivity to antibiotic-mediated killing of the NRel population induced by incubation with antibody directed against a DNABII target. Applicant tested for this phenotype for either Amox/Clav or Trimethoprim/Sulfamethoxazole to determine when this sensitivity first appears and how long this NRel phenotype lasts (i.e. what is the window of opportunity in which to treat a patient with a biofilm disease?). Here, NRel are compared not to planktonic bacteria (due to their artificiality) but rather to "Non-Associated" bacteria which are those found in the supernatant above the biofilm but not associated with biofilm residence as this population represents those bacteria that naturally come off the biofilm or were never a part of the biofilm which is a normal aspect of the preferred bacterial lifestyle in nature. For anti-DNABII NRel, this significantly greater sensitivity to Amox/Clav occurs within the first 5 minutes, reaches a maximum by 2 hrs after exposure and which lasts until ~3 hrs, then wanes by 6 hours post exposure. Note that the same hypersensitive phenotype is not shown for the antibiotic Trimethoprim/Sulfamethoxazole as anti-DNABII NRel are as but not more sensitive that their Non-Associated counterparts. Box Legend: NRelAC—relative killing by Amox/Clav; NRel TS—relative killing by Trimethoprim/Sulfamethoxazole; open symbols are the same but for the non-associated populations of bacteria as now described in this legend. Data was generated with a murine anti-tip chimer antibody.
Figure 10:
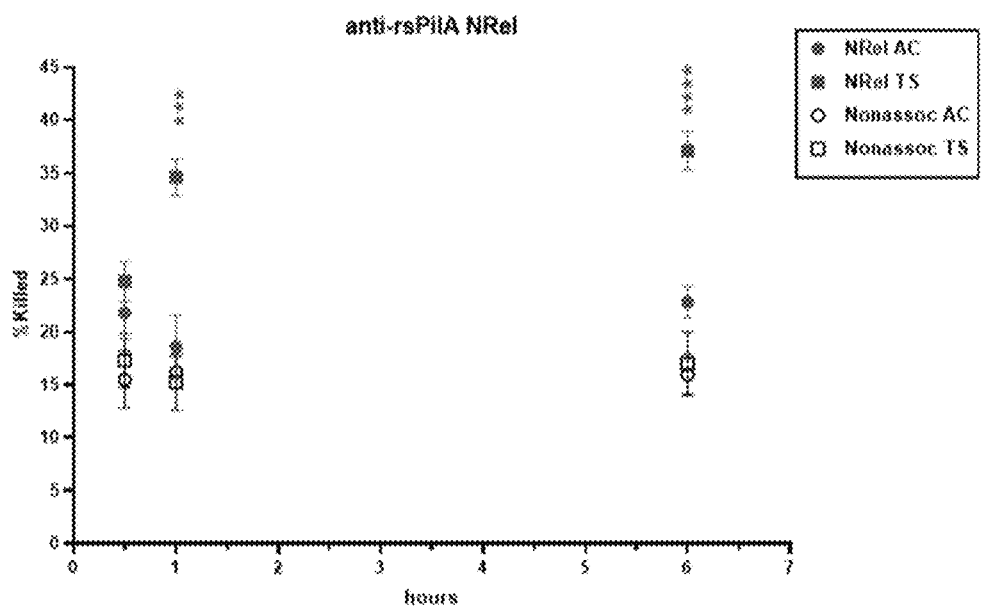
FIG. 10 describes the NRel phenotype for the population of NTHI that were released from biofilm residence by antibody directed against the majority subunit of the type IV twitching pilus (recombinant soluble PilA or rsPilA). Here, this anti-rsPilA NRel phenotype is now showing significantly greater sensitivity to being killed by Trimethoprim/Sulfamethoxazole and this does not appear until approximately one hour after exposure to antibodies against rsPilA. To date, this highly significant phenotype remains at 6 hrs, however these studies continue for later timepoints as well as to fill in those between 1 and 6 hours. Box Legend: NRelAC—relative killing by Amox/Clav; NRel TS—relative killing by Trimethoprim/Sulfamethoxazole; open symbols are the same but for the non-associated populations of bacteria as now described in this legend. Data was generated with a murine anti-tip chimer antibody.
Figure 11A:
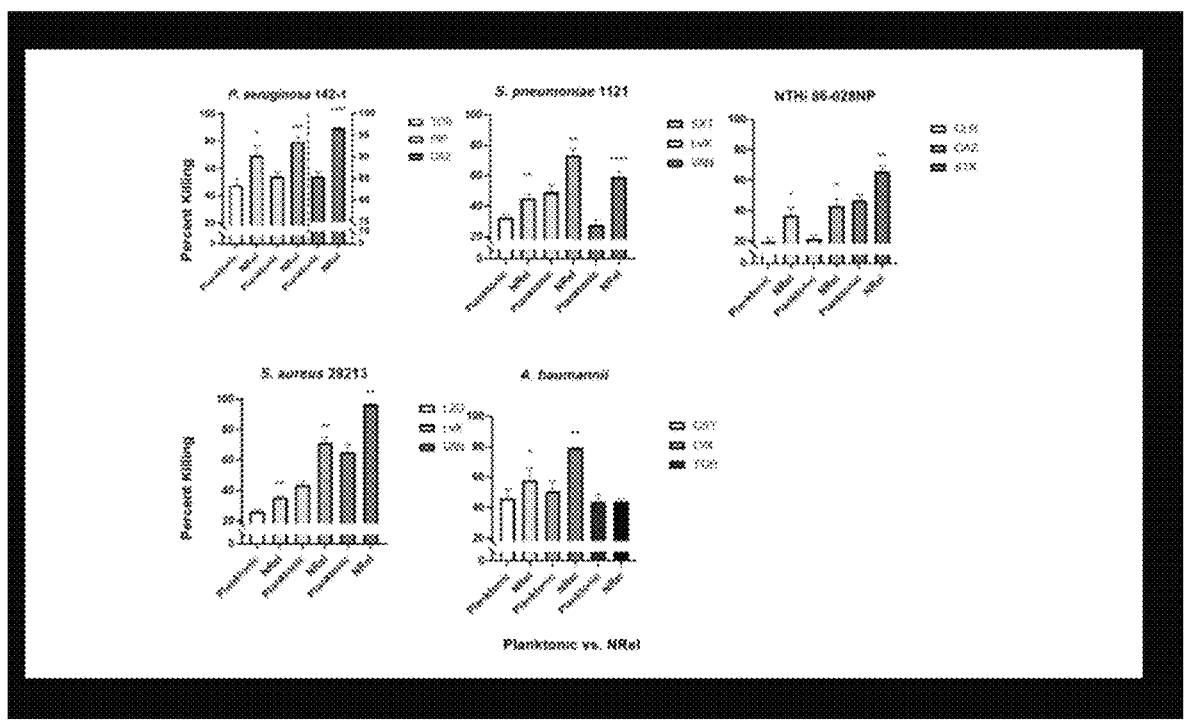
FIGS. 11A and 11B show relative percent killing of planktonic versus anti-DNABII NRel of five diverse species of human pathogens by each of the three current top-line antibiotics used to treat individuals with disease due to the indicated pathogen. Using the methods described herein, planktonic bacteria were recovered mid-log phase. NRel were induced by incubation of 16-hour biofilms with HuTipMab for 30 minutes. Planktonic and NRel populations were then incubated with each of three top-line antibiotics for 2 hours to determine relative percent killing. In each example presented here, the NRel for each of five pathogens so far was killed significantly greater than their planktonic counterparts and by each of the three top-line antibiotics (with the exception that *A. baumanii* NRel were not killed significantly greater by tobramycin under these conditions), however two important observations: There were differences in terms of which of the three top-line antibiotics would likely be best for the patient in terms of relative benefit which thereby could be an important clinically relevant new finding to better guide patient treatment strategy. Some antibiotics were so effective at killing the planktonic bacteria, that in order to show that the NRel were significantly more sensitive, a dose of antibiotic that was less than the MIC was used. See boxed data in FIG. 11B for NTHI and *S. aureus*. Typically in these assays, a dose of antibiotic that kills ≤50% planktonic bacteria is desired by us to be used to compare with relative killing of NRel, so in the two boxed cases, where the first dose tried killed ≥70% of planktonic, when reduced, we were able to clearly show that NRel were significantly more sensitive to killing by the indicated antibiotic.
Figure 11B:
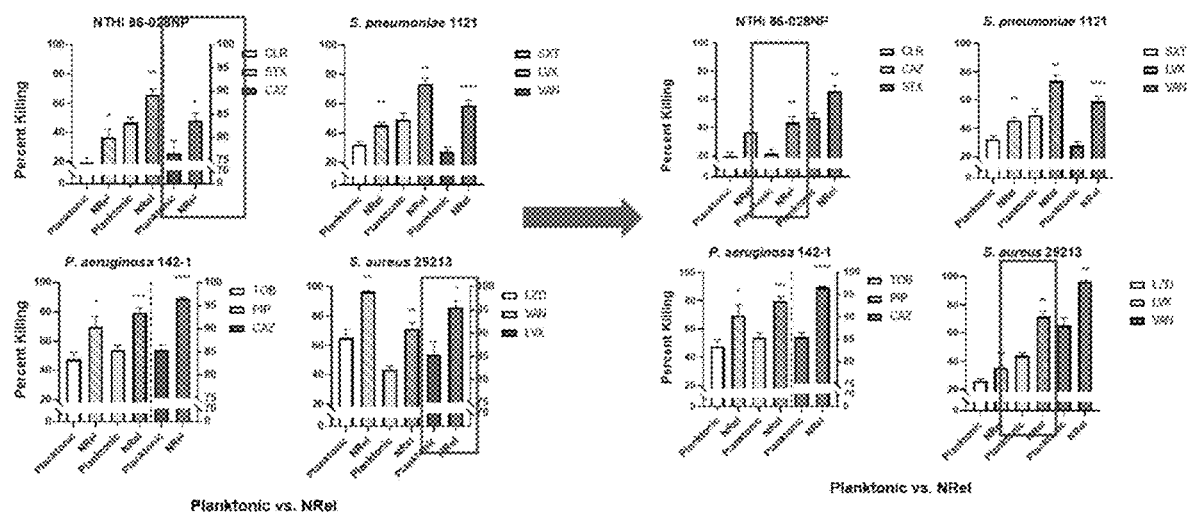
Figure 12:
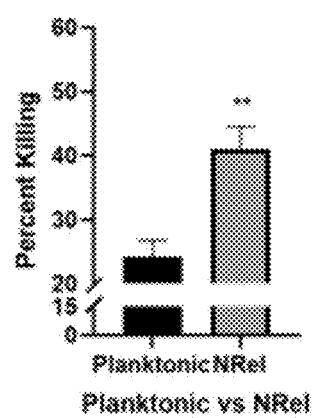
FIG. 12 shows killing of a clinical isolate of *P. aeruginosa* recovered recently from the sputum of a pediatric patient with CF that is highly resistant to killing by tobramycin (the standard of care for individuals with CF). The MIC for planktonic *P. aeruginosa* isolate JG1 is 4086 µg tobramycin/ml which indicates the tremendous challenge that would be associated with treating this individual given that planktonic bacteria are the most sensitive to killing whereas those resident within a biofilm typically require a 1000× greater concentration. Here both the planktonic and anti-DNABII NRel of JG1 were incubated with ¼ of the indicated MIC of tobramycin. Whereas at this dose, only ~25% of planktonic JG1 were killed, the NRel were significantly more sensitive to killing [n=3]. Using a ¼ MIC tobramycin dose, NRel were killed significantly better by tobramycin, the drug of choice for individuals with cystic fibrosis. ** denotes p≤0.01.
Figure 13:
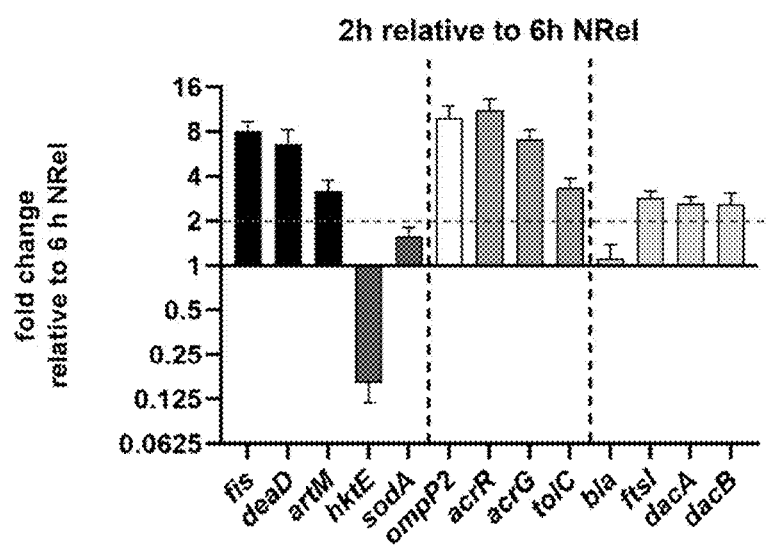
FIG. 13 show transcriptional profiling data for anti-DNABII NRel that compares those recovered 2 hr after exposure to anti-DNABII serum (e.g. those that were shown in FIG. 9 to be highly significant sensitivity to killing by AC) to those recovered at 6 hr post exposure (significant difference from Non Associated population is now gone). These data provide additional data in support of the distinct phenotype of NRel bacteria.

The increased abundance of ribosomal proteins observed in the anti-IHF NRel proteomic profile is also characteristic of bacteria in lag phase of growth (Rolfe et al., 2012). To determine whether anti-IHF NRel showed other similarities with lag phase bacteria, Applicant used qRT-PCR to examine the expression of three genes canonically expressed by bacteria in lag phase (Rolfe et al., 2012). Expression of deaD), artM, and fis was significantly (>2-fold) upregulated in anti-IHF NRel vs. planktonic NTHI (FIG. 6A). Interestingly, for all three of these genes, the fold increase in transcript abundance over planktonic NTHI was significantly greater for anti-IHF vs. anti-rsPilA NRel (P<0.05). Thus, that anti-IHF NRel appeared to be released from biofilm residence in a state which mimicked lag phase, presented another significant difference between the anti-IHF and anti-rsPilA phenotypes (Table 2), and again suggested that physical collapse of the biofilm structure resulted in rapid release while NTHI was metabolically more quiescent than anti-rsPilA NRel.

Because the proteomic expression profiles of the two NRel were different from each other (FIG. 2A), Applicant next conducted a direct comparison of DEPs between the two NRel populations as depicted by volcano plot (FIG. 2C & 2D). Fifty-one DEPs with >1.5-fold increase or decrease were identified amongst anti-IHF NRel versus anti-rsPilA NRel (FIG. 2C & Table 2). Of these, 15 proteins (29.4%) demonstrated a >1.5-fold increase in expression by anti-IHF NRel compared to anti-rsPilA NRel, and these proteins included five of the 30S and 50S ribosomal proteins described prior. Also, OMP P6 was more abundant in anti-IHF NRel compared to anti-rsPilA NRel. DEPs with a >1.5-fold decrease in the anti-IHF NRel compared to anti-rsPilA NRel (e.g. greater abundance in anti-rsPilA NRel) were characteristic of the abundantly expressed tryptophan biosynthesis proteins. These distinctions were in addition to relative differences in lipid metabolism proteins that had already been identified as decreased in expression in the anti-IHF NRel population compared to planktonic NTHI. Notably, this direct comparison of the two NRel proteomic expression profiles also revealed a significant increase in the peptidoglycan synthesis protein, MurB (Nikolaidis et al., 2014), within the anti-IHF NRel DEPs compared to anti-rsPilA NRel, which further suggested the altered cell envelope composition of the anti-IHF NRels (Table 2).

Anti-rsPilA or Anti-IHF NRel were Significantly More Sensitive to Killing by a Specific Antibiotic than Planktonic NTHI With the observed significant differences in relative expression of distinct proteins between the two NRel populations demonstrated, Applicant next examined how these differences altered phenotypic character. As bacteria newly released from a biofilm are typically more sensitive to killing by antibiotics than their planktonic counterparts (Brockson et al., 2014; Chambers et al., 2017; Goodwine et al., 2019; Mokrzan et al., 2018), Applicant assessed the sensitivity of NRel NTHI to TMP-SMX or to AMC, as these represent antibiotics commonly prescribed for NTHI-induced OM and respiratory infections (Harrison et al., 2009; K et al., 2017; Pelton, 2020; Sethi and Murphy, 2008; Tristram et al., 2007; Wald and DeMuri, 2018; Wasserman and Gerber, 2017). Applicant compared the anti-rsPilA NRel and anti-IHF NRel susceptibilities to killing by TMP-SMX or AMC, to that of both biofilm-resident NTHI (canonically highly resistant) and to planktonic NTHI grown to mid-log phase of growth (canonically sensitive and representative of the population commonly used to determine MIC values in clinical microbiology laboratories) (FIG. 3A). To control for differences in the numbers of NTHI released by exposure to anti-IHF IgG for 15 min or by anti-rsPilA IgG for 6 h (see FIG. 1), Applicant adjusted the density of the planktonic NTHI in each experiment to match that of either the anti-IHF or anti-rsPilA NRel population. After Applicant identified the concentrations of AMC or TMP-SMX needed to reproducibly kill ~25% of planktonic NTHI at each bacterial density, Applicant then used these concentrations to assess relative killing of the corresponding NRel or biofilm-resident NTHI.

As expected, anti-rsPilA NRel were significantly more sensitive than biofilm-resident NTHI to killing by either TMP-SMX or AMC (P≤0.0001) (FIG. 3B & FIG. 3C). Notably however, sensitivity of anti-rsPilA NRel to killing by TMP-SMX was significantly greater compared to that for planktonic NTHI (P≤0.001) after only 2 h of antibiotic exposure (FIG. 3B). In contrast, anti-rsPilA NRel were only equally as sensitive as their planktonic counterparts to killing by the β-lactam antibiotic AMC (FIG. 3C). Applicant then similarly evaluated anti-IHF NRel and found that they too were significantly more sensitive than biofilm-resident NTHI to killing by either TMP-SMX or AMC (P≤0.0001), again as expected (FIG. 3D & FIG. 3E). Intriguingly however, and in direct contrast to anti-rsPilA NRel, the anti-IHF NRel population was only equally as sensitive to TMP-SMX mediated killing as their planktonic counterparts (FIG. 3D), but significantly more sensitive to AMC (P≤0.0001) (FIG. 3E).

Bacterial sensitivity to antibiotic killing is the result of multiple processes that include drug uptake, efflux, and degradation, as well as the direct mechanism of antibiotic action (Kapoor et al., 2017). To identify possible mechanisms for the selectively enhanced antibiotic sensitivities of anti-IHF or anti-rsPilA NRel, Applicant used qRT-PCR to examine the relative expression of several genes likely to play a role in susceptibility or resistance to TMP-SMX or AMC. The protein targets of TMP and SMX, dihydrofolate reductase and dihydropteroate synthetase, are encoded by folA and folP, respectively; overproduction of FolA and FolP is associated with resistance to TMP-SMX (Huovinen, 2001). Accordingly, Applicant speculated that anti-rsPilA NRel NTHI would likely demonstrate less relative expression of folA and/or folP than anti-IHF NRels at the selected time points. Applicant's results confirmed this hypothesis, as folA and folP expression were both significantly reduced in anti-rsPilA vs. anti-IHF NRel (FIG. 6B, P<0.0001).

Efflux pumps enable bacteria to decrease the concentration of intracellular antibiotic. The EmrE efflux system transports β-lactam antibiotics in *Neisseria gonorrhoeae* (Du et al., 2018), and in *E. coli*, TMP-SMX exposure stimulates expression of the EmrAB efflux pump (Barrero et al., 2014), which suggested that the EmrAB efflux pump could influence NRel sensitivity to TMP-SMX. Applicant found that relative expression of emrA and emrB by anti-rsPilA NRel was significantly less that by anti-IHF NRel, consistent with the greater sensitivity of anti-rsPilA NRel to TMP-SMX (FIG. 6C, P<0.001). In contrast, the ArcAB efflux pump can transport β-lactam antibiotics and is under the control of the transcriptional repressor acrR (Anes et al., 2015). While enhanced AcrAB expression via acrR mutations has been linked to amoxicillin resistance in *Haemophilus* (https://aac.asm.org/content/51/7/2564.long), Applicant proposed that enhanced expression of acrR would likely have the opposite effect, enhanced susceptibility of NTHI to AMC. It was found that relative acrR expression was significantly greater by anti-IHF vs. anti-rsPilA NRel, consistent with the heightened sensitivity to AMC observed for anti-IHF NRel (FIG. 6C, P<0.0001).

Figures 4A, 4B, 4C, 4D:
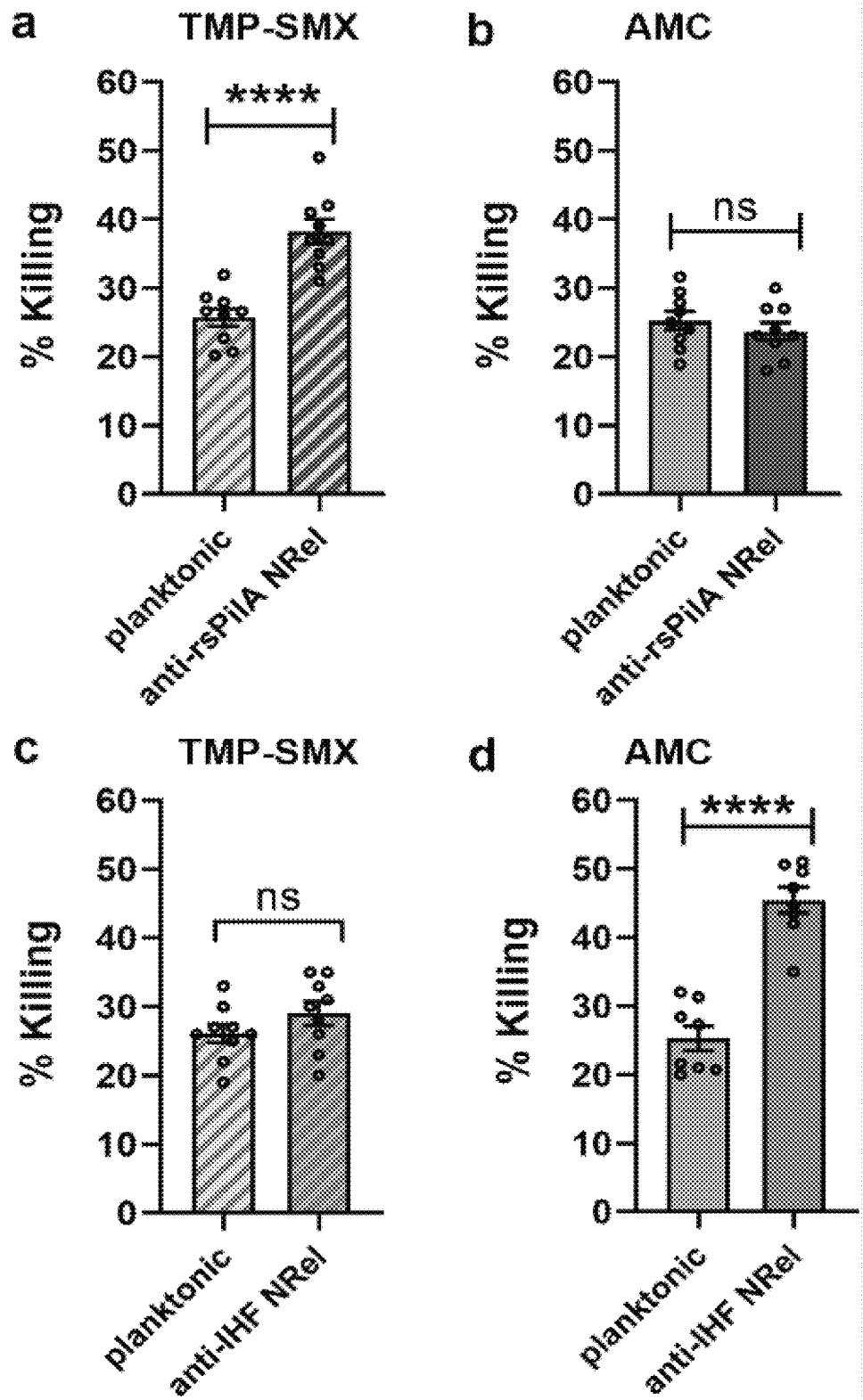
FIGS. 4A to 4D show enhanced sensitivity of anti-rsPilA or anti-IHF NRel NTHI to TMP-SMX or AMC, respectively, was independent of the timing of NTHI release from biofilm residence. Applicant exposed biofilms to rabbit polyclonal IgG isolated from either anti-rsPilA or anti-IHF serum for 2 h, then collected NRel NTHI and assayed for relative antibiotic sensitivity.

Taken together, Applicant's antibiotic sensitivity and transcript abundance data suggested that anti-rsPilA and anti-IHF NRel differed significantly in their relative antibiotic sensitivities due to the mechanism by which they were released from biofilm residence. However, Applicant was concerned that the difference in time required for maximal disruption (minutes) vs. dispersal (hours) might have also played a role in the observed phenotype. Thereby, the analysis of relative antibiotic sensitivities was repeated on time-matched NRel populations recovered after incubation with either anti-rsPilA or anti-IHF IgG for 2 h, a timepoint approximately midway between the times of maximal release for both antibodies. Similar to the results shown in FIG. 3, anti-rsPilA NRel were significantly more susceptible to killing by TMP-SMX (P≤0.0001) (FIG. 4A), and equally susceptible to killing by AMC, as planktonic NTHI (FIG. 4B). Moreover, time-matched anti-IHF NRel were again equally susceptible to killing by TMP-SMX (FIG. 4C) and significantly more susceptible to killing by AMC (P≤0.0001) (FIG. 4D), compared to planktonic NTHI. These results further support that the distinct antibiotic sensitivity phenotypes shown resulted from the two different mechanisms of release, dispersal vs. disruption.

To date, Applicant has shown extensive differences between the two mechanisms and outcomes of anti-rsPilA or anti-DNABII antibody-mediated release of biofilm-resident bacteria to the NRel state (Table 3). New data presented here added additional phenotypic distinctions between anti-rsPilA and anti-IHF NRel, wherein these two genetically identical populations exhibited not only distinctive proteomic and targeted transcriptomic expression profiles but also revealed that they were released from biofilm residence in distinct phases of growth and further, were released as either aggregates vs. as individual cells. Moreover, the two NRel populations demonstrated significantly increased, but different susceptibilities to killing by either a sulfonamide or a β-lactam antibiotic when compared to planktonic NTHI, both of which are first-line antibiotics recommended for treatment of NTHI-induced diseases.

DISCUSSION

Historically, the development paths for vaccines and those for antibiotics have proceeded in parallel, with one focused on prevention and the other on treatment (Tagliabue and Rappuoli, 2018). Whereas this strategy has indeed been successful for many diseases, the world now faces the issue of multiple chronic and recurrent infections for which neither path has yet achieved overall success. There are widely acknowledged obstacles to progress in this regard, none the least of which is the typically inherently slow vaccine development process (Koff and Schenkelberg, 2019). Similarly, there are tremendous challenges to the antibiotic development pathway, with no clinically approved truly new class of drug introduced for >30 years, despite extensive effort necessitated by a worrisome rapid increase in the rise of multi-antibiotic resistant bacteria worldwide (2017a; Ribeiro da Cunha et al., 2019). These obstacles to progress are understandable given the complex and difficult-to-treat nature of chronic diseases, which has confounded both discovery pathways. Such persistent and recurrent infections are attributable to causative agents that form biofilms wherein the resident bacteria have a unique transcriptome and a highly recalcitrant phenotype that renders them resistant to antibiotics and host immune effectors that readily kill their planktonic counterparts (Ahearn et al., 2017; Hall and Mah, 2017; Pang et al., 2012; Sharma et al., 2019; Silva and Sillankorva, 2019; Stewart, 2002). Applicant's advances in the recognition and understanding of the NRel phenotype now provide us with the opportunity to merge aspects of these development pathways to consider the use of therapeutic antibodies to release bacteria from the recalcitrant biofilm-residence into a state that is now markedly more vulnerable to killing.

Applicant previously showed that established NTHI biofilms concurrently exposed to both antiserum against a bacterial DNABII protein and an antibiotic were significantly more sensitive to killing by three antibiotics commonly used to treat OM (e.g. ampicillin, AMC and cefdinir) at concentrations ≥4-fold below the MIC, compared to their planktonic counterparts (Brockson et al., 2014). Applicant also showed that both NRel NTHI and NRel *M. catarrhalis* are more susceptible to TMP-SMX or clarithromycin, respectively, when released from a dual-species biofilm by incubation with anti-rsPilA, than those from growth on agar (Mokrzan et al., 2018). Given these previous observations, the disclosed studies aim to begin to understand the relative phenotypes of the two NRel populations as induced by the specifically targeted anti-rsPilA and anti-IHFsera, which release NTHI from biofilm residence by discrete mechanisms as this could have a notable influence on relative clinical approach to best mediate eradication of the resultant NRel population.

In this study, Applicant characterized anti-rsPilA and anti-IHF NRel and showed that their relative proteomic expression profiles, relative expression of targeted genes and sensitivity to killing by antibiotics were distinct not only from planktonically grown NTHI, but importantly, also from each other. Although the kinetics of release by anti-IHF-mediated disruption vs. anti-rsPilA-mediated dispersal are clearly different, Applicant's results strongly suggest that the observed differences in NRel phenotype were dependent on the specific antibody that mediated release from biofilm residence. The proteomic expression profiles provided a snapshot in time of the total released NRel populations. The anti-rsPilA NRel population proteomic profile was defined by an adaptive state of energy metabolism & conversion and amino acid transport & metabolism in response to their being induced to actively disperse from the biofilm. This adaptive metabolic state is likely somewhat more heterogeneous than anti-IHF NRel NTHI due to the more gradual release of cells as they actively disperse from the biofilm due to expression of both AI-2 and the Type IV twitching pilus over the 6 h incubation period. Nonetheless, the adaptive metabolic state of this anti-rsPilA NRel population was very similar to that described for other genera (e.g. *S. pneumoniae*, *K. pneumoniae*, and *P. aeruginosa*) in response to release from a biofilm and thereby does not appear to be atypical (Guilhen et al., 2016; Pettigrew et al., 2014; Rumbaugh and Sauer, 2020).

In analysis of the anti-IHF NRel population, Applicant found that it was defined by an increased production of ribosomal proteins with a concurrent decrease in LOS modification, cell membrane maintenance and lipid metabolism proteins. The enrichment of ribosomal proteins suggested that the anti-IHF NRel population was poised for protein synthesis with an altered membrane composition in response to rapid passive release en masse into the surrounding milieu. As such, anti-IHF NRel might be expected to still largely resemble biofilm-resident NTHI bacteria. Indeed, targeted transcriptomics indicated that anti-IHF NRel were in a state of growth similar to lag phase. Nonetheless, the anti-IHF NRel phenotype was also clearly different from that of biofilm-resident NTHI, as revealed by their significantly greater killing by both sulfonamide and β-lactam antibiotics compared to biofilm-resident NTHI.

Applicant shows herein for the first time that these NRel populations displayed unique enhanced sensitivity to killing by a different class of antibiotic dependent on whether they had been released from biofilm residence by either dispersal (e.g. via anti-rsPilA) or disruption (e.g. via anti-IHF). These differences cannot be explained by a direct effect of either anti-rsPilA or anti-IHF on NRel NTHI, since neither NTHI viability or susceptibility to killing by either of these antibiotics is affected by incubation with either antibody (Brockson et al., 2014; Mokrzan et al., 2018). Collectively, the two resultant NRel populations showed significant differences in relative proteomic expression profiles, targeted transcriptomic profiles, character of release from biofilm residence (both growth phase and as single cells vs. aggregates), and antibiotic sensitivities.

The anti-rsPilA NRel adaptive amino acid transport & metabolism state provided insight into the mechanism of this population's uniquely increased susceptibility to TMP-SMX, because the sulfonamide class of antibiotic targets the folic acid synthesis pathway involved in amino acid synthesis (Fernandez-Villa et al., 2019). Also, compared to anti-IHF NRel, the lower relative expression of folA and folP, which encode the protein targets for TMP and SMX, respectively, together with lower expression of emrA and emrB, which encode subunits of the EmrAB efflux pump that transports TMP-SMX out of the cell, also supported the greater sensitivity to TMP-SMX of anti-rsPilA vs. anti-IHF NRels. Similarly, the differences noted in the anti-IHF NRel lipid metabolism and cell membrane composition proteins supported the observed increased sensitivity to AMC, wherein the modified membrane content could have altered membrane permeability to allow greater access of the β-lactam antibiotic to the periplasm where they could bind to the penicillin binding proteins to prevent peptidoglycan crosslinking (Delcour, 2009). Additional insight into the mechanism of unique sensitivity to the β-lactam antibiotic in the anti-IHF NRel population was provided by the increased abundance of the peptidoglycan synthesis protein MurB, which suggested that the anti-IHF NRel were actively synthesizing peptidoglycan which would support their greater susceptibility to the action of a β-lactam antibiotic (Delcour, 2009; Zapun et al., 2008). The upregulation of acrR, which represses expression of AcrAB efflux pump, likely results in increased AMC concentration within the anti-IHF NRel and enhanced killing. The upregulation of fis in the anti-IHF NRel population presents yet another possible mechanism for increased sensitivity to AMC, since both *P. aeruginosa* and *E. coli* mutants with a nonfunctional fis gene showed enhanced resistance to β-lactam antibiotic (Grkovic et al., 2001; Long et al., 2020; Martin and Rosner, 1997).

Taken together, this data suggested that the NRel phenotype is not 'generic,' but rather highly distinct and dependent on the antibody-mediated mechanism of release of NTHI from biofilm residence.

In a world 'running out of antibiotics' there is a push to identify new antimicrobials, institute antibiotic stewardship and educate the public as to the dangers of inappropriate antibiotic use (Piltcher et al., 2018). This situation has inspired many to attack this problem in novel and creative ways. In a Nature commentary, Rappuoli, Bloom and Black (Rappuoli et al., 2017) suggested the combination of the power of vaccine-induced antibodies with a more appropriate use of antibiotics as our "last hope against multi-drug resistant bacteria and persistent disease". Whereas their focus was on antibodies that reduce carriage, and thus transmission of antibiotic-resistant bacteria (Rappuoli et al., 2017), Applicant envisions use of specifically induced antibodies to release biofilm-resident NTHI from these highly resistant communities so they can be killed by host immune effectors and when necessary, traditional antibiotics, with the latter now used at a markedly reduced dose and for a shorter course due to the highly sensitive phenotype of NRel NTHI. An additional potential benefit of a less frequent antibiotic treatment regimen is reduction of off-target side effects and other undesirable sequelae of oral antibiotic use; which includes development of antibiotic resistance (Patini et al., 2020; Tagliabue and Rappuoli, 2018) and/or disruption of the gut microbiome (Bailey et al., 2020; Gillies et al., 2015; Kuehn et al., 2015; MacPherson et al., 2018; Pallav et al., 2014).

Herein, Applicant provides basis for this strategy to treat biofilm-associated diseases caused by NTHI via use of NRel-inducing antibodies directed against unique biofilm associated targets of this important human pathogen. Moreover, use of the species independent anti-DNABII approach broadens the potential use of this combination strategy for treatment of many other diseases caused by diverse human pathogens wherein a biofilm similarly contributes significantly to pathogenesis, chronicity, recurrence and recalcitrance to treatment.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated.

Other substitutions, modifications, changes and omissions may be made in the design, operating conditions and arrangement of the embodiments without departing from the scope of the present disclosure as expressed in the appended claims.

Throughout this disclosure, technical publications are reference by date and/or first author. The full bibliographic citations for each is provided below. All patent and technical publications are incorporated by reference herein.

Additional enabling details can be found in the following references (which are referenced above):

2017a. Antibacterial agents in clinical development: an analysis of the antibacterial clinical development pipeline, including tuberculosis. Geneva: World Health Organization. https://apps.who.int/iris/bitstream/handle/10665/258965/WHO-EMP-IAU-2017.11-eng.pdf;jsessionid=4C4B74B963CED463A94DD2DE9CB5EACA?sequence=1

2017b. The world is running out of antibiotics, WHO report confirms. Geneva, World Health Organization. https://www.who.int/news-room/detail/20-09-2017-the-world-is-running-out-of-antibiotics-who-report-confirms Ahearn, C. P., Gallo, M. C., Murphy, T. F., 2017. Insights on persistent airway infection by non-typeable *Haemophilus influenzae* in chronic obstructive pulmonary disease. Pathog Dis 75. doi: 10.1093/femspd/ftx042

Andre, F. E., Booy, R., Bock, H. L., Clemens, J., Datta, S. K., John, T. J., Lee, B. W., Lolekha, S., Peltola, H., Ruff, T. A., Santosham, M., Schmitt, H. J., 2008. Vaccination greatly reduces disease, disability, death and inequity worldwide. Bull World Health Organ 86, 140-146. doi: 10.2471/blt.07.040089

Anes, J., McCusker, M. P., Fanning, S., Martins, M., 2015. The ins and outs of RND efflux pumps in *Escherichia coli*. Front Microbiol 6, 587. doi: 10.3389/fmicb.2015.00587

Armbruster, C. E., Hong, W., Pang, B., Dew, K. E., Juneau, R. A., Byrd, M. S., Love, C. F., Kock, N. D., Swords, W. E., 2009. LuxS promotes biofilm maturation and persistence of nontypeable *Haemophilus influenzae* in vivo via modulation of lipooligosaccharides on the bacterial surface. Infect Immun 77, 4081-4091. doi: 10.1128/IAI.00320-09

Armbruster, C. E., Hong, W., Pang, B., Weimer, K. E., Juneau, R. A., Turner, J., Swords, W. E., 2010. Indirect pathogenicity of *Haemophilus influenzae* and *Moraxella catarrhalis* in polymicrobial otitis media occurs via interspecies quorum signaling. mBio 1, e00102-00110. doi: 10.1128/mBio.00102-10

Armbruster, C. E., Pang, B., Murrah, K., Juneau, R. A., Perez, A. C., Weimer, K. E., Swords, W. E., 2011. RbsB (NTHI_0632) mediates quorum signal uptake in nontypeable *Haemophilus influenzae* strain 86-028NP. Mol Microbiol 82, 836-850. doi: 10.1111/j.1365-2958.2011.07831.x Aziz, A., Sarovich, D. S., Nosworthy, E., Beissbarth, J., Chang, A. B., Smith-Vaughan, H., Price, E. P., Harris, T. M., 2019. Molecular signatures of non-typeable *Haemophilus influenzae* lung adaptation in pediatric chronic lung disease. Front Microbiol 10, 1622. doi: 10.3389/fmicb.2019.01622

Bailey, M. T., Lauber, C. L., Novotny, L. A., Goodman, S. D., Bakaletz, L. O., 2020. Immunization with a biofilm-disrupting nontypeable *Haemophilus influenzae* vaccine antigen did not alter the gut microbiome in chinchillas, unlike oral delivery of a broad-spectrum antibiotic commonly used for otitis media. mSphere 5, e00296-00220. doi: 10.1128/mSphere.00296-20

Bakaletz, L. O., Baker, B. D., Jurcisek, J. A., Harrison, A., Novotny, L. A., Bookwalter, J. E., Mungur, R., Munson, R. S., Jr., 2005. Demonstration of type IV pilus expression and a twitching phenotype by *Haemophilus influenzae*. Infect Immun 73, 1635-1643. doi: 10.1128/IAI.73.3.1635-1643.2005

Barkai, G., Leibovitz, E., Givon-Lavi, N., Dagan, R., 2009. Potential contribution by nontypable *Haemophilus influenzae* in protracted and recurrent acute otitis media. Pediatr Infect Dis J 28, 466-471. doi: 10.1097/inf.0b013e3181950c74

Barrero, M. A., Pietralonga, P. A., Schwarz, D. G., Silva, A., Jr., Paula, S. O., Moreira, M. A., 2014. Effect of the inhibitors phenylalanine arginyl ss-naphthylamide (PAssN) and 1-(1-naphthylmethyl)-piperazine (NMP) on expression of genes in multidrug efflux systems of *Escherichia coli* isolates from bovine mastitis. Res Vet Sci 97, 176-181. doi: 10.1016/j.rvsc.2014.05.013

Beekmann, S. E., Heilmann, K. P., Richter, S. S., Garcia-de-Lomas, J., Doern, G. V., Group, G. S., 2005. Antimicrobial resistance in *Streptococcus pneumoniae*, *Haemophilus influenzae*, *Moraxella catarrhalis* and group A beta-haemolytic streptococci in 2002-2003. Results of the multinational GRASP Surveillance Program. Int J Antimicrob Agents 25, 148-156. doi: 10.1016/j.ijantimicag.2004.09.016

Belfield, K., Bayston, R., Birchall, J. P., Daniel, M., 2015. Do orally administered antibiotics reach concentrations in the middle ear sufficient to eradicate planktonic and biofilm bacteria? A review. Int J Pediatr Otorhinolaryngol 79, 296-300. doi: 10.1016/j.ijporl.2015.01.003

Brockson, M. E., Novotny, L. A., Mokrzan, E. M., Malhotra, S., Jurcisek, J. A., Akbar, R., Devaraj, A., Goodman, S. D., Bakaletz, L. O., 2014. Evaluation of the kinetics and mechanism of action of anti-integration host factor-mediated disruption of bacterial biofilms. Mol Microbiol 93, 1246-1258. doi: 10.1111/mmi.12735

Cardines, R., Giufre, M., Pompilio, A., Fiscarelli, E., Ricciotti, G., Di Bonaventura, G., Cerquetti, M., 2012. *Haemophilus influenzae* in children with cystic fibrosis: antimicrobial susceptibility, molecular epidemiology, distribution of adhesins and biofilm formation. Int J Med Microbiol 302, 45-52. doi: 10.1016/j.ijmm.2011.08.003

Carruthers, M. D., Tracy, E. N., Dickson, A. C., Ganser, K. B., Munson, R. S., Jr., Bakaletz, L. O., 2012. Biological roles of nontypeable *Haemophilus influenzae* type IV pilus proteins encoded by the pil and com operons. J Bacteriol 194, 1927-1933. doi: 10.1128/JB.06540-11

Chambers, J. R., Cherny, K. E., Sauer, K., 2017. Susceptibility of *Pseudomonas aeruginosa* dispersed cells to antimicrobial agents is dependent on the dispersion cue and class of the antimicrobial agent used. Antimicrob Agents Chemother 61, e00846-00817. doi: 10.1128/AAC.00846-17

Chua, S. L., Liu, Y., Yam, J. K., Chen, Y., Vejborg, R. M., Tan, B. G., Kjelleberg, S., Tolker-Nielsen, T., Givskov, M., Yang, L., 2014. Dispersed cells represent a distinct stage in the transition from bacterial biofilm to planktonic lifestyles. Nat Commun 5, 4462. doi: 10.1038/ncomms5462

Cleary, D., Devine, V., Morris, D., Osman, K., Gladstone, R., Bentley, S., Faust, S., Clarke, S., 2018. Pneumococcal vaccine impacts on the population genomics of non-typeable *Haemophilus influenzae*. Microb Genom 4, e000209. doi: 10.1099/mgen.0.000209

Costerton, J. W., Stewart, P. S., Greenberg, E. P., 1999. Bacterial biofilms: a common cause of persistent infections. Science 284, 1318-1322. doi: 10.1126/science.284.5418.1318

D'Andrea, M. M., Lau, G. W., 2020. DNABII targeting antibodies as vaccines against biofilm diseases. EBioMedicine 58, 102921. doi: 10.1016/j.ebiom.2020.102921

Daines, D. A., Bothwell, M., Furrer, J., Unrath, W., Nelson, K., Jarisch, J., Melrose, N., Greiner, L., Apicella, M., Smith, A. L., 2005. *Haemophilus influenzae* luxS mutants form a biofilm and have increased virulence. Microb Pathog 39, 87-96. doi: 10.1016/j.micpath.2005.06.003

Das, J., Mokrzan, E., Lakhani, V., Rosas, L., Jurcisek, J. A., Ray, W. C., Bakaletz, L. O., 2017. Extracellular DNA and type IV pilus expression regulate the structure and kinetics of biofilm formation by nontypeable *Haemophilus influenzae*. mBio 8, e01466-01417. doi: 10.1128/mBio.01466-17

Delcour, A. H., 2009. Outer membrane permeability and antibiotic resistance. Biochim Biophys Acta 1794, 808-816. doi: 10.1016/j.bbapap.2008.11.005

Devaraj, A., Buzzo, J., Rocco, C. J., Bakaletz, L. O., Goodman, S. D., 2018. The DNABII family of proteins is comprised of the only nucleoid associated proteins required for nontypeable *Haemophilus influenzae* biofilm structure. MicrobiologyOpen 7, e00563. doi: 10.1002/mbo3.563

Devaraj, A., Justice, S. S., Bakaletz, L. O., Goodman, S. D., 2015. DNABII proteins play a central role in UPEC biofilm structure. Mol Microbiol 96, 1119-1135. doi: 10.1111/mmi.12994

Dongari-Bagtzoglou, A., 2008. Pathogenesis of mucosal biofilm infections: challenges and progress. Expert Rev Anti Infect Ther 6, 201-208. doi: 10.1586/14787210.6.2.201

Du, D., Wang-Kan, X., Neuberger, A., van Veen, H. W., Pos, K. M., Piddock, L. J. V., Luisi, B. F., 2018. Multidrug efflux pumps: structure, function and regulation. Nat Rev Microbiol 16, 523-539. doi: 10.1038/s41579-018-0048-6

Fernandez-Villa, D., Aguilar, M. R., Rojo, L., 2019. Folic acid antagonists: Antimicrobial and immunomodulating mechanisms and applications. Int J Mol Sci 20, 4996. doi: 10.3390/ijms20204996

Flemming, H. C., Wingender, J., 2010. The biofilm matrix. Nat Rev Microbiol 8, 623-633. doi: 10.1038/nrmicro2415

Freire, M. O., Devaraj, A., Young, A., Navarro, J. B., Downey, J. S., Chen, C., Bakaletz, L. O., Zadeh, H. H., Goodman, S. D., 2017. A bacterial-biofilm-induced oral osteolytic infection can be successfully treated by immuno-targeting an extracellular nucleoid-associated protein. Mol Oral Microbiol 32, 74-88. doi: 10.1111/omi.12155

Gilbert, J. A., Blaser, M. J., Caporaso, J. G., Jansson, J. K., Lynch, S. V., Knight, R., 2018. Current understanding of the human microbiome. Nat Med 24, 392-400. doi: 10.1038/nm.4517

Gillies, M., Ranakusuma, A., Hoffmann, T., Thorning, S., McGuire, T., Glasziou, P., Del Mar, C., 2015. Common harms from amoxicillin: a systematic review and meta-analysis of randomized placebo-controlled trials for any indication. CMAJ 187, E21-E31. doi: 10.1503/cmaj.140848

Goodman, S. D., Obergfell, K. P., Jurcisek, J. A., Novotny, L. A., Downey, J. S., Ayala, E. A., Tjokro, N., Li, B., Justice, S. S., Bakaletz, L. O., 2011. Biofilms can be dispersed by focusing the immune system on a common family of bacterial nucleoid-associated proteins. Mucosal Immunol 4, 625-637. doi: 10.1038/mi.2011.27

Goodwine, J., Gil, J., Doiron, A., Valdes, J., Solis, M., Higa, A., Davis, S., Sauer, K., 2019. Pyruvate-depleting conditions induce biofilm dispersion and enhance the efficacy of antibiotics in killing biofilms in vitro and in vivo. Sci Rep 9, 3763. doi: 10.1038/s41598-019-40378-z Grevers, G., Wiedemann, S., Bohn, J. C., Blasius, R. W., Harder, T., Kroeniger, W., Vetter, V., Pircon, J. Y., Marano, C., 2012. Identification and characterization of the bacterial etiology of clinically problematic acute otitis media after tympanocentesis or spontaneous otorrhea in German children. BMC Infect Dis 12, 312. doi: 10.1186/1471-2334-12-312

Grkovic, S., Brown, M. H., Skurray, R. A., 2001. Transcriptional regulation of multidrug efflux pumps in bacteria. Semin Cell Dev Biol 12, 225-237. doi: 10.1006/scdb.2000.0248

Guilhen, C., Charbonnel, N., Parisot, N., Gueguen, N., Iltis, A., Forestier, C., Balestrino, D., 2016. Transcriptional profiling of *Klebsiella pneumoniae* defines signatures for planktonic, sessile and biofilm-dispersed cells. BMC Genomics 17, 237. doi: 10.1186/s12864-016-2557-x Hall, C. W., Mah, T. F., 2017. Molecular mechanisms of biofilm-based antibiotic resistance and tolerance in pathogenic bacteria. FEMS Microbiol Rev 41, 276-301. doi: 10.1093/femsre/fux010

Harrison, A., Dyer, D. W., Gillaspy, A., Ray, W. C., Mungur, R., Carson, M. B., Zhong, H., Gipson, J., Gipson, M., Johnson, L. S., Lewis, L., Bakaletz, L. O., Munson, R. S., Jr., 2005. Genomic sequence of an otitis media isolate of nontypeable *Haemophilus influenzae*: comparative study with *H. influenzae* serotype d, strain KW20. J Bacteriol 187, 4627-4636. doi: 10.1128/JB.187.13.4627-4636.2005

Harrison, C. J., Woods, C., Stout, G., Martin, B., Selvarangan, R., 2009. Susceptibilities of *Haemophilus influenzae*, *Streptococcus pneumoniae*, including serotype 19A, and *Moraxella catarrhalis* paediatric isolates from 2005 to 2007 to commonly used antibiotics. J Antimicrob Chemother 63, 511-519. doi: 10.1093/jac/dkn538

Hassan, F., 2013. Molecular mechanisms of *Moraxella catarrhalis*-induced otitis media. Curr Allergy Asthma Rep 13, 512-517. doi: 10.1007/s11882-013-0374-8

Huovinen, P., 2001. Resistance to trimethoprim-sulfamethoxazole. Clin Infect Dis 32, 1608-1614. doi: 10.1086/320532

Jurcisek, J. A., Bakaletz, L. O., 2007. Biofilms formed by nontypeable *Haemophilus influenzae* in vivo contain both double-stranded DNA and type IV pilin protein. J Bacteriol 189, 3868-3875. doi: 10.1128/JB.01935-06

Jurcisek, J. A., Bookwalter, J. E., Baker, B. D., Fernandez, S., Novotny, L. A., Munson, R. S., Jr., Bakaletz, L. O., 2007. The PilA protein of non-typeable *Haemophilus influenzae* plays a role in biofilm formation, adherence to epithelial cells and colonization of the mammalian upper respiratory tract. Mol Microbiol 65, 1288-1299. doi: 10.1111/j.1365-2958.2007.05864.x Jurcisek, J. A., Dickson, A. C., Bruggeman, M. E., Bakaletz, L. O., 2011. In vitro biofilm formation in an 8-well chamber slide. J Vis Exp 20, 2481. doi: 10.3791/2481

K, L. C. H., Akyol, S., Parkan, O. M., Dinc, G., Sav, H., Aydemir, G., 2017. Molecular characterization and antibiotic susceptibility of *Haemophilus influenzae* clinical isolates. Infez Med 25, 27-32.

Kamashev, D., Agapova, Y., Rastorguev, S., Talyzina, A. A., Boyko, K. M., Korzhenevskiy, D. A., Vlaskina, A., Vasilov, R., Timofeev, V. I., Rakitina, T. V., 2017. Comparison of histone-like HU protein DNA-binding properties and HU/IHF protein sequence alignment. PLOS One 12, e0188037. doi: 10.1371/journal.pone.0188037

Kaplan, E., Greene, N. P., Crow, A., Koronakis, V., 2018. Insights into bacterial lipoprotein trafficking from a structure of LolA bound to the LolC periplasmic domain. Proc Natl Acad Sci USA 115, E7389-E7397. doi: 10.1073/pnas.1806822115

Kapoor, G., Saigal, S., Elongavan, A., 2017. Action and resistance mechanisms of antibiotics: A guide for clinicians. J Anaesthesiol Clin Pharmacol 33, 300-305. doi: 10.4103/joacp.JOACP_349_15

Koff, W. C., Schenkelberg, T., 2019. The future of vaccine development. Vaccine. doi: 10.1016/j.vaccine.2019.07.101

Kuehn, J., Ismael, Z., Long, P. F., Barker, C. I., Sharland, M., 2015. Reported rates of diarrhea following oral penicillin therapy in pediatric clinical trials. J Pediatr Pharmacol Ther 20, 90-104. doi: 10.5863/1551-6776-20.2.90

Lamont, R. F., Moller Luef, B., Stener Jorgensen, J., 2020. Childhood inflammatory and metabolic disease following exposure to antibiotics in pregnancy, antenatally, intrapartum and neonatally. F1000Res 9, F1000 Faculty Rev-1144. doi: 10.12688/f1000research. 19954.1

Lê, S., Josse, J., Husson, F., 2008. FactoMineR: A package for multivariate analysis. J. Stat. Softw. 25, 1-18. doi: 10.18637/jss.v025.i01

Leibovitz, E., Broides, A., Greenberg, D., Newman, N., 2010. Current management of pediatric acute otitis media. Expert Rev Anti Infect Ther 8, 151-161. doi: 10.1586/eri.09.112

Long, Y., Fu, W., Wang, S., Deng, X., Jin, Y., Bai, F., Cheng, Z., Wu, W., 2020. Fis Contributes to resistance of *Pseudomonas aeruginosa* to ciprofloxacin by regulating pyocin synthesis. J Bacteriol 202. doi: 10.1128/JB.00064-20

MacPherson, C. W., Mathieu, O., Tremblay, J., Champagne, J., Nantel, A., Girard, S. A., Tompkins, T. A., 2018. Gut bacterial microbiota and its resistome rapidly recover to basal state levels after short-term amoxicillin-clavulanic acid treatment in healthy adults. Sci Rep 8, 11192. doi: 10.1038/s41598-018-29229-5

Marks, L. R., Davidson, B. A., Knight, P. R., Hakansson, A. P., 2013. Interkingdom signaling induces *Streptococcus pneumoniae* biofilm dispersion and transition from asymptomatic colonization to disease. mBio 4, e00438-00413. doi: 10.1128/mBio.00438-13

Martin, R. G., Rosner, J. L., 1997. Fis, an accessory factor for transcriptional activation of the mar (multiple antibiotic resistance) promoter of *Escherichia coli* in the presence of the activator MarA, SoxS, or Rob. J Bacteriol 179, 7410-7419. doi: 10.1128/jb.179.23.7410-7419.1997

Mittal, R., Parrish, J. M., Soni, M., Mittal, J., Mathee, K., 2018. Microbial otitis media: recent advancements in treatment, current challenges and opportunities. J Med Microbiol 67, 1417-1425. doi: 10.1099/jmm.0.000810

Mokrzan, E. M., Johnson, T. J., Bakaletz, L. O., 2019. Expression of the nontypeable *Haemophilus influenzae* type IV pilus is stimulated by coculture with host respiratory tract epithelial cells. Infect Immun 87, e00704-00719. doi: 10.1128/IAI.00704-19

Mokrzan, E. M., Novotny, L. A., Brockman, K. L., Bakaletz, L. O., 2018. Antibodies against the majority subunit (PilA) of the type IV pilus of nontypeable *Haemophilus influenzae* disperse *Moraxella catarrhalis* from a dual-species biofilm. mBio 9, e02423-02418. doi: 10.1128/mBio.02423-18

Mokrzan, E. M., Ward, M. O., Bakaletz, L. O., 2016. Type IV pilus expression is upregulated in nontypeable *Haemophilus influenzae* biofilms formed at the temperature of the human nasopharynx. J Bacteriol 198, 2619-2630. doi: 10.1128/JB.01022-15

Murphy, T. F., Kirkham, C., Lesse, A. J., 2006. Construction of a mutant and characterization of the role of the vaccine antigen P6 in outer membrane integrity of nontypeable *Haemophilus influenzae*. Infect Immun 74, 5169-5176. doi: 10.1128/IAI.00692-06

Nikolaidis, I., Favini-Stabile, S., Dessen, A., 2014. Resistance to antibiotics targeted to the bacterial cell wall. Protein Sci 23, 243-259. doi: 10.1002/pro.2414

Novotny, L. A., Adams, L. D., Kang, D. R., Wiet, G. J., Cai, X., Sethi, S., Murphy, T. F., Bakaletz, L. O., 2009. Epitope mapping immunodominant regions of the PilA protein of nontypeable *Haemophilus influenzae* (NTHI) to facilitate the design of two novel chimeric vaccine candidates. Vaccine 28, 279-289. doi: 10.1016/j.vaccine.2009.08.017

Novotny, L. A., Amer, A. O., Brockson, M. E., Goodman, S. D., Bakaletz, L. O., 2013a. Structural stability of *Burkholderia cenocepacia* biofilms is reliant on eDNA structure and presence of a bacterial nucleic acid binding protein. PLOS One 8, e67629. doi: 10.1371/journal.pone.0067629

Novotny, L. A., Clements, J. D., Bakaletz, L. O., 2013b. Kinetic analysis and evaluation of the mechanisms involved in the resolution of experimental nontypeable *Haemophilus influenzae*-induced otitis media after transcutaneous immunization. Vaccine 31, 3417-3426. doi: 10.1016/j.vaccine.2012.10.033

Novotny, L. A., Goodman, S. D., Bakaletz, L. O., 2019. Redirecting the immune response towards immunoprotective domains of a DNABII protein resolves experimental otitis media. NPJ Vaccines 4, 43. doi: 10.1038/s41541-019-0137-1

Novotny, L. A., Goodman, S. D., Bakaletz, L. O., 2020. Targeting a bacterial DNABII protein with a chimeric peptide immunogen or humanised monoclonal antibody to prevent or treat recalcitrant biofilm-mediated infections. EBioMedicine. doi: 10.1016/j.ebiom.2020.102867

Novotny, L. A., Jurcisek, J. A., Goodman, S. D., Bakaletz, L. O., 2016. Monoclonal antibodies against DNA-binding tips of DNABII proteins disrupt biofilms in vitro and induce bacterial clearance in vivo. EBioMedicine 10, 33-44. doi: 10.1016/j.ebiom.2016.06.022

Novotny, L. A., Jurcisek, J. A., Ward, M. O., Jr., Jordan, Z. B., Goodman, S. D., Bakaletz, L. O., 2015. Antibodies against the majority subunit of type IV Pili disperse nontypeable *Haemophilus influenzae* biofilms in a LuxS-dependent manner and confer therapeutic resolution of experimental otitis media. Mol Microbiol 96, 276-292. doi: 10.1111/mmi.12934

Pallav, K., Dowd, S. E., Villafuerte, J., Yang, X., Kabbani, T., Hansen, J., Dennis, M., Leffler, D. A., Newburg, D. S., Kelly, C. P., 2014. Effects of polysaccharopeptide from *Trametes versicolor* and amoxicillin on the gut microbiome of healthy volunteers: a randomized clinical trial. Gut Microbes 5, 458-467. doi: 10.4161/gmic.29558

Pang, B., Armbruster, C. E., Foster, G., Learman, B. S., Gandhi, U., Swords, W. E., 2018. Autoinducer 2 (AI-2) production by nontypeable *Haemophilus influenzae* 86-028NP promotes expression of a predicted glycosyltransferase that is a determinant of biofilm maturation, prevention of dispersal, and persistence in vivo. Infect Immun 86. doi: 10.1128/IAI.00506-18

Pang, B., Hong, W., Kock, N. D., Swords, W. E., 2012. Dps promotes survival of nontypeable *Haemophilus influenzae* in biofilm communities in vitro and resistance to clearance in vivo. Front Cell Infect Microbiol 2, 58. doi: 10.3389/fcimb.2012.00058

Parsons, J. B., Rock, C. O., 2013. Bacterial lipids: metabolism and membrane homeostasis. Prog Lipid Res 52, 249-276. doi: 10.1016/j.plipres.2013.02.002

Patini, R., Mangino, G., Martellacci, L., Quaranta, G., Masucci, L., Gallenzi, P., 2020. The effect of different antibiotic regimens on bacterial resistance: A systematic review. Antibiotics (Basel) 9, 22. doi: 10.3390/antibiotics9010022

Pelton, S., 2020. Acute otitis media in children: Treatment, in: Post, T. (Ed.), UpToDate, Waltham, M A.

Petrova, O. E., Sauer, K., 2016. Escaping the biofilm in more than one way: desorption, detachment or dispersion. Curr Opin Microbiol 30, 67-78. doi: 10.1016/j.mib.2016.01.004

Pettigrew, M. M., Marks, L. R., Kong, Y., Gent, J. F., Roche-Hakansson, H., Hakansson, A. P., 2014. Dynamic changes in the Streptococcus pneumoniae transcriptome during transition from biofilm formation to invasive disease upon influenza A virus infection. Infect Immun 82, 4607-4619. doi: 10.1128/IAI.02225-14

Piltcher, O. B., Kosugi, E. M., Sakano, E., Mion, O., Testa, J. R. G., Romano, F. R., Santos, M. C. J., Di Francesco, R. C., Mitre, E. I., Bezerra, T. F. P., Roithmann, R., Padua, F. G., Valera, F. C. P., Lubianca Neto, J. F., Sa, L. C. B., Pignatari, S. S. N., Avelino, M. A. G., Caixeta, J. A. S., Anselmo-Lima, W. T., Tamashiro, E., 2018. How to avoid the inappropriate use of antibiotics in upper respiratory tract infections? A position statement from an expert panel. Braz J Otorhinolaryngol 84, 265-279. doi: 10.1016/j.bjorl.2018.02.001

Poole, J., Foster, E., Chaloner, K., Hunt, J., Jennings, M. P., Bair, T., Knudtson, K., Christensen, E., Munson, R. S., Jr., Winokur, P. L., Apicella, M. A., 2013. Analysis of nontypeable Haemophilus influenzae phase-variable genes during experimental human nasopharyngeal colonization. J Infect Dis 208, 720-727. doi: 10.1093/infdis/jit240

Rappuoli, R., Bloom, D. E., Black, S., 2017. Deploy vaccines to fight superbugs. Nature 552, 165-167. doi: 10.1038/d41586-017-08323-0

Ribeiro da Cunha, B., Fonseca, L. P., Calado, C. R. C., 2019. Antibiotic discovery: Where have we come from, where do we go? Antibiotics (Basel) 8, 45. doi: 10.3390/antibiotics8020045

Rolfe, M. D., Rice, C. J., Lucchini, S., Pin, C., Thompson, A., Cameron, A. D., Alston, M., Stringer, M. F., Betts, R. P., Baranyi, J., Peck, M. W., Hinton, J. C., 2012. Lag phase is a distinct growth phase that prepares bacteria for exponential growth and involves transient metal accumulation. J Bacteriol 194, 686-701. doi: 10.1128/JB.06112-11

Rumbaugh, K. P., Sauer, K., 2020. Biofilm dispersion. Nat Rev Microbiol. doi: 10.1038/s41579-020-0385-0

Sauer, K., Cullen, M. C., Rickard, A. H., Zeef, L. A., Davies, D. G., Gilbert, P., 2004. Characterization of nutrient-induced dispersion in Pseudomonas aeruginosa PAO1 biofilm. J Bacteriol 186, 7312-7326. doi: 10.1128/JB.186.21.7312-7326.2004

Sethi, S., Murphy, T. F., 2008. Infection in the pathogenesis and course of chronic obstructive pulmonary disease. N Engl J Med 359, 2355-2365. doi: 10.1056/NEJMra0800353

Sharma, D., Misba, L., Khan, A. U., 2019. Antibiotics versus biofilm: an emerging battleground in microbial communities. Antimicrob Resist Infect Control 8, 76. doi: 10.1186/s13756-019-0533-3

Sikkema, D. J., Murphy, T. F., 1992. Molecular analysis of the P2 porin protein of nontypeable Haemophilus influenzae. Infect Immun 60, 5204-5211. doi: 10.1128/IAI.60.12.5204-5211.1992

Silva, M. D., Sillankorva, S., 2019. Otitis media pathogens—A life entrapped in biofilm communities. Crit Rev Microbiol 45, 595-612. doi: 10.1080/1040841X.2019.1660616

Sirakova, T., Kolattukudy, P. E., Murwin, D., Billy, J., Leake, E., Lim, D., DeMaria, T., Bakaletz, L., 1994. Role of fimbriae expressed by nontypeable Haemophilus influenzae in pathogenesis of and protection against otitis media and relatedness of the fimbrin subunit to outer membrane protein A. Infect Immun 62, 2002-2020. doi:

Song, J. H., Dagan, R., Klugman, K. P., Fritzell, B., 2012. The relationship between pneumococcal serotypes and antibiotic resistance. Vaccine 30, 2728-2737. doi: 10.1016/j.vaccine.2012.01.091

Stewart, P. S., 2002. Mechanisms of antibiotic resistance in bacterial biofilms. Int J Med Microbiol 292, 107-113. doi: 10.1078/1438-4221-00196

Surette, M. G., Miller, M. B., Bassler, B. L., 1999. Quorum sensing in Escherichia coli, Salmonella typhimurium, and Vibrio harveyi: a new family of genes responsible for autoinducer production. Proc Natl Acad Sci USA 96, 1639-1644. doi: 10.1073/pnas.96.4.1639

Swords, W. E., Jones, P. A., Apicella, M. A., 2003. The lipo-oligosaccharides of Haemophilus influenzae: an interesting array of characters. J Endotoxin Res 9, 131-144. doi: 10.1179/096805103125001531

Tagliabue, A., Rappuoli, R., 2018. Changing priorities in vaccinology: Antibiotic resistance moving to the top. Front Immunol 9, 1068. doi: 10.3389/fimmu.2018.01068

Tatusov, R. L., Galperin, M. Y., Natale, D. A., Koonin, E. V., 2000. The COG database: a tool for genome-scale analysis of protein functions and evolution. Nucleic Acids Res 28, 33-36. doi: 10.1093/nar/28.1.33

Toone, S. L., Ratkiewicz, M., Novotny, L. A., Phong, B. L., Bakaletz, L. O., 2020. Nontypeable Haemophilus influenzae Type IV pilus mediates augmented adherence to rhinovirus-infected human airway epithelial cells. Infect Immun. doi: 10.1128/IAI.00248-20

Tristram, S., Jacobs, M. R., Appelbaum, P. C., 2007. Antimicrobial resistance in Haemophilus influenzae. Clin Microbiol Rev 20, 368-389. doi: 10.1128/CMR.00040-06

Vergison, A., 2008. Microbiology of otitis media: a moving target. Vaccine 26 Suppl 7, G5-10. doi: 10.1016/j.vaccine.2008.11.006

Wald, E. R., DeMuri, G. P., 2018. Antibiotic recommendations for acute otitis media and acute bacterial sinusitis: Conundrum no more. Pediatr Infect Dis J 37, 1255-1257. doi: 10.1097/INF.0000000000002009

Wasserman, R. C., Gerber, J. S., 2017. Acute otitis media in the 21st century: What now? Pediatrics 140. doi: 10.1542/peds.2017-1966

Whitchurch, C. B., Tolker-Nielsen, T., Ragas, P. C., Mattick, J. S., 2002. Extracellular DNA required for bacterial biofilm formation. Science 295, 1487. doi: 10.1126/science.295.5559.1487

Wickham, H., Chang, W., Henry, L., Pedersen, T. L., Takahashi, K., Wilke, C., Woo, K., Yutani, H., Dunnington, D., 2016. ggplot2: Elegant Graphics for Data Analysis. Springer-Verlag, New York.

Wiertsema, S. P., Kirkham, L. A., Corscadden, K. J., Mowe, E. N., Bowman, J. M., Jacoby, P., Francis, R., Vijayasekaran, S., Coates, H. L., Riley, T. V., Richmond, P., 2011. Predominance of nontypeable Haemophilus influenzae in children with otitis media following introduction of a 3+0 pneumococcal conjugate vaccine schedule. Vaccine 29, 5163-5170. doi: 10.1016/j.vaccine.2011.05.035

Ysebaert, C., Denoel, P., Weynants, V., Bakaletz, L. O., Novotny, L. A., Godfroid, F., Hermand, P., 2019. A protein E-PilA fusion protein shows vaccine potential against nontypeable Haemophilus influenzae in mice and chinchillas. Infect Immun 87, e00345-00319. doi: 10.1128/IAI.00345-19

Zapun, A., Contreras-Martel, C., Vernet, T., 2008. Penicillin-binding proteins and beta-lactam resistance. FEMS Microbiol Rev 32, 361-385. doi: 10.1111/j.1574-6976.2007.00095.x

What is claimed is:

1. A method to identify antibiotic sensitivity of a newly released bacteria (NRel bacteria) from a biofilm comprising pre-treating the biofilm for about 15 minutes to about 4 hours with an agent that disrupts the biofilm, contacting the NRel bacteria with a range of varying concentrations of one or more antibiotics, and determining the range of varying concentrations of one or more antibiotics that inhibit the growth of the NRel bacteria thereby identifying antibiotic sensitivity, wherein the agent that disrupts the biofilm comprises an anti-rsPilA antibody, an anti-DNABII antibody, or an antigen binding fragment thereof.

2. The method of claim 1, wherein antibiotic sensitivity is determined by a method that determines the concentration of the one or more antibiotics that kills at least 25% of the NRel bacteria.

3. The method of claim 1, wherein antibiotic sensitivity is determined for the range of varying concentrations of one or more antibiotics for more than one antibiotic.

4. The method of claim 3, wherein antibiotic sensitivity is determined for two antibiotics.

5. The method of claim 4, wherein the two antibiotics are provided in a ratio of 1:1 to 1:10 to each other.

6. The method of claim 4, wherein the two antibiotics are selected from: glutamate and tobramycin, glutamate and colisin, trimethoprim and sulfamethoxazole, trimethoprim and clarithromycin, amoxicillin and clavulanate, or trimethoprim and sulfamethoxazole.

7. The method of claim 1, wherein the bacteria is selected from *Moraxella catarrhalis, Enterococcus faecium, Staphylococcus aureus, Klebsiella pneumoniae, Acinetobacter baumannii, Pseudomonas aeruginosa* or *Enterobacter* spp.

8. The method of claim 1, wherein the biofilm comprises a single or dual species biofilm.

9. The method of claim 8, wherein the biofilm is formed by a bacteria comprising one or more of *Aggregatibacter actinomycetemcomitans, Enterococcus faecium, Staphylococcus aureus, Klebsiella pneumoniae, Acinetobacter baumannii, Pseudomonas aeruginosa* or *Enterobacter* spp.

10. The method of claim 9, wherein the biofilm is formed by *Moraxella catarrhalis* and one or more of *Aggregatibacter actinomycetemcomitans, Enterococcus faecium, Staphylococcus aureus, Klebsiella pneumoniae, Acinetobacter baumannii, Pseudomonas aeruginosa* or *Enterobacter* spp.

11. The method of claim 1, wherein the antibiotic comprises one or more of piperacillin, ceftazidime, sulfonamide, a β-lactam antibiotic, tobramycin, colisin, trimethoprim, sulfamethoxazole, clarithromycin, glutamate, ampicillin, amoxicillin, clavulanate or cefdinir.

12. The method of claim 1, wherein the anti-DNABII antibody comprises an antibody selected from an anti-IHF antibody, an anti-IHF tip antibody, anti-tip chimer antibody and fragments thereof.

13. The method of claim 1, wherein the agent that disrupts the biofilm comprises an anti-rsPilA antibody.

14. The method of claim 1, wherein the agent that disrupts the biofilm comprises an anti-DNABII antibody.

15. The method of claim 14, wherein the anti-DNABII antibody comprises an anti-IHF antibody.

16. The method of claim 1, further comprising identifying the minimal inhibitory concentration for the antibiotic.

17. The method of claim 1, further comprising performing transcriptional profiling of the NRel bacteria.

18. The method of claim 1, wherein antibiotic sensitivity is determined by a method that determines the concentration of the one or more antibiotics that kills from 10% to 50% of the NRel bacteria.

19. The method of claim 1, wherein the biofilm is pre-treated with the agent that disrupts the biofilm for about 2 hours.

20. The method of claim 1, wherein the agent that disrupts the biofilm reduces formation of a DNA/protein matrix that is a component of the biofilm.

* * * * *

SEQUENCE LISTING

<160> NUMBER OF SEQ ID NOS: 57

<210> SEQ ID NO 1
<211> LENGTH: 21
<212> TYPE: PRT
<213> ORGANISM: Artificial Sequence
<220> FEATURE:
<223> OTHER INFORMATION: IhfA

<400> SEQUENCE: 1

Asn Phe Glu Leu Arg Asp Lys Ser Ser Arg Pro Gly Arg Asn Pro Lys
1               5                   10                  15

Thr Gly Asp Val Val
            20

<210> SEQ ID NO 2
<211> LENGTH: 21
<212> TYPE: PRT
<213> ORGANISM: Artificial Sequence
<220> FEATURE:
<223> OTHER INFORMATION: IhfB

<400> SEQUENCE: 2

Ser Leu His His Arg Gln Pro Arg Leu Gly Arg Asn Pro Lys Thr Gly
1               5                   10                  15

Asp Ser Val Asn Leu
            20

<210> SEQ ID NO 3
<211> LENGTH: 41
<212> TYPE: PRT
<213> ORGANISM: Artificial Sequence
<220> FEATURE:
<223> OTHER INFORMATION: IhfA5-mIhfB4NTHI
<220> FEATURE:
<221> NAME/KEY: MOD_RES
<222> LOCATION: (7)..(7)
<223> OTHER INFORMATION: Xaa can be any amino acid or Q, R, K, S, or T
<220> FEATURE:
<221> NAME/KEY: MISC_FEATURE
<222> LOCATION: (21)..(21)
<223> OTHER INFORMATION: Xaa is an optional amino acid linker between 1
      and 20 amino acids
<220> FEATURE:
<221> NAME/KEY: MOD_RES
<222> LOCATION: (36)..(36)
<223> OTHER INFORMATION: Xaa can be any amino acid or Q, R, K, S, or T

<400> SEQUENCE: 3

Arg Pro Gly Arg Asn Pro Xaa Thr Gly Asp Val Val Pro Val Ser Ala
1               5                   10                  15

Arg Arg Val Val Xaa Phe Ser Leu His His Arg Gln Pro Arg Leu Gly
            20                  25                  30

Arg Asn Pro Xaa Thr Gly Asp Ser Val
        35                  40

<210> SEQ ID NO 4
<211> LENGTH: 7
<212> TYPE: PRT
<213> ORGANISM: Artificial Sequence
<220> FEATURE:
<223> OTHER INFORMATION: CDRH1

<400> SEQUENCE: 4

Gly Phe Thr Phe Arg Thr Tyr
1               5

```
<210> SEQ ID NO 5
<211> LENGTH: 6
<212> TYPE: PRT
<213> ORGANISM: Artificial Sequence
<220> FEATURE:
<223> OTHER INFORMATION: CDRH2

<400> SEQUENCE: 5

Gly Ser Asp Arg Arg His
1               5

<210> SEQ ID NO 6
<211> LENGTH: 13
<212> TYPE: PRT
<213> ORGANISM: Artificial Sequence
<220> FEATURE:
<223> OTHER INFORMATION: CDRH3

<400> SEQUENCE: 6

Val Gly Pro Tyr Asp Gly Tyr Tyr Gly Glu Phe Asp Tyr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: CDRL1

<400> SEQUENCE: 7

Gln Ser Leu Leu Asp Ser Asp Gly Lys Thr Phe
1               5                   10

<210> SEQ ID NO 8
<211> LENGTH: 7
<212> TYPE: PRT
<213> ORGANISM: Artificial Sequence
<220> FEATURE:
<223> OTHER INFORMATION: CDRL3

<400> SEQUENCE: 8

Trp Gln Gly Thr His Phe Pro
1               5

<210> SEQ ID NO 9
<211> LENGTH: 8
<212> TYPE: PRT
<213> ORGANISM: Artificial Sequence
<220> FEATURE:
<223> OTHER INFORMATION: CDRH1

<400> SEQUENCE: 9

Gly Phe Thr Phe Arg Thr Tyr Ala
1               5

<210> SEQ ID NO 10
<211> LENGTH: 8
<212> TYPE: PRT
<213> ORGANISM: Artificial Sequence
<220> FEATURE:
<223> OTHER INFORMATION: CDRH2

<400> SEQUENCE: 10

Ile Gly Ser Asp Arg Arg His Thr
1               5
```

```
<210> SEQ ID NO 11
<211> LENGTH: 9
<212> TYPE: PRT
<213> ORGANISM: Artificial Sequence
<220> FEATURE:
<223> OTHER INFORMATION: CDRL3

<400> SEQUENCE: 11

Trp Gln Gly Thr His Phe Pro Tyr Thr
1               5

<210> SEQ ID NO 12
<211> LENGTH: 13
<212> TYPE: PRT
<213> ORGANISM: Artificial Sequence
<220> FEATURE:
<223> OTHER INFORMATION: CDRH1
<220> FEATURE:
<221> NAME/KEY: MOD_RES
<222> LOCATION: (1)..(1)
<223> OTHER INFORMATION: Xaa = A or K

<400> SEQUENCE: 12

Xaa Ala Ser Gly Phe Thr Phe Arg Thr Tyr Ala Met Ser
1               5                   10

<210> SEQ ID NO 13
<211> LENGTH: 10
<212> TYPE: PRT
<213> ORGANISM: Artificial Sequence
<220> FEATURE:
<223> OTHER INFORMATION: CDRH2

<400> SEQUENCE: 13

Thr Ile Gly Ser Asp Arg Arg His Thr Tyr
1               5                   10

<210> SEQ ID NO 14
<211> LENGTH: 16
<212> TYPE: PRT
<213> ORGANISM: Artificial Sequence
<220> FEATURE:
<223> OTHER INFORMATION: CDRL1
<220> FEATURE:
<221> NAME/KEY: MOD_RES
<222> LOCATION: (1)..(1)
<223> OTHER INFORMATION: Xaa = R or K

<400> SEQUENCE: 14

Xaa Ser Ser Gln Ser Leu Leu Asp Ser Asp Gly Lys Thr Phe Leu Asn
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: CDRL2
<220> FEATURE:
<221> NAME/KEY: MOD_RES
<222> LOCATION: (6)..(6)
<223> OTHER INFORMATION: Xaa= L or R

<400> SEQUENCE: 15

Tyr Leu Val Ser Lys Xaa Asp Ser
1               5

<210> SEQ ID NO 16
<211> LENGTH: 7
```

```
<212> TYPE: PRT
<213> ORGANISM: Artificial Sequence
<220> FEATURE:
<223> OTHER INFORMATION: CDRH1

<400> SEQUENCE: 16

Gly Phe Thr Phe Ser Arg Tyr
1               5

<210> SEQ ID NO 17
<211> LENGTH: 6
<212> TYPE: PRT
<213> ORGANISM: Artificial Sequence
<220> FEATURE:
<223> OTHER INFORMATION: CDRH2

<400> SEQUENCE: 17

Ser Ser Gly Gly Ser Tyr
1               5

<210> SEQ ID NO 18
<211> LENGTH: 6
<212> TYPE: PRT
<213> ORGANISM: Artificial Sequence
<220> FEATURE:
<223> OTHER INFORMATION: CDRL1

<400> SEQUENCE: 18

Gln Asp Ile Ser Asn Tyr
1               5

<210> SEQ ID NO 19
<211> LENGTH: 472
<212> TYPE: PRT
<213> ORGANISM: Artificial Sequence
<220> FEATURE:
<223> OTHER INFORMATION: 1F8.F1 Humanized HC1

<400> SEQUENCE: 19

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
                20                  25                  30

Gly Gly Leu Val Gln Pro Gly Gly Ser Leu Arg Leu Ser Cys Ala Ala
            35                  40                  45

Ser Gly Phe Thr Phe Arg Thr Tyr Ala Met Ser Trp Val Arg Gln Ala
        50                  55                  60

Pro Gly Lys Gly Leu Glu Trp Val Ala Thr Ile Gly Ser Asp Arg Arg
65                  70                  75                  80

His Thr Tyr Tyr Pro Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
                100                 105                 110

Glu Asp Thr Ala Val Tyr Tyr Cys Val Gly Pro Tyr Asp Gly Tyr Tyr
            115                 120                 125

Gly Glu Phe Asp Tyr Trp Gly Gln Gly Thr Leu Val Thr Val Ser Ser
        130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175
```

-continued

Phe Pro Glu Pro Val Thr Val Ser Trp Asn Ser Gly Ala Leu Thr Ser
                180                 185                 190

Gly Val His Thr Phe Pro Ala Val Leu Gln Ser Gly Leu Tyr Ser
            195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Glu Glu Met
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
450                 455                 460

Lys Ser Leu Ser Leu Ser Pro Gly
465                 470

<210> SEQ ID NO 20
<211> LENGTH: 239
<212> TYPE: PRT
<213> ORGANISM: Artificial Sequence
<220> FEATURE:
<223> OTHER INFORMATION: 1F8.F1 Humanized (LC2)

<400> SEQUENCE: 20

Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Leu Pro
                20                  25                  30

Val Thr Leu Gly Gln Pro Ala Ser Ile Ser Cys Arg Ser Ser Gln Ser
            35                  40                  45

Leu Leu Asp Ser Asp Gly Lys Thr Phe Leu Asn Trp Leu Gln Gln Arg
        50                  55                  60

```
Pro Gly Gln Ser Pro Arg Arg Leu Ile Tyr Leu Val Ser Lys Arg Asp
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Tyr
            100                 105                 110

Cys Trp Gln Gly Thr His Phe Pro Tyr Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

```
<210> SEQ ID NO 21
<211> LENGTH: 13
<212> TYPE: PRT
<213> ORGANISM: Artificial Sequence
<220> FEATURE:
<223> OTHER INFORMATION: CDR1

<400> SEQUENCE: 21

Ala Ala Ser Gly Phe Thr Phe Arg Thr Tyr Ala Met Ser
1               5                   10

<210> SEQ ID NO 22
<211> LENGTH: 13
<212> TYPE: PRT
<213> ORGANISM: Artificial Sequence
<220> FEATURE:
<223> OTHER INFORMATION: CDR1

<400> SEQUENCE: 22

Lys Ala Ser Gly Phe Thr Phe Arg Thr Tyr Ala Met Ser
1               5                   10

<210> SEQ ID NO 23
<211> LENGTH: 9
<212> TYPE: PRT
<213> ORGANISM: Artificial Sequence
<220> FEATURE:
<223> OTHER INFORMATION: CDR2

<400> SEQUENCE: 23

Ile Gly Ser Asp Arg Arg His Thr Tyr
1               5

<210> SEQ ID NO 24
<211> LENGTH: 16
<212> TYPE: PRT
<213> ORGANISM: Artificial Sequence
<220> FEATURE:
<223> OTHER INFORMATION: CDR1
```

```
<400> SEQUENCE: 24

Arg Ser Ser Gln Ser Leu Leu Asp Ser Asp Gly Lys Thr Phe Leu Asn
1               5                   10                  15

<210> SEQ ID NO 25
<211> LENGTH: 8
<212> TYPE: PRT
<213> ORGANISM: Artificial Sequence
<220> FEATURE:
<223> OTHER INFORMATION: CDR2

<400> SEQUENCE: 25

Tyr Leu Val Ser Lys Leu Asp Ser
1               5

<210> SEQ ID NO 26
<211> LENGTH: 7
<212> TYPE: PRT
<213> ORGANISM: Artificial Sequence
<220> FEATURE:
<223> OTHER INFORMATION: CDR2

<400> SEQUENCE: 26

Leu Val Ser Lys Leu Asp Ser
1               5

<210> SEQ ID NO 27
<211> LENGTH: 8
<212> TYPE: PRT
<213> ORGANISM: Artificial Sequence
<220> FEATURE:
<223> OTHER INFORMATION: CDR2

<400> SEQUENCE: 27

Tyr Leu Val Ser Lys Arg Asp Ser
1               5

<210> SEQ ID NO 28
<211> LENGTH: 7
<212> TYPE: PRT
<213> ORGANISM: Artificial Sequence
<220> FEATURE:
<223> OTHER INFORMATION: CDR1

<400> SEQUENCE: 28

Leu Val Ser Lys Arg Asp Ser
1               5

<210> SEQ ID NO 29
<211> LENGTH: 16
<212> TYPE: PRT
<213> ORGANISM: Artificial Sequence
<220> FEATURE:
<223> OTHER INFORMATION: CDR1

<400> SEQUENCE: 29

Lys Ser Ser Gln Ser Leu Leu Asp Ser Asp Gly Lys Thr Phe Leu Asn
1               5                   10                  15

<210> SEQ ID NO 30
<211> LENGTH: 13
<212> TYPE: PRT
<213> ORGANISM: Artificial Sequence
<220> FEATURE:
<223> OTHER INFORMATION: CDR1
```

```
<400> SEQUENCE: 30

Ala Ala Ser Gly Phe Thr Phe Ser Arg Tyr Gly Met Ser
1               5                   10

<210> SEQ ID NO 31
<211> LENGTH: 8
<212> TYPE: PRT
<213> ORGANISM: Artificial Sequence
<220> FEATURE:
<223> OTHER INFORMATION: CDR1

<400> SEQUENCE: 31

Gly Phe Thr Phe Ser Arg Tyr Gly
1               5

<210> SEQ ID NO 32
<211> LENGTH: 10
<212> TYPE: PRT
<213> ORGANISM: Artificial Sequence
<220> FEATURE:
<223> OTHER INFORMATION: CDR2

<400> SEQUENCE: 32

Thr Ile Ser Ser Gly Gly Ser Tyr Thr Tyr
1               5                   10

<210> SEQ ID NO 33
<211> LENGTH: 8
<212> TYPE: PRT
<213> ORGANISM: Artificial Sequence
<220> FEATURE:
<223> OTHER INFORMATION: CDR2

<400> SEQUENCE: 33

Ile Ser Ser Gly Gly Ser Tyr Thr
1               5

<210> SEQ ID NO 34
<211> LENGTH: 13
<212> TYPE: PRT
<213> ORGANISM: Artificial Sequence
<220> FEATURE:
<223> OTHER INFORMATION: CDR3

<400> SEQUENCE: 34

Glu Arg His Gly Gly Asp Gly Tyr Trp Tyr Phe Asp Val
1               5                   10

<210> SEQ ID NO 35
<211> LENGTH: 13
<212> TYPE: PRT
<213> ORGANISM: Artificial Sequence
<220> FEATURE:
<223> OTHER INFORMATION: CDR1

<400> SEQUENCE: 35

Thr Ala Ser Gly Phe Thr Phe Ser Arg Tyr Gly Met Ser
1               5                   10

<210> SEQ ID NO 36
<211> LENGTH: 11
<212> TYPE: PRT
<213> ORGANISM: Artificial Sequence
<220> FEATURE:
<223> OTHER INFORMATION: CDR1

<400> SEQUENCE: 36
```

Arg Ala Ser Gln Asp Ile Ser Asn Tyr Leu Asn
1               5                   10

<210> SEQ ID NO 37
<211> LENGTH: 8
<212> TYPE: PRT
<213> ORGANISM: Artificial Sequence
<220> FEATURE:
<223> OTHER INFORMATION: CDR2

<400> SEQUENCE: 37

Tyr Tyr Thr Ser Arg Leu His Ser
1               5

<210> SEQ ID NO 38
<211> LENGTH: 7
<212> TYPE: PRT
<213> ORGANISM: Artificial Sequence
<220> FEATURE:
<223> OTHER INFORMATION: CDR2

<400> SEQUENCE: 38

Tyr Thr Ser Arg Leu His Ser
1               5

<210> SEQ ID NO 39
<211> LENGTH: 8
<212> TYPE: PRT
<213> ORGANISM: Artificial Sequence
<220> FEATURE:
<223> OTHER INFORMATION: CDR3

<400> SEQUENCE: 39

Gln Gln Gly Asn Pro Leu Arg Thr
1               5

<210> SEQ ID NO 40
<211> LENGTH: 22
<212> TYPE: DNA
<213> ORGANISM: Artificial Sequence
<220> FEATURE:
<223> OTHER INFORMATION: acrR-forward primer

<400> SEQUENCE: 40
cggcgataaa tttagcctct ga                                              22

<210> SEQ ID NO 41
<211> LENGTH: 18
<212> TYPE: DNA
<213> ORGANISM: Artificial Sequence
<220> FEATURE:
<223> OTHER INFORMATION: acrR-reverse primer

<400> SEQUENCE: 41
tgaatcgcac gccaagag                                                   18

<210> SEQ ID NO 42
<211> LENGTH: 22
<212> TYPE: DNA
<213> ORGANISM: Artificial Sequence
<220> FEATURE:
<223> OTHER INFORMATION: artM-forward primer

<400> SEQUENCE: 42
gtcttatcca atgcgtggtt ct                                              22

<210> SEQ ID NO 43
<211> LENGTH: 22
<212> TYPE: DNA
<213> ORGANISM: Artificial Sequence
<220> FEATURE:
<223> OTHER INFORMATION: artm-reverse primer

<400> SEQUENCE: 43
ggatgctaat gccgttcctt ta                                              22

<210> SEQ ID NO 44
<211> LENGTH: 21
<212> TYPE: DNA
<213> ORGANISM: Artificial Sequence
<220> FEATURE:
<223> OTHER INFORMATION: deaD-forward primer

<400> SEQUENCE: 44
tgtggtgaac tacgacattc c                                               21

<210> SEQ ID NO 45
<211> LENGTH: 22
<212> TYPE: DNA
<213> ORGANISM: Artificial Sequence
<220> FEATURE:
<223> OTHER INFORMATION: deaD-reverse primer

<400> SEQUENCE: 45
gatcctgatc ggctgtgaat aa                                              22

<210> SEQ ID NO 46
<211> LENGTH: 23
<212> TYPE: DNA
<213> ORGANISM: Artificial Sequence
<220> FEATURE:
<223> OTHER INFORMATION: emrA-forward primer

<400> SEQUENCE: 46
ccgcaaatac agaatgcgat aaa                                             23

<210> SEQ ID NO 47
<211> LENGTH: 19
<212> TYPE: DNA
<213> ORGANISM: Artificial Sequence
<220> FEATURE:
<223> OTHER INFORMATION: emrA-reverse primer

<400> SEQUENCE: 47
attacgacgc gccacatag                                                  19

<210> SEQ ID NO 48
<211> LENGTH: 20
<212> TYPE: DNA
<213> ORGANISM: Artificial Sequence
<220> FEATURE:
<223> OTHER INFORMATION: emrB-forward primer

<400> SEQUENCE: 48
cggtaacttt cgagccatca                                                 20

<210> SEQ ID NO 49
<211> LENGTH: 22
<212> TYPE: DNA
<213> ORGANISM: Artificial Sequence
<220> FEATURE:
<223> OTHER INFORMATION: emrB-reverse primer

<400> SEQUENCE: 49
gccagacagc gttattgtag ta                                              22

<210> SEQ ID NO 50
<211> LENGTH: 21
<212> TYPE: DNA
<213> ORGANISM: Artificial Sequence
<220> FEATURE:
<223> OTHER INFORMATION: fis-forward primer

<400> SEQUENCE: 50
taatcctgcc gatgccttaa c                                               21

<210> SEQ ID NO 51
<211> LENGTH: 22
<212> TYPE: DNA
<213> ORGANISM: Artificial Sequence
<220> FEATURE:
<223> OTHER INFORMATION: fis-reverse primer

<400> SEQUENCE: 51
cgggtttgat taccacgagt at                                              22

<210> SEQ ID NO 52
<211> LENGTH: 21
<212> TYPE: DNA
<213> ORGANISM: Artificial Sequence
<220> FEATURE:
<223> OTHER INFORMATION: folA-forward primer

<400> SEQUENCE: 52
ttggtcgtcc actacctaaa c                                               21

<210> SEQ ID NO 53
<211> LENGTH: 21
<212> TYPE: DNA
<213> ORGANISM: Artificial Sequence
<220> FEATURE:
<223> OTHER INFORMATION: folA-reverse primer

<400> SEQUENCE: 53
gaccgcactt tcaaagctat c                                               21

<210> SEQ ID NO 54
<211> LENGTH: 22
<212> TYPE: DNA
<213> ORGANISM: Artificial Sequence
<220> FEATURE:
<223> OTHER INFORMATION: folP-forward primer

<400> SEQUENCE: 54
tgctggattt ctgtcgattc tt                                              22

<210> SEQ ID NO 55
<211> LENGTH: 22
<212> TYPE: DNA
<213> ORGANISM: Artificial Sequence
<220> FEATURE:
<223> OTHER INFORMATION: folP-reverse primer

<400> SEQUENCE: 55
gctcttgcaa agcacgaata tc                                              22

<210> SEQ ID NO 56

```
<211> LENGTH: 22
<212> TYPE: DNA
<213> ORGANISM: Artificial Sequence
<220> FEATURE:
<223> OTHER INFORMATION: 16S-forward primer

<400> SEQUENCE: 56
aaaggagact gccagtgata aa                                          22

<210> SEQ ID NO 57
<211> LENGTH: 22
<212> TYPE: DNA
<213> ORGANISM: Artificial Sequence
<220> FEATURE:
<223> OTHER INFORMATION: 16S-reverse primer

<400> SEQUENCE: 57
ccctctgtat acgccattgt ag                                          22
```